United States Patent [19]
Oshima et al.

[11] Patent Number: 5,902,569
[45] Date of Patent: May 11, 1999

[54] ULTRAVIOLET SHIELDING COMPOSITE FINE PARTICLES, METHOD FOR PRODUCING THE SAME, AND COSMETICS

[75] Inventors: Kentaro Oshima; Shunji Kozaki; Yoshinobu Imaizumi; Toshio Miyake; Toru Nishimura; Keiichi Tsuto, all of Wakayama; Satoshi Sugawara; Makoto Torizuka, both of Tokyo, all of Japan

[73] Assignee: Kao Corporation, Tokyo, Japan

[21] Appl. No.: 08/894,672

[22] PCT Filed: Mar. 7, 1996

[86] PCT No.: PCT/JP96/00593

§ 371 Date: Aug. 27, 1997

§ 102(e) Date: Aug. 27, 1997

[87] PCT Pub. No.: WO96/28137

PCT Pub. Date: Sep. 19, 1996

[30] Foreign Application Priority Data

Mar. 10, 1995 [JP] Japan .................................... 7-079717
Mar. 28, 1995 [JP] Japan .................................... 7-096053

[51] Int. Cl.⁶ .............................. A61K 7/42; A61K 7/44; A61K 9/00; A61K 6/00
[52] U.S. Cl. ........................... 424/59; 423/462; 423/592; 424/59; 424/60; 424/400; 424/401
[58] Field of Search ................................ 424/59, 60, 400, 424/401; 423/462, 592

[56] References Cited

U.S. PATENT DOCUMENTS

| | | | |
|---|---|---|---|
| 4,927,464 | 5/1990 | Cowie | 106/436 |
| 5,298,065 | 3/1994 | Hiraoka et al. | 106/425 |
| 5,478,550 | 12/1995 | Suzuki et al. | 424/59 |

OTHER PUBLICATIONS

Hawley's Condensed Chemical Dictionary, 12th edition, revised by R.J.Lewis, Sr., Van Nostrand Reinhold Company, New York, pp. 668, 783, 784, 1113, 1993.

The Facts on File Dictionary of Chemistry, edited by J. Daintith, FactsOnFile, New York, p. 198, 1988.

*Primary Examiner*—Shelley A. Dodson
*Assistant Examiner*—Marina Lamm
*Attorney, Agent, or Firm*—Birch, Stewart, Kolasch & Birch, LLP.

[57] ABSTRACT

The present invention is directed to ultraviolet shielding composite fine particles having transparency in a visible light region include (a) matrix particles comprising an aggregate of primary particles having an average particle diameter of from 0.001 to 0.3 μm, the aggregate being formed while the primary particles retain their shapes; and (b) daughter particles having an average particle diameter of from 0.001 to 0.1 μm, the daughter particles being dispersed in and supported by the matrix particles. In the composite fine particles, the daughter particles have a smaller band gap energy than the particles constituting the matrix particles and are capable of absorbing ultraviolet light, and the resulting ultraviolet shielding composite fine particles have substantially no catalytic activity.

25 Claims, 8 Drawing Sheets

ULTRAVIOLET SHIELDING COMPOSITE FINE PARTICLES, METHOD FOR PRODUCING THE SAME, AND COSMETICS

TECHNICAL FIELD

The present invention relates to ultraviolet shielding composite fine particles having substantially no catalytic activity, having high transparency in the visible light region, and a high shielding ability in the ultraviolet light region. It also relates to a method for producing the composite fine particles, and cosmetics containing such composite fine particles.

BACKGROUND ART

The sunlight reaching the earth includes infrared light, visible light, and ultraviolet light, of which 5 to 6% is ultraviolet light. The ultraviolet light has short wavelengths, which are thus high-energy electromagnetic waves. Therefore, the ultraviolet light is known to decompose many kinds of materials and to damage living organisms.

Therefore, ultraviolet shielding agents are used for protecting skin from inflammation or skin cancer due to exposure of the skin to harmful ultraviolet light. For this purpose, the ultraviolet shielding agents are added to cosmetics. Also, they are used to prevent pigments from fading due to decomposition by ultraviolet light. For this purpose, the ultraviolet shielding agents are mixed with paints; however, this may cause unnatural skin whitening and a color change of paints. This can be prevented by increasing the transparency of such cosmetics or paints in the visible light region. Therefore, the ultraviolet light is desirably blocked while the transparency in the visible light region is maintained.

The ultraviolet shielding agent comprising organic compounds as effective ingredients prevents the transmission of the ultraviolet light on account of the above organic compounds which absorb the ultraviolet light. For example, an ultraviolet absorbent composition comprising substituted N,N'-bis-aromatic formamidines is known (Japanese Patent Examined Publication No. 61-09993). However, the organic ultraviolet shielding agents have the problem that although they can absorb the ultraviolet light, they are at the same time likely to be decomposed by the ultraviolet light, with the result of an undesirable lowering of the shielding ability over time. Regarding their application to cosmetics, the kinds and amounts of the ultraviolet shielding agents are restricted owing to deleterious effects caused on human bodies, and thus it is difficult to achieve a good shielding performance within a controlled range.

On the other hand, the ultraviolet shielding agent comprising an inorganic compound contains inorganic fine particles and prevents the transmission of ultraviolet light by the absorbing ability and the scattering ability of the composition. The inorganic ultraviolet shielding agent is superior to the organic ultraviolet shielding agent because the composition containing the inorganic ultraviolet shielding agent is not decomposed by the ultraviolet light with the passage of time and has little effects on the human body.

However, since the inorganic ultraviolet shielding agents are present in the form of particles, it is more difficult with inorganic ultraviolet shielding agents when compared with organic ultraviolet shielding agents to block the ultraviolet light while maintaining high transparency in the visible light region.

In order to possess an effective light shielding ability in the ultraviolet light region while maintaining high transparency in the visible light region (light wavelengths of from 400 to 800 nm), the composition has to be microgranulated to give ultrafine particles capable of being highly dispersed so as to increase the ultraviolet scattering ability. However, in the case of using ultrafine particles, dispersion stability problems may arise due to the aggregation of the ultrafine particles and the catalytic activities of the ultrafine particles.

In order to improve dispersibility, the ultrafine particle surfaces may be coated with other materials For example, skin cosmetics comprising an oily cosmetic base material and a hydrophobic titanium oxide powder are known (Japanese Patent Examined Publication No. 59-15885). However, a suitable solvent has to be selected depending upon the properties of the materials coated on the surface. Also, since the particles are still ultrafine, the aggregation of the ultrafine particles can only be lowered to a limited extent even if the surface treatment is conducted. In publications other than those mentioned above, there have been known cosmetics containing a powder obtainable by coating titanium oxide with a particular amount of mixed hydrates comprising silicate hydrates and aluminum hydrates, titanium oxide being nearly spherical or irregularly shaped and having an average particle diameter of from 30 to 70 nm, wherein the surface of the hydrate-coated titanium oxide is optionally further coated with a silicone oil (Japanese Patent Laid-Open No. 2-247109). However, since in this publication the above powder is obtained by drying and pulverization of the product obtained after coating with the mixed hydrates comprising silicate hydrates and aluminum hydrates or after coating the surface of the powder with the silicone oil, it is extremely difficult to pulverize the titanium oxide ultrafine particles to the size of the primary particles, because the titanium oxide ultrafine particles are aggregated showing a large particle diameter, so that the transparency and the ultraviolet shielding ability of the above obtained powder are lowered. Also, since fresh, uncoated surfaces appear after the pulverization process is carried out, the water-repellent ability or the oil-repellent ability of these surfaces is undesirably lowered. Such technological problems arise in maintaining the dispersibility of the ultrafine particles stable. Therefore, it is increasingly important to find a way to achieve a high dispersibility of the ultrafine particles and maintain it at that level.

Also, for the purposes of providing cosmetics comprising ultrafine particles wherein the ultrafine particles are easily and uniformly dispersed and the problem of the difficult handling of the ultrafine particles powder is eliminated, starting materials for cosmetics comprising metal oxide ultrafine particles having a particle diameter of not more than 0.1 $\mu$m, a dispersion medium, and a dispersant, wherein the content of the ultrafine particles is not less than 10% by weight, have been known (Japanese Patent Laid-Open No. 6-239728) However, although the problems regarding the aggregation of the ultrafine particles and the deterioration of the dispersant, the dispersion medium, and cosmetics base materials caused by the catalytic activity of the metal oxide ultrafine particles have been known, they have neither been addressed nor solved in this publication. Moreover, the content of the metal oxide ultrafine particles in the starting materials for cosmetics is limited to not less than 10% by weight in order to control the amounts in the overall cosmetics in this publication. However, as long as the metal oxide ultrafine particles are uniformly and stably dispersed, the function of the metal oxide ultrafine particles is high, and the content of the metal oxide ultrafine particles needs not be limited to a minimum amount of 10% by weight in the starting materials for any kind of cosmetics.

Therefore, in order not to lower the ultraviolet scattering ability by the aggregation of the inorganic ultrafine particles, composites of the inorganic ultrafine particles are often formed with other relatively large carrier particles. For example, a thin flaky material dispersed with metal compound fine particles is known (Japanese Patent Laid-Open No. 63-126818). However, this publication does not disclose a specific construction of the fine particles for improving both the shielding ability in the ultraviolet light region and the transparency in the visible light region Furthermore, composite fine particles comprising ultrafine particles dispersed in and supported by the solid material are proposed. Conventional ultraviolet shielding composite fine particles include, for example, a composite powder in which a fine particle powder, such as $TiO_2$, is uniformly dispersed in plate particles of metal oxides, such as $SiO_2$ (Japanese Patent Laid-Open No. 1-143821); and composite particles in which a zirconium oxide powder or an aluminum oxide powder is carried on a surface of the matrix particles comprising such materials as nylon resins, silicone resins, and silicon oxide, and a titanium oxide powder or a zinc oxide powder dispersed in an inner portion of the matrix particles (Japanese Patent Laid-Open No. 2-49717).

However, in order to use the above composite particles as ultraviolet shielding agents, the composite particles are usually dispersed in a medium in the actual environment. In this case, since the metal oxides, such as titanium oxide, contained in the composite particles have catalytic activity, the deterioration of the medium is likely to take place. Also, when the difference between the refractive index of the composite particles and that of the medium is large, light scattering takes place at an interface of the composite particles and the medium, thereby making both the transparency in the visible light region and the shielding ability in the ultraviolet light region poor. Although these problems need to be solved, they have not been considered in the above publications.

In order to suppress the catalytic activities of the ultrafine particles, methods for coating a surface of the ultrafine particles with various materials have been used. For example, Japanese Patent Laid-Open No. 5-70331 discloses the preparation of cosmetics comprising fine particle powder wherein a basic compound and at least one of a hydrocarbon compound having a boiling point of from 100 to 200° C. and a silicone having a particular molecular structure are added during the production of titanium hydroxide which is obtainable by hydrolysis of a titanium alkoxide. However, in order to produce titanium hydroxide fine particle powder, the production process must comprise drying and pulverization processes, which results in a large particle diameter of the obtained titanium hydroxide fine particles. Thus, it is difficult for the particles to be highly effective in scattering ultraviolet light B (light wavelengths of from 280 to 320 nm), while maintaining high transparency of in the visible light region.

Also, the above publication has neither considered nor disclosed any method for producing ultrafine particles for the titanium hydroxide particles or methods for dispersing the ultrafine titanium hydroxide particles in cosmetics, in order to satisfy both high transparency in the visible light region and high shielding ability to the ultraviolet light. Moreover, in the ultraviolet shielding materials disclosed in this publication, titanium hydroxide or titanium oxide presumably absorbs the ultraviolet light B (light wavelengths of from 280 to 320 nm). This ultraviolet light B only penetrates the epidermis and a relatively upper layer of the dermis, causing sunburn or skin cancers. However, titanium hydroxide or titanium oxide does not at all absorb, light having wavelengths of from 350 to 400 nm, which are closer to those of the visible light of the ultraviolet light A (light wavelengths of from 320 to 400 nm). The ultraviolet light A reaches skin layers beyond the dermis, and produces suntan or fibrous modifications in the dermis. In other words, the ultraviolet absorbents disclosed in this publication mainly exhibit absorption of the ultraviolet light B by titanium hydroxide or titanium oxide, but their ultraviolet absorption effects are limited to a light wavelength of up to about 300 nm for an anatase-type titanium oxide and to a light wavelength of up to about 320 nm for a rutile-type titanium oxide.

Of the ultraviolet light reaching the earth, the energy proportion of the ultraviolet light A is about 15 times that of the ultraviolet light B. Therefore, in view of the above energy proportion of the ultraviolet lights A and B, it is important to shield both the ultraviolet light A as well as the ultraviolet light B, and simply shielding the ultraviolet light B is not sufficient. Moreover, it is becoming increasingly important to shield both the ultraviolet light B and the ultraviolet light A, while maintaining a high transparency in the visible light region. In particular, in the case where the ultraviolet light A is shielded, it is important to shield light wavelengths of from 350 to 400 nm, which are closer to light wavelengths of the visible light.

As mentioned above, in order to achieve an effective shielding ability in the ultraviolet light region which maintaining and high transparency in the visible light region, the ultraviolet shielding materials are made ultrafine so that they are present in a highly dispersed state. In order to further improve the transparency in the visible light region, it is important for the difference between the refractive indices of the ultraviolet shielding materials and those of surrounding media to be kept small. As the refractive index of the titania-containing composite powders disclosed in Japanese Patent Laid-Open Nos. 1-143821 and 6-116119 is limited to certain ranges determined by the compositional ratios of the components, the number of suitable dispersion media whose refractive index corresponds to the refractive index of the composite powder is inevitably limited as well. Therefore, great problems have been encountered in controlling the refractive index of the composite powder so as to match it with the refractive index of the dispersion medium used. Therefore, an effective means for solving these problems is in great demand.

Further, Japanese Patent Laid-Open No. 4-65312 is concerned with metal compound-containing porous silica bead, the production method thereof, and the powder deodorant produced. In this publication, the fine particles of the metal compounds having a primary particle diameter of from 0.001 to 0.3 $\mu$m are contained in the porous silica bead in an amount of from 0.1 to 30% by weight, and the porous silica bead contain substantially no voids of not less than 0.3 $\mu$m. In this case, when the fine particles of the metal compounds contained therein are suitably selected so as to have a refractive index close to the refractive index of silica (the refractive index being in the range of from 1.4 to 2.0), silica particles with further improved transparency can be obtained. However, the publication only discloses the range for the refractive index of the metal compound fine particles contained in the inner portion of the composite particles, but none of the total refractive index of the composite particles.

As explained above, in order to solve the problems inherent in the ultraviolet shielding agents comprising the ultrafine particles, several attempts have been made to use composites mainly comprising metal oxides. However, many of the compounds exhibiting good ultraviolet absorption properties, such as $TiO_2$ and ZnO, have relatively high refractive indices, so that the composite fine particles incorporating these ultrafine particles have refractive indices notably higher than aqueous solutions, conventional organic solvents, polymers, etc. When the above composite fine particles are dispersed in a medium, the present inventors have found that light scattering in the visible light region takes place at the interface of the composite fine particles and the medium, whereby the transparency of the medium is drastically lowered. However, a technical method of controlling the refractive index of the ultraviolet shielding particle of the composite fine particles has not been proposed so far.

In the fields of resin fillers, fluorine-based inorganic compounds, such as $MgF_2$ and $CaF_2$, or fluorine-based organic polymeric compounds, such as polyethylene tetrafluoride, which are known as low-refractive index materials having high transparency, are added to powders, etc. as starting materials to lower their refractive indices.

For instance, Japanese Patent Laid-Open No. 4-85346 discloses a glass powder, used as a transparent inorganic powder for resin fillers, comprising metal oxides, such as $SiO_2$, $Al_2O_3$, $B_2O_3$, BaO, SrO, ZnO, and MgO, and metal fluorides, the glass powder having a refractive index ($n_D$) adjusted in the range of from 1.44 to 1.70. The publication discloses that since the glass powder has a high light transmittance and does not show strong alkalinity, the resins do not undergo any substantial modification, and are significantly stabilized in resin hardening. However, the publication merely discloses that a highly transparent inorganic powder for resin fillers is obtainable by changing the compositional ratio of the materials, and the above metal oxides, etc. are not present as particles in the final product powder owing to the high-temperature melting production, and this publication does not refer to the ultraviolet shielding ability. Further, this publication does not disclose that the composite fine particles comprise aggregates of two or more kinds of fine particles as in the present invention or that the composite fine particles have the compositional dependency with respect to an average refractive index of the composite fine particles.

DISCLOSURE OF THE INVENTION

An object of the present invention is to provide ultraviolet shielding composite fine particles having substantially no catalytic activities, being uniformly and stably dispersed in a medium (for example, cosmetics and paints), having a high transparency in the visible light region and high shielding ability in the ultraviolet light region, and permitting easy handling.

Another object of the present invention is to provide a method of producing such ultraviolet shielding composite fine particles.

A further object of the present invention is to provide cosmetics containing such ultraviolet shielding composite fine particles.

These objects have been achieved by finding a high performance of the inorganic ultraviolet shielding agent in the composite fine particles comprising daughter particles having a good ultraviolet shielding ability (i.e., ultraviolet scattering ability and absorption ability) and matrix particles in which the daughter particles are dispersed and by which the daughter particles are supported, the matrix particles having the high dispersibility of the daughter particles Also, the present inventors have found that the advantageous effects of the ultrafine particles can be optimally achieved by a suitable combination of the matrix particles and the daughter particles based on the difference in their band gap energies.

Also, in the control of the refractive index of the composite fine particles which can be achieved by a suitable combination of the matrix particles containing metal oxides and low-refractive index fluorine compounds and the daughter particles, the present inventors have found that in the case where the refractive index of the composite fine particles is substantially equal to the refractive index of the medium, light scattering is well-restricted at the interface of the composite fine particles and the medium. In this case, regardless of whether the shape of the composite fine particles is spherical, plate-like, or acicular, and regardless of the surface roughness of the composite fine particles, the light can be well transmitted into the inner portion of the composite fine particles. Therefore, the transparency in the visible light region is remarkably improved, and a high shielding ability in the ultraviolet light region is achieved on account of the ultrafine particles dispersed in the inner portion of the composite fine particles. Also, the present inventors have found that when fine particles having a low refractive index and a particle diameter of not more than 0.3 $\mu$m are used, the total refractive index of the composite fine particles can be lowered without causing scattering of the visible light even when a fine particle size area is formed in the inner portion of the composite fine particles.

Also, the present inventors have found that the catalytic activities of the ultraviolet shielding composite fine particles can be substantially suppressed by coating a surface of the composite fine particles with an inorganic material having substantially no catalytic activities.

Furthermore, the present inventors have found that powders of composite fine particles are obtainable by subjecting the surface of the composite fine particles coated with the inorganic material having substantially no catalytic activities to a water-repellent treatment and pulverizing the treated composite fine particles, and that the ultraviolet shielding composite fine particles with easy handling are obtainable by subjecting the surface of the composite fine particles to a water-repellent treatment, and then dispersing the so treated composite fine particles in an oil agent.

Accordingly, an aspect of the present invention is as follows:

(1) Ultraviolet shielding composite fine particles having transparency in a visible light region, comprising:
   (a) matrix particles comprising an aggregate of primary particles having an average particle diameter of from 0.001 to 0.3 $\mu$m, the aggregate being formed, while the primary particles retain their shapes; and
   (b) daughter particles having an average particle diameter of from 0.001 to 0.1 $\mu$m, the daughter particles being dispersed in and supported by the matrix particles, wherein the daughter particles have a smaller band gap energy than the particles constituting the matrix particles and are capable of absorbing ultraviolet light, and wherein the ultraviolet shielding composite fine particles have substantially no catalytic activities;

(2) The ultraviolet shielding composite fine particles described in item (1) above, wherein the surface of the ultraviolet shielding composite fine particles is coated with an inorganic material having substantially no catalytic activities;

(3) The ultraviolet shielding composite fine particles described in item (1) or item (2) above, wherein the particles constituting the matrix particles have a band gap energy of from 3 to 9 eV;

(4) The ultraviolet shielding composite fine particles described in any one of items (1) to (3) above, wherein the difference between the band gap energies of the daughter particles and the particles constituting the matrix particles is not less than 0.2 eV;

(5) The ultraviolet shielding composite fine particles described in any one items (1) to (4) above, wherein the daughter particles are dispersed in and supported by the matrix particles in an amount of from 0.1 to 85% by volume;

(6) The ultraviolet shielding composite fine particles described in any one of items (1) to (5) above, wherein the average particle diameter of the ultraviolet shielding composite fine particles is not more than 0.5 $\mu$m;

(7) The ultraviolet shielding composite fine particles described in any one of items (1) to (6) above, wherein the average refractive index of the ultraviolet shielding composite fine particles is from 1.3 to 2.5;

(8) The ultraviolet shielding composite fine particles described in any one of items (1) to (7) above, wherein the particles constituting the matrix particles are selected from the group consisting of metal oxides, fluorine compounds, and mixtures thereof;

(9) The ultraviolet shielding composite fine particles described in item (8) above, wherein the metal oxide is selected from the group consisting of $SiO_2$, $Al_2O_3$, and a mixture thereof;

(10) The ultraviolet shielding composite fine particles described in any one of items (1) to (9) above, wherein the daughter particles are selected from the group consisting of $TiO_2$, ZnO, $CeO_2$, SiC, $SnO_2$, $WO_3$, $BaTiO_3$, $CaTiO_3$, $SrTiO_3$, and mixtures thereof;

(11) The ultraviolet shielding composite fine particles described in any one of items (2) to (10) above, wherein the inorganic material is a metal oxide;

(12) The ultraviolet shielding composite fine particles described in item (11) above, wherein the metal oxide used for the inorganic material is selected from the group consisting of $SiO_2$, $Al_2O_3$, and a mixture thereof;

(13) The ultraviolet shielding composite fine particles described in any one of items (1) to (12), wherein the surface of the composite fine particles is further treated by a water-repellant;

(14) The ultraviolet shielding composite fine particles described in any one of items (1) to (13), wherein the ultraviolet shielding composite fine particles have a light transmittance of not less than 80% at a wavelength of 800 nm, a light transmittance of not less than 20% at a wavelength of 400 nm, and a light transmittance of not more than 5% at least at one wavelength within the range from 380 nm to 300 nm, the light transmittance being determined by suspending the composite fine particles in a medium having substantially the same refractive index level as the composite fine particles, and measuring with an ultraviolet-visible light spectrophotometer using an optical cell having an optical path length of 1 mm;

(15) The ultraviolet shielding composite fine particles described in any one of items (1) to (14), obtainable by the steps of:
  (a) preparing a liquid mixture comprising:
    (i) starting materials for matrix particles which are present in one or more forms selected from the group consisting of sols containing particles constituting matrix particles and powders of the matrix particles, the matrix particles having a primary particle with an average particle diameter of from 0.001 to 0.3 $\mu$m; and
    (ii) starting materials for daughter particles which are present in one or more forms selected from the group consisting of sols containing daughter particles and powders of the daughter particles, the daughter particles having a primary particle with an average particle diameter of from 0.001 to 0.1 $\mu$m, and treating the liquid mixture in a mill and/or an apparatus for high-pressure dispersion, to thereby produce composite fine particles wherein the daughter particles and the matrix particles are aggregated;
  (b) coating the composite fine particles obtained in step (a) with an inorganic material;
  (c) subjecting the composite fine particles coated with the inorganic material obtained in step (b) to a water-repellent treatment; and
  (d) drying and/or pulverizing the composite fine particles subjected to the water-repellent treatment obtained in step (c);

(16) A dispersion oil agent of the ultraviolet shielding composite fine particles as defined in any one of items (1) to (14) above, obtainable by the steps of:
  (a) preparing a liquid mixture comprising:
    (i) starting materials for matrix particles which are present in one or more forms selected from the group consisting of sols containing particles constituting matrix particles and powders of the matrix particles, the matrix particles having a primary particle with an average particle diameter of from 0.001 to 0.3 $\mu$m; and
    (ii) starting materials for daughter particles which are present in one or more forms selected from the group consisting of sols containing daughter particles and powders of the daughter particles, the daughter particles having a primary particle with an average particle diameter of from 0.001 to 0.1 $\mu$m, and treating the liquid mixture in a mill and/or an apparatus for high-pressure dispersion, to thereby produce composite fine particles wherein the daughter particles and the matrix particles are aggregated;
  (b) coating the composite fine particles obtained in step (a) with an inorganic material;
  (c) subjecting the composite fine particles coated with the inorganic material obtained in step (b) to a water-repellent treatment; and
  (d') dispersing in an oil agent the composite fine particles subjected to the water-repellent treatment obtained in step (c);

(17) A method for producing the ultraviolet shielding composite fine particles comprising daughter particles being dispersed in and supported by the matrix particles, the ultraviolet shielding composite fine particles having substantially no catalytic activities and transparency in a visible light region, obtainable by the steps of:
  (a) preparing a liquid mixture comprising (i) starting materials for matrix particles which are present in one or more forms selected from the group consisting of sols containing particles constituting matrix particles and powders of the matrix particles, the matrix particles having a primary particle with an average particle diameter of from 0.001 to 0.3 μm; and (ii) starting materials for daughter particles which are present in one or more forms selected from the group consisting of sols containing daughter particles and powders of the daughter particles, the daughter particles having a primary particle with an average particle diameter of from 0.001 to 0.1 μm, and treating the liquid mixture in a mill and/or an apparatus for high-pressure dispersion, to thereby produce composite fine particles wherein the daughter particles and the matrix particles are aggregated; and (b) coating the composite fine particles obtained in step (a) with an inorganic material;

(18) The method described in item (17) above, further comprising, subsequent to step (b) above:

(c) subjecting the composite fine particles coated with the inorganic material obtained in step (b) to a water-repellent treatment;

(19) The method described in item (18) above, further comprising, subsequent to step (c) above:

(d) drying and/or pulverizing the composite fine particles subjected to the water-repellent treatment obtained in step (c);

(20) A method for producing the dispersion oil agent of the ultraviolet shielding composite fine particles comprising daughter particles being dispersed in and supported by the matrix particles, the ultraviolet shielding composite fine particles having substantially no catalytic activities and transparency in a visible light region, obtainable by the steps of:

(a) preparing a liquid mixture comprising (i) starting materials for matrix particles which are present in one or more forms selected from the group consisting of sols containing particles constituting matrix particles and powders of the matrix particles, the matrix particles having a primary particle with an average particle diameter of from 0.001 to 0.3 μm; and (ii) starting materials for daughter particles which are present in one or more forms selected from the group consisting of sols containing daughter particles and powders of the daughter particles, the daughter particles having a primary particle with an average particle diameter of from 0.001 to 0.1 μm, and treating the liquid mixture in a mill and/or an apparatus for high-pressure dispersion, to thereby produce composite fine particles wherein the daughter particles and the matrix particles are aggregated;

(b) coating the composite fine particles obtained in step (a) with an inorganic material;

(c) subjecting the composite fine particles coated with the inorganic material obtained in step (b) to a water-repellent treatment; and (d') dispersing in an oil agent the composite fine particles subjected to the water-repellent treatment obtained in step (c);

(21) Cosmetics comprising ultraviolet shielding composite fine particles as defined in any one of items (1) to (15) above;

(22) Cosmetics comprising the dispersion oil agent of the ultraviolet shielding composite fine particles as defined in item (16);

(23) The cosmetics described in any one of items (18) to (21) above, wherein the amount of the ultraviolet shielding composite fine particles is from 0.1 to 50% by weight;

(24) The cosmetics described in any one of items (21) to (23) above, further containing an ultraviolet protecting agent;

(25) The cosmetics described in any one of items (21) to (24) above, wherein SPF measured by using an analyzer "SPF-290," manufactured by The Optometrics Group is not less than 8, and wherein $\Delta E^*ab$ before and after skin application is not more than 3 as defined according to JIS z 8729-1980; and

(26) The use of the ultraviolet shielding composite fine particles as defined in any one of items (1) to (15) as cosmetics.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein.

BEST MODE FOR CARRYING OUT THE INVENTION

Figure 1:
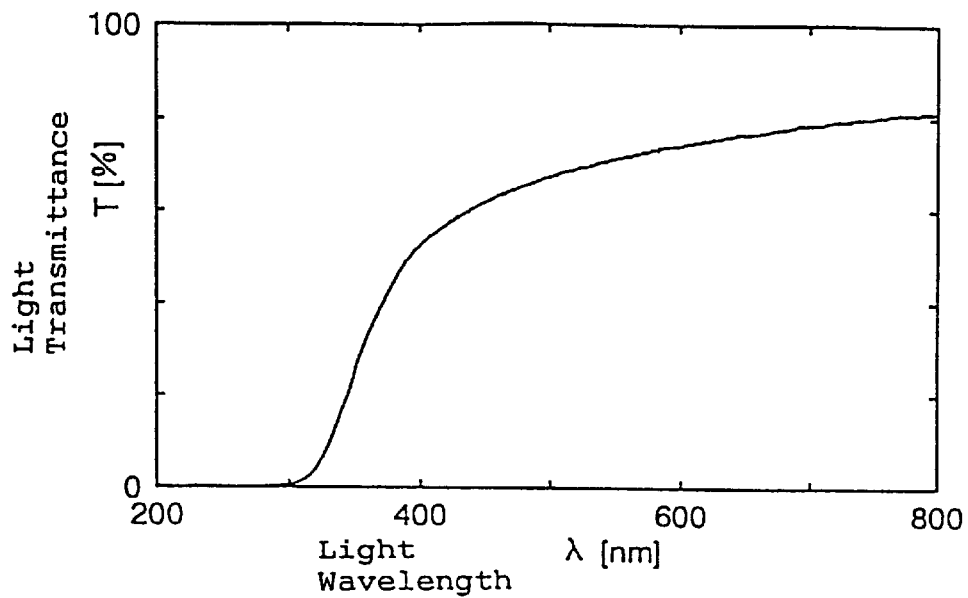
FIG. 1 is a graph showing the relationship between light wavelength and light transmittance of the ultraviolet shielding composite fine particles obtained in Example 1, as measured by an ultraviolet-visible light spectrophotometer.

Fine particles having a relatively small particle diameter and having a high shielding ability against ultraviolet light are likely to form aggregates, so that when dispersed in a medium the fine particles would not perform their shielding function well. Therefore, by the formation of a composite of the fine particles with relative large particles, namely by supporting the fine particles as daughter particles in matrix particles used as a carrier, the fine particles are maintained in a good dispersion state, thereby retaining their high shielding ability against the ultraviolet light. Further, by coating the surface of the composite fine particles with an inorganic material having substantially no catalytic activities, the catalytic activities of the composite fine particles can be substantially suppressed. Therefore, by coating the surface of the composite fine particles with an inorganic material having substantially no catalytic activities, even when the composite fine particles are subjected to a surface-improvement treatment, the treatment material used is not likely to undergo deterioration by catalytic activities or photo-catalytic activities of the composite fine particles.

Furthermore, ultraviolet shielding composite fine particles having easy handling are obtainable by the steps of subjecting the surface of the composite fine particles coated with an inorganic material to a water-repellent treatment, and then pulverizing the composite fine particles obtained after the water-repellent treatment to give a powder. Alternatively, the ultraviolet shielding composite fine particles are also obtainable by the steps of subjecting the surface of the composite fine particles to a water-repellent treatment, and then dispersing the composite fine particles in an oil agent. In the present specification, the matrix particles of the composite fine particles refer to a matrix capable of containing and supporting daughter particles dispersed therein. The matrix particles are aggregates formed while retaining the shapes of the particles constituting the matrix particles (i.e., primary particles). The daughter particles refer to particles other than the matrix particles having an ultraviolet shielding ability.

1. Preferred embodiments of the present invention will be explained in detail below by referring to the following properties of the composite fine particles: (1) band gap energy of the particles, (2) refractive index of the composite fine particles, (3) grain boundaries of the particles, and (4) coatings formed on the surface of the composite fine particles by inorganic materials (1) Band Gap Energy of Particles In the composite fine particles of the present invention, the fine particles used as the daughter particles have to have a good shielding ability against ultraviolet light. The ultraviolet shielding abilities are classified into two kinds: Absorbing ability of ultraviolet light and scattering ability of ultraviolet light.

The ultraviolet light absorption by inorganic compounds is ascribed to exciton absorption of mainly semiconductive compounds, and compounds having a band gap energy of from 3.0 to 4.0 eV effectively show such a property. Scattering of ultraviolet light is strongly exhibited as Mie scattering. In the case of high-refractive index materials, such as $TiO_2$, scattering is remarkably observed when the particle diameter of the material is about one-half the wavelength of the ultraviolet light, namely not more than 0.2 μm.

Since in ceramics the valence electron band and the conduction band are not continuous, ceramics are known to absorb light having a wavelength corresponding to an energy not less than the band gap energy, the band gap energy referring to the difference between the energy level of the valence electron band and that of the conduction band. For instance, ZnO has a band gap energy of 3.2 eV, which absorbs light having a wavelength of not more than 390 nm. The inorganic ultraviolet shielding agent absorbs ultraviolet light because its band gap energy corresponds to the wavelength of the ultraviolet light Therefore, in the composite fine particles of the present invention, in order for the daughter particles to exhibit effective scattering ability and absorption ability of ultraviolet light, the particles constituting the matrix particles must have a band gap energy larger than that of the daughter particles. For instance, in the case of using aggregates of $TiO_2$ particles (rutile-type) as the matrix particles, and ZnO fine particles having a band gap energy smaller than that of $TiO_2$ as the daughter particles, the ultraviolet light having a wavelength of not more than 320 nm is absorbed by exciton absorption corresponding to the band gap energy of the particles constituting the matrix particles, namely $TiO_2$. Also, ultraviolet light having a wavelength in the vicinity of 350 nm, which penetrates the matrix particles without being absorbed, is absorbed by exciton absorption corresponding to the band gap energy of the daughter particles while being multiply scattered by the daughter particles Accordingly, the $ZnO/TiO_2$ (daughter/matrix) composite fine particles have a shielding ability against ultraviolet light having a wavelength of not more than 350 nm.

By contrast, when $TiO_2$ is used as the particles constituting the matrix particles and $SnO_2$ fine particles having a larger band gap energy than $TiO_2$ is used as the daughter particles, the ultraviolet light having a wavelength of not more than 320 nm is absorbed by exciton absorption corresponding to the band gap energy of the $TiO_2$ particles. However, the ultraviolet light having a wavelength in the vicinity of 350 nm, which penetrates the matrix particles without being absorbed, is not absorbed by exciton absorption corresponding to a band gap energy of $SnO_2$. Accordingly, the $SnO_2/TiO_2$ (daughter/matrix) composite fine particles cannot provide sufficient shielding effects against ultraviolet light having wavelengths in the vicinity of 350 nm.

For the above reasons, in the composite fine particles of the present invention, the particles constituting the matrix particles have a band gap energy of preferably 3 to 9 eV, more preferably 5 to 9eV. In order to more securely have the ultraviolet light reach the daughter particles, the difference between the minimum band gap energy of the daughter particles and the band gap energy of the particles constituting the matrix particles is preferably not less than 0.2 eV, the ultraviolet light having wavelengths at which absorption and scattering of the ultraviolet light can be achieved by the daughter particles.

(2) Refractive Indices of Composite Fine Particles

When the ultraviolet shielding composite fine particles are actually used, it is necessary for them to exhibit high transparency in the visible light region while maintaining a high shielding ability in the ultraviolet light region. Here, (i) in order to maintain a high shielding ability, the difference between the refractive indices of the matrix particles and the daughter particles has to be kept as large as possible because the ultraviolet shielding ability is remarkably improved when the difference between the refractive indices is kept large. In the present invention, the difference between the refractive indices is preferably not less than 0.1. For this reason, in the present invention, metal oxides and fluorine compounds both having relatively low-refractive indices are used as materials constituting the matrix particles together with the daughter particles having a relatively high refractive index. Also, (ii) in order to exhibit high transparency, the difference between the refractive indices of the composite fine particles and the surrounding materials (medium) has to be kept as small as possible. Thus, the refractive index of the composite fine particles has to be controlled in order to make the difference small. The present invention is characterized by adjusting the refractive indices of the composite fine particles by controlling the volume ratios between the matrix particles and the daughter particles, and further by using a fluorine compound.

In a suspension of the composite fine particles, such as a suspension to be used for cosmetics, etc., when the refractive index of the composite fine-particles differs largely from that of the medium, transparency is likely to be lost because the visible light is refracted or reflected at the interface of the composite fine particles and the medium. Here, the refractive index may be measured by a generally known immersion method (see Toshiharu Takou, et al., Optical Measurement Handbook, p. 475, 1981, published by Asakura Publishers). In this method, the refractive index of the sample is the refractive index of a medium, whose highest light transmittance is obtained at a wavelength of 589.3 nm. However, the operating procedure for the immersion method is complicated, and time-consuming. For convenience, the refractive index can be theoretically calculated from the refractive indices of the daughter particles and the primary particles of the matrix particles and the volume ratio therebetween. Since the theoretically calculated refractive index closely approximates data obtained by the immersion method depending on the composite fine particles, the refractive indices of the composite fine particles can be also obtained by a simple calculation method as mentioned above.

The refractive index $n_D^{20}$ of the generally used medium is from 1.3 to 1.8. On the other hand, since many of metal oxides having a high ultraviolet shielding ability, such as $TiO_2$ and ZnO, have a refractive index $n_D^{20}$ of not less than 2.0, when the metal oxides are used as the daughter particles, the refractive index of the composite fine particles has to be approximated to that of the medium by using a low-refractive index material for the matrix particles. Specifically, an average refractive index of the composite fine particles is from 1.3 to 2.5, preferably from 1.3 to 2.0, more preferably from 1.3 to 1.8, particularly preferably from 1.3 to 1.7, and most preferably from 1.4 to 1.5. Also, a difference of the refractive indices between the matrix particles and the daughter particles in the composite fine particles of the present invention is preferably not less than 0.1. By keeping the difference between the refractive indices, the scattering ability of the ultraviolet light is improved.

(3) Grain Boundaries of Particles

As the particle diameter of the primary particles of the matrix particles becomes smaller, namely as the grain boundaries in the inner portion of the matrix particles become smaller, the visible light cannot detect the presence of the grain boundaries, so that the matrix particles are provided with transparency regardless of whether the primary particles of the matrix particles are crystallized. Since the daughter particles similarly comprise ultrafine particles, they also have good transparency. Therefore, the composite fine particles have an altogether good transparency.

(4) Coatings Formed on the Surface of the Composite Fine Particles by Inorganic Materials In the case of coating the surface of the composite fine particles with an inorganic material having substantially no catalytic activities in order to suppress the catalytic activities of the ultrafine particles, the formed coating layer may be either a thin layer or a thin, fine particle layer. The thickness of the coating layer is considered to be sufficient if the active sites on the surface of the composite fine particles are substantially coated so as to prevent the surface activities from affecting the surrounding medium of the composite fine particles. In other words, by substantially suppressing the surface activities of the composite fine particles, the deterioration of the medium at the surface of the composite fine particles and the medium contacting their surfaces, the media being, for instance, cosmetic base materials, paints, etc., can be prevented. Also, since the dispersant is not deteriorated, the dispersibility of the composite fine particles can be stably maintained for a long period of time. While the above are conventionally unavoidable problems in cases where inorganic, ultraviolet shielding agents are generally dispersed in various kinds of media, the present invention provides a means for solving the conventional problems.

2. Next, the method for producing the ultraviolet shielding composite fine particles of the present invention will be explained according to each of the steps described below.

The water-repellent treatment step for the composite fine particles indicated in the steps below is optional in the present invention. However, in cases where the obtained composite fine particles are incorporated in cosmetics, etc., the water-repellent treatment step is preferably included. The production methods including the water-repellent treatment step are given below as preferred embodiments of the present invention. There are two embodiments: (1) One embodiment where the composite fine particles are powdered by drying and pulverization; and (2) another embodiment where the composite fine particles are dispersed in an oil agent. Each of the embodiments (1) and (2) comprises the following steps.

(1) Embodiment Where the Composite Fine Particles are Powdered by Drying and Pulverization In this embodiment, the method for producing composite fine particles comprises the steps of:

(a) preparing a liquid mixture comprising (i) starting materials for matrix particles which are present in one or more forms selected from the group consisting of sols containing particles constituting matrix particles and powders of the matrix particles, the matrix particles having a primary particle with an average particle diameter of from 0.001 to 0.3 μm; and (ii) starting materials for daughter particles which are present in one or more forms selected from the group consisting of sols containing daughter particles and powders of the daughter particles, the daughter particles having a primary particle with an average particle diameter of from 0.001 to 0.1 μm, and treating the liquid mixture in a mill and/or an apparatus for high-pressure dispersion, to thereby produce composite fine particles wherein the daughter particles and the matrix particles are aggregated; and (b) coating the composite fine particles obtained in step (a) with an inorganic material.

In this embodiment, the following additional steps may be carried out.

(c) subjecting the composite fine particles coated with the inorganic material obtained in step (b) to a water-repellent treatment; and (d) drying and/or pulverizing the composite fine particles subjected to the water-repellent treatment obtained in step (c).

(2) Embodiment Where the Composite Fine Particles are Dispersed in an Oil Agent.

In this embodiment, the method for producing composite fine particles comprises the steps of:

(a) preparing a liquid mixture comprising (i) starting materials for matrix particles which are present in one or more forms selected from the group consisting of sols containing particles constituting matrix particles and powders of the matrix particles, the matrix particles having a primary particle with an average particle diameter of from 0.001 to 0.3 μm; and (ii) starting materials for daughter particles which are present in one or more forms selected from the group consisting of sols containing daughter particles and powders of the daughter particles, the daughter particles having a primary particle with an average particle diameter of from 0.001 to 0.1 μm, and treating the liquid mixture in a mill and/or an apparatus for high-pressure dispersion, to thereby produce composite fine particles wherein the daughter particles and the matrix particles are aggregated;

(b) coating the composite fine particles obtained in step (a) with an inorganic material;

(c) subjecting the composite fine particles coated with the inorganic material obtained in step (b) to a water-repellent treatment; and (d') dispersing in an oil agent the composite fine particles subjected to the water-repellent treatment obtained in step (c).

In the preparation of the liquid mixture in step (a) above, the powders of the daughter particles where these particles comprise ultrafine particles having an average particle diameter of from 0.001 to 0.1 μm are desirably disintegrated and/or pulverized in a mill or an apparatus for high-pressure dispersion, whereby the dispersion state of the daughter particles in the liquid mixture is maintained. Examples of mills include bead mills, sand mills, and ball mills, and examples of high-pressure dispersion devices include microfluidizers and nanomizers.

In the present invention, in the case where the daughter particles comprising the above ultrafine particles and a liquid mixture having a large proportion and high concentration of the daughter particles are subjected to a mill treatment and/or a high-pressure dispersion treatment, a pre-treatment is preferably carried out prior to the mill treatment and/or the high-pressure dispersion treatment using a dispersion device capable of disintegrating powders of the ultrafine particles, the dispersion devices including homomixers and homogenizers. The reasons for carrying out the pre-treatment are as follows. By disintegrating the powders of the ultrafine particles which are in an aggregated state at a high concentration, the load for the disintegration and/or pulverization required in subsequent treatments following the pre-treatment step, namely a mill treatment step and/or a high-pressure dispersion treatment step, is notably reduced, so that the disintegration and/or pulverization are efficiently carried out, thereby resulting in a good dispersion of the ultrafine particles.

In the coating step with the inorganic materials according to step (b), the coating methods are not particularly limited, and any of the coating methods utilized for sol-gel reaction methods and precipitation reaction methods can be employed. The inorganic materials to be used for coating are not particularly limited as long as they are inorganic materials having substantially no catalytic activity. Among them, a preference is given to metal oxides, with a particular preference being given to $SiO_2$, $Al_2O_3$, and a mixture thereof. The starting materials for the inorganic materials used in the coating step are not particularly limited, and any of the metal salts, such as metal alkoxides, metal nitrates, and metal sulfates, may be used. Specific examples of the metal salts include tetraethoxysilane, aluminum isopropoxide, aluminum tri-sec-butoxide, sodium silicates, and aluminum sulfate. By utilizing the precipitation reaction and the sol-gel reaction depending upon the properties of the above starting materials for the inorganic materials used, the surface of the composite fine particles can be coated with the inorganic materials. Incidentally, after the coating step, a neutralization reaction step may be optionally added before or after the water-repellent treatment step.

In the present specification, the "sol-gel reaction method" refers to a method comprising allowing colloidal particles contained in a sol to grow by coagulation or aggregation, thereby allowing gelation of the resulting colloidal particles to take place. In the case where the above sol-gel reaction method is utilized to coat the surface of the composite fine particles, the gelation mentioned above can be carried out on the surface of the composite fine particles. Also, the "precipitation reaction method" refers to a method comprising adding a precipitation agent to a solution containing the metal salts, to give precipitated particles. In this method, concentrations, pHs, and temperatures are suitably controlled to have the precipitated particles adhere on the surface of the composite fine particles. Examples of the precipitation reaction methods include coprecipitation methods, methods of precipitation from homogeneous solution, and compound precipitation methods.

Although the amount of the inorganic materials applied as a coating is not particularly limited, exceedingly large amounts of coating give rise to a large diameter of the composite fine particles, thereby drastically impairing the optical properties of the composite fine particles. On the other hand, too small amounts of coating lead to undesirable catalytic activities of the composite fine particles. Therefore, the amount of the inorganic materials applied as a coating has to be suitably adjusted in order not to cause such undesired effects.

In the water-repellent treatment according to step (c) above, the water-repellants and the methods for water-repellent treatment are not particularly limited, and any of the water-repellent treatment methods can be employed, including treatments with silicone compounds, such as methyl hydrogen polysiloxane, high-viscosity silicone oils, oxazoline-modified silicones, amino-modified silicones, and silicone resins; treatments with surfactants, including anionic surfactants, such as stearic acid and oleic acid, and cationic surfactants; treatments with macromolecular compounds, such as nylon, polymethylmethacrylate, polyethylene, Teflon™, and polyamino acids; treatments with perfluoro-group containing compounds, lecithin, collagen, metal soaps, lipophilic waxes, partial esters of polyhydric alcohols, and whole esters of polyhydric alcohols; and treatments with phosphate compounds, such as monoalkylphosphates and dialkylphosphates, without intending to limit the treatment methods to those listed above. In principle, electrostatic forces between the surface of the composite fine particles and the water-repellants may be employed. Also, seed condensation of the water-repellants containing the composite fine particles as a seed may be employed in a water-repellent treatment methods. Incidentally, a neutralization reaction step may be optionally added before or after the water-repellent treatment step. Although step (c) is an optional process in Embodiment (1), the coating step may be preferably carried out from the viewpoint of suppressing the surface activities and dispersing the composite fine particles.

Next, in step (d) of drying and pulverizing the composite fine particles subjected to a water-repellent treatment, the drying methods and the pulverization methods are not particularly limited. For example, drying methods such as hot-air drying and topping treatments may be employed, and in the pulverization method, sand mills and blade-type mills may be employed. The composite fine particles obtained after the pulverization step may be controlled to a given particle diameter by classification. In order to determine the particle diameter and shapes of the resulting composite fine particles or the particle diameters of the daughter particles and the matrix particles, an electron microscope may be used.

In step (d') where the composite fine particles are dispersed in an oil agent, the methods for dispersing the composite fine particles in an oil agent are not particularly limited. For instance, after mixing the oil agent and the liquid mixture dispersion containing the composite fine particles subjected to the water-repellent treatment, such treatments as a topping treatment may be carried out in the case where the solvent of the liquid mixture dispersion is volatile, as in the case of ethanol. Alternatively, after the above mixing step, conventional solvent substitution methods may be carried out in the case where the solvent is non-volatile. Incidentally, examples of the oil agents include various hydrocarbons, higher fatty acids, fats and oils, esters, higher alcohols, and waxes, such as squalane, paraffin wax, liquid paraffin, Vaseline™, microcrystalline wax, ozocerite, ceresine, myristic acid, palmitic acid, stearic acid, oleic acid, isostearic acid, cetyl alcohol, hexadecyl alcohol, oleyl alcohol, cetyl 2-ethylhexanoate, 2-ethylhexyl palmitate, 2-octyldodecyl myristate, neopentyl glycol di-2-ethylhexanoate, glycerol tri-2-ethylhexanoate, 2-octyldodecyl oleate, isopropyl myristate, glycerol triisostearate, coconut fatty acid triglyceride, olive oil, avocado oil, camellia oil, jojoba oil, beeswax, spermaceti, carnauba wax, myristyl myristate, mink oil, and lanoline; silicone oils, such as volatile silicone oils and non-volatile silicone oils. In addition, in the case where the composite fine particles surface-treated with a volatile material are dispersed in an oil agent, it is preferred that the moisture of the composite fine particles and the liquid mixture dispersion be removed in order to prevent the formation of a water and oil emulsion. Suitable methods for dehydration are reflux and topping treatments using such solvents as hexane and cyclohexane.

The concentration of the composite fine particles in the oil agent is not particularly limited, and the concentration of the composite fine particles dispersible in the oil agent is highly related to the particle diameters of the composite fine particles and the kinds of the water-repellants and the oil agents used. When the concentration of the composite fine particles is too high, the aggregation of the composite fine particles takes place in the oil agent, thereby notably deteriorating the dispersibility and the optical properties of the composite fine particles, which in turn leads to the deterioration of the properties of the oil agent. Therefore, the concentration of the composite fine particles in the oil agent has to be suitably adjusted in order avoid undesirable effects.

3. Each of the starting materials used in the production methods of the present invention will be explained in detail below.

(1) Daughter Particles

The daughter particles constituting the composite fine particles in the present invention maintain good transparency in the visible light region while having a good shielding ability in the ultraviolet light region. Therefore, the daughter particles ideally do not absorb the light in the visible light region and to have a particle diameter small enough not to scatter the visible light.

In order to satisfy the requirements of not absorbing the visible light and absorbing the ultraviolet light, the materials constituting the daughter particles preferably have a wavelength for an exciton absorption of a band gap energy corresponding to the wavelengths in the ultraviolet light region. Specifically, semiconductive compounds having a band gap energy of from 3.0 to 4.0 eV are preferred, including, for instance, $TiO_2$, ZnO, $CeO_2$, SiC, $SnO_2$, $WO_3$, $SrTiO_3$, $BaTiO_3$, and $CaTiO_3$, which characteristically exhibit the above property. Among them, $TiO_2$, ZnO, and $CeO_2$ are conventionally used as ultraviolet shielding agents, and these compounds, which are particularly preferred examples, may be used singly or in combination. In particular, in order to shield the ultraviolet light of the ultraviolet light region A (320 to 400 nm), ZnO and $CeO_2$ are effectively used. Also, in order to shield the ultraviolet light of the ultraviolet light region B (280 to 320 nm), $TiO_2$ is effectively used. Incidentally, in order to shield both the ultraviolet light of the ultraviolet light region B and that of the ultraviolet light region A, the daughter particles comprising $TiO_2$ and one or more compounds selected from the group consisting of ZnO, $CeO_2$, $BaTiO_3$, $CaTiO_3$, $SrTiO_3$, and SiC may be preferably used in combination.

Alternatively, in the case where $TiO_2$ is used, the shielding region can be extended to the ultraviolet light region A by incorporating, as impurity dopes, an element having a valence number of 5 or more, such as W, P, Ta, Nb, Sb, or Mo, or an element having a valence number of 3 or less, such as Zn, Al, Mg, and Ca.

The shapes of the daughter particles are not particularly limited, and may be spherical, plate-like or acicular. The particle diameter of the daughter particles is preferably substantially the same as that of the primary particles of the matrix particles from the viewpoint of providing good dispersion of the daughter particles in the matrix particles. Furthermore, as for the scattering ability of the light in the ultraviolet light region, which is strongly exhibited by Mie scattering, scattering can be remarkably noted when the particle diameter is about one-half the wavelength of the ultraviolet light, namely, not more than 0.2 μm. Therefore, in order to satisfy both good transparency in the visible light region and good shielding ability in the ultraviolet light region, the daughter particles have an average particle diameter of preferably not more than 0.2 μm, more preferably not more than 0.1 μm, particularly 0.001 to 0.1 μm, and more particularly not more than 0.05 $\mu$m. In the present invention, the term "daughter particles" refers to primary particles individually dispersed in and supported by the matrix particles and/or aggregates of the primary particles. Therefore, the average particle diameter of the daughter particles may also mean the average particle diameter of the aggregates.

In the present invention, the sols containing the daughter particles and the daughter particle powder are used upon production for the starting materials for the daughter particles. Since the daughter particles are present preferably in a dispersed state in the inner portion of the composite fine particles, higher dispersibility and stability of the daughter particles in a sol are desired. In order to achieve such states of the daughter particles in a sol, the surface of the daughter particles may be coated with other materials, or the daughter particles may be blended with a sol stabilizer. For instance, in the case where $TiO_2$ ultrafine particles are used as the daughter particles, the surface of the ultrafine particles may be coated with such compounds as $SiO_2$ and $Al_2O_3$ to improve dispersibility. Alternatively, the ultrafine particles may be blended with a basic stabilizer, such as $NH_3$, to stabilize the state of the $TiO_2$ sol. Also, in the case where the fine particle powder is surface-treated to achieve good dispersion, the treated fine particles can be used as starting materials for the daughter particles. The sol used in the present invention refers to fluids containing particles which cannot be generally observed by an ordinary electron microscope but having a particle diameter larger than that of an atom or that of a low molecular compound (see Iwanami Dictionary of Physics and Chemistry, Third Edition, published by Iwanami Publishers). Examples of sols include hydrosols of silica and suspensions of $TiO_2$ ultrafine particles.

(2) Matrix Particles

The matrix particles constituting the composite fine particles must have good transparency in the visible light region as must the daughter particles in order to afford good transparency to the composite fine particle suspension. Specifically, the matrix particles are desirably constituted by materials which do not absorb the visible light, and the primary particles of the matrix particles preferably do not have a particle diameter exceeding 0.3 $\mu$m. For instance, a preference is given to aggregates of the ultrafine particles, each of the ultrafine particles having an average particle diameter of 0.01 $\mu$m.

As for the materials constituting the matrix particles, materials having high transparency, such as metal oxides, fluorine compounds, and mixtures thereof, may be used. For instance, metal oxides, fluorine compounds, and mixtures thereof may be used. Since the aggregates of the fine particles normally constitute the matrix particles, the fine particles (i.e. primary particles) constituting the aggregates have an average particle diameter of not more than 0.3 $\mu$m, specifically, from 0.001 to 0.3 $\mu$m, in order to satisfy the requirements for the matrix particles as mentioned above. A preference is given to particles having an average particle diameter of not more than 0.15 $\mu$m, more preferably not more than 0.1 $\mu$m, particularly preferably not more than 0.05 $\mu$m. Sols containing particles constituting the matrix particles and matrix particle powder are used for the starting materials for the matrix particles. For the same reasons as mentioned in connection with the daughter particles, the surface of the particles constituting the matrix particles may be coated with other materials, or the fine particles may be blended with sol stabilizers. Here, the coating materials or the stabilizers used may be similar to those used for the daughter particles.

Many of the metal oxides are available in the form of chemically stable solids, so that the metal oxides can be suitably used for materials constituting the matrix particles. Examples of the metal oxides contained in the matrix particles include $TiO_2$, $CuO$, $ZnO$, $MgO$, $CeO_2$, $SnO_2$, $SiO_2$, $Fe_2O_3$, $Al_2O_3$, $NiO_2$, and $MnO_2$. A preference is given to $SiO_2$ and $Al_2O_3$ because of having a suitable refractive index and good transparency as explained above. Also, a preference is given to fine particles of $SnO_2$, $In_2O_3$, $SiO_2$, $ZnO$, and $Al_2O_3$ from the viewpoint of using ceramic fine particles having large band gap energies.

Many of the fluorine compounds are chemically stable and have a low refractive index, so that the compounds are highly useful for controlling the refractive index of the resulting composite fine particles. The fluorine compounds include all those present in solid or liquid state at room temperature. Examples of such solid inorganic fluorine compounds include $MgF_2$, $CaF_2$, $AlF_3$, $LiF$, $NiF_2$, and $BaF_2$. Examples of solid organic fluorine compounds include fluororesins, such as polytetrafluoroethylene (hereinafter simply abbreviated as "PTFE"), a tetrafluoroethylene-hexafluoropropylene copolymer, a tetrafluoroethylene-ethylene copolymer, vinylidene polyfluoride, and vinyl polyfluoride. Among them, $MgF_2$, polytetrafluoroethylene, and a mixture thereof are suitably used as fluorine compounds because of the suitable refractive index and good transparency of the resulting composite fine particles.

The average particle diameter of the fluorine compounds in solid state at room temperature is preferably not more than 0.3 $\mu$m, more preferably not more than 0.2 $\mu$m. The reason therefor is that when the average particle diameter exceeds 0.3 $\mu$m, the aggregating forces among the particles become weak, thereby lowering the strength of the composite fine particles.

Examples of liquid fluorine compounds at room temperature include perfluoropolyethers (hereinafter simple abbreviated as "PFPE"). An example of PFPE may be perfluoropolymethylisopropylether (for instance, "FOMBLIN HC", manufactured by Nikko Chemicals K.K.). PFPE is useful not only for lowering the refractive index of the composite fine particles but also for providing moisture with smooth skin texture, so that the PFPE is highly suitable as fine particles for use in cosmetics. When the liquid fluorine compounds are used, the solvents used may be properly chosen in order not to cause phase separation of the daughter particle starting materials and the matrix particle starting materials in the solvent. However, when the solvent is water, an emulsion comprising liquid fluorine compounds at room temperature which are emulsified by various kinds of surfactants may be preferably used. For instance, an emulsion of perfluoropolyether (oil-in-water type) may be used. The emulsion diameter is preferably of a size not exceeding 0.1 times that of droplets. When the emulsion diameter exceeds 0.1 times that of the droplets, the emulsion becomes larger than the produced particles, and thereby the production of particles becomes difficult.

In the present invention, the liquid fluorine compounds may be also used as materials having low refractive indices as explained above. In this case, the liquid fluorine compounds may be used together with the metal oxides and/or the solid fluorine compounds in order to increase freedom in the refractive index control.

Regarding suitable combinations of the daughter particles and the matrix particles of the present invention, a preference is given to the combinations where the daughter particles are selected from $TiO_2$, $ZnO$, and a mixture thereof; the matrix particles are selected from $SiO_2$, $Al_2O_3$, and a mixture thereof, and a mixture of $SiO_2$ with perfluoropolyether; inorganic material coatings are selected from $SiO_2$, $Al_2O_3$, and a mixture thereof; and water repellants are one or more compounds selected from methyl hydrogen polysiloxane, oxazoline-modified silicones, amino-modified silicones, stearic acid, monoalkylphosphates, and dialkylphosphates, from the viewpoints of providing safety and stability of the resulting ultraviolet shielding agents In the present invention, materials other than the metal oxides and the fluorine compounds mentioned above may be included in the daughter particles and the matrix particles. For example, in the case where the composite fine particles are produced by stabilizers of the starting material sol or a coating agent for sol particles, etc. may be contained in the matrix particles as long as the optical properties of the composite fine particles are not impaired.

4. The preparation of the starting material liquid mixture using the starting materials mentioned above and the method for producing the composite fine particles will be explained in more detail below.

When the liquid mixture of the starting materials is prepared, it is important to uniformly disperse and blend the liquid mixture containing the starting materials for the daughter particles and the starting materials for the matrix particles, so as to easily disperse the daughter particles in the matrix particles. By thoroughly blending the starting materials for the daughter particles and the starting materials for the matrix particles to achieve a high dispersion of the daughter particles in the matrix particles, the daughter particles can be present on the surface of and/or in the inner portions of the matrix particles. At this time, fine particles comprising starting materials of daughter particles and those of matrix particles are gathered by electrostatic forces, to give aggregated composite fine particles.

For instance, in the case where $TiO_2$ ultrafine particle powder is used as the starting material for the daughter particles and an $SiO_2$ sol (aqueous; "ST-C," manufactured by Nissan Chemical Industries, Ltd.; pH 8.5 to 9.0) is used as the starting materials for the matrix particles, and the above starting materials are subjected to a treatment in a mill or a high-pressure dispersion device at appropriate conditions and the pH of the resulting liquid mixture is adjusted to 7, $TiO_2$ with an isoelectric point of pH of about 5 to 7 is negatively charged on account of its isoelectric point, and $SiO_2$ forms an electric double layer whose surface is positively charged, so that composite fine particles are formed by aggregation of the daughter particles and the matrix particles by electrostatic forces generated between the $TiO_2$ daughter particles and the $SiO_2$ matrix particles. Also, in another case where ZnO ultrafine particle powder is used as the starting material for the daughter particles and an $SiO_2$ sol (aqueous; "ST-C," manufactured by Nissan Chemical Industries, Ltd.; pH 8.5 to 9.0) is used as the starting materials for the matrix particles, and where the above starting materials are subjected to a treatment in a mill or a high-pressure dispersion device at appropriate conditions while the pH of the resulting liquid mixture is adjusted to 7, ZnO with an isoelectric point of pH of about 9.3 is positively charged on account of its isoelectric point, and $SiO_2$ forms an electric double layer whose surface is positively charged. Observations made by a transmission electron microscope resulted in the finding that composite fine particles are formed by aggregation of ZnO daughter particles and $SiO_2$ matrix particles. Incidentally, when the composite fine particles are formed, a slidable surface in the electric double layer of $SiO_2$ is presumably cracked whereby the surface is negatively charged, and the negatively charged surface contacts the ZnO daughter particles.

The $SiO_2$ sols which are used in the above examples have the following functions:

(1) they act as a medium for efficiently disintegrating daughter particles which are normally present in an aggregated state to about the size of the particle diameter of the primary particles and/or as a medium for pulverizing the daughter particles to a size not greater the particle diameter of the primary particles;

(2) they form a basic structure in which the daughter particles adhere to the matrix particles simultaneously with the disintegration and/or pulverization; and (3) they act as a dispersant for inhibiting the aggregation of the composite fine particles with each other by electrostatic repulsion of $SiO_2$ on the surface of the composite fine particles after formation of the composite fine particles.

The particle diameter of the $SiO_2$ sol may be suitably chosen according to functions (1) to (3) described above. For instance, in the case where function (3) is considered to be very important, the particle diameter of the $SiO_2$ sol is preferably about the same size as or less than the particle diameter of the daughter particles. Specifically, the particle diameter of the $SiO_2$ sol is suitably not more than 0.1 $\mu$m, preferably not more than 0.05 $\mu$m, more preferably not more than 0.02 $\mu$m. Incidentally, the solvents used for the $SiO_2$ sol include hydrosols (aqueous) and organosols, which may be suitably selected taking into consideration the kinds of the daughter particles and the dispersion stability.

According to the methods described above, the composite fine particles comprising aggregates of the daughter particles and the matrix particles are formed, and in order to firmly maintain the aggregated state of the composite fine particles and to have substantially no catalytic activities by the daughter particles, the surface of the composite fine particles is coated with the inorganic materials having substantially no catalytic activities. As explained above, the coating layer may be either a thin layer or a thin, fine particle layer. As for the thickness of the coating layer, thickness is considered to be sufficient if the active sites on the surface of the composite fine particles are substantially coated so as not to have the surface actions affect the surrounding medium of the composite fine particles.

Suitable solvents for the starting materials for the daughter particles and the starting materials for the matrix particles mentioned above are any aqueous or organic solvents, which do not inhibit the production of the composite fine particles comprising the daughter particles/matrix particles composite in the starting material liquid mixture. Examples of the organic solvents include alcohols, such as methanol and ethanol, and polar solvents, such as N,N-dimethylformamide, dimethyl sulfoxide, hexamethylphosphoramide, and ethyl acetate. As long as the formation of the ultraviolet shielding composite fine particles is not adversely affected, the solvents for the metal oxide sol solutions mentioned above or different ones may be used.

The concentration of the starting materials for the matrix particles in the starting material liquid mixture containing the starting materials for the daughter particles and the starting materials for the matrix particles is preferably in the range of from $10^{-5}$ to 10 mol/L, more preferably from $10^{-4}$ to 1 mol/L. Specifically, the concentration of the starting materials for the matrix particles is preferably not less than $10^{-5}$ mol/L, from the viewpoint of maintaining the daughter particles well dispersed in the composite fine particles, and the concentration is preferably not more than 10 mol/L, from the viewpoint of maintaining the starting material of the matrix particles and the daughter particles well dispersed in the starting material liquid mixture.

When a fluorine compound is used as a starting material for the matrix particles, the concentration of the fluorine compound in the starting material liquid mixture containing the starting materials for the daughter particles and the starting materials for the matrix particles is preferably in the range of from $10^{-5}$ to 10 mol/L, more preferably from $10^{-4}$ to 1 mol/L. Specifically, the concentration of the fluorine compound is preferably not less than $10^{-5}$ mol/L, from the viewpoint of producing an effective amount of the fluorine compound fine particles, and the concentration is preferably not more than 10 mol/L, from the viewpoint of the solubility of the fluorine compound.

The concentration of the starting materials for the daughter particles in the starting material liquid mixture containing the starting materials for the daughter particles and the starting materials for the matrix particles is preferably in the range of from $10^{-5}$ to 10 mol/L, more preferably from $10^{-4}$ to 1 mol/L. Specifically, the concentration of the daughter particles is preferably not less than $10^{-5}$ mol/L, from the viewpoint of providing the minimum amount necessary to achieve good optical properties of the daughter particles in the composite fine particles, and the concentration is preferably not higher than 10 mol/L, from the viewpoint of sufficiently dispersing the starting materials for the daughter particles in the liquid mixture, whereby the composite fine particles having a uniform composition are produced.

The amount of the daughter particles dispersed in and supported by the matrix particles is not particularly limited as long as the daughter particles can be well dispersed in the matrix particles without causing an excessive aggregation of the daughter particles in the matrix particles. The amount of the daughter particles contained in the matrix particles normally ranges from 0.1 to 85% by volume, preferably from 0.1 to 50% by volume, more preferably from 0.1 to 30% by volume, particularly preferably from 0.5 to 20% by volume. In the case where the composite fine particles are coated with the inorganic materials, the amount of the inorganic material coating is subtracted when calculating the amount of the daughter particles. In the case where the metal oxides and the fluorine compounds are contained in the matrix particles, the minimum amount of the fluorine compounds is not less than 1% by weight, based on the composite fine particles. The amount of the daughter particles is calculated by the density of the materials constituting the composite fine particles (in the case of particles, the particle density) and the compositional ratio of the starting material liquid mixture.

The concentration of the starting materials for the inorganic materials in the starting material liquid mixture containing the composite fine particles comprising the daughter particles and the matrix particles is preferably in the range of from $10^{-5}$ to 10 mol/L, more preferably from $10^{-4}$ to 1 mol/L, when the concentration of the composite fine particles is in the range of from $10^{-5}$ to 10 mol/L. Specifically, the concentration of the inorganic materials is preferably not less than $10^{-5}$ mol/L, from the viewpoint of coating the surface of the composite fine particles to an extent sufficient for providing good coating effects. The concentration is preferably not higher than 10 mol/L, from the viewpoint of the solubility of the starting materials for the inorganic materials.

The composite fine particles, which are coated with the inorganic materials, and comprise the daughter particles and the matrix particles dispersed in the liquid mixture, have an average particle diameter of preferably from 0.002 to 0.5 $\mu$m, specifically not greater than 0.4 $\mu$m, particularly not greater than 0.3 $\mu$m, furthermore not greater than 0.2 $\mu$m, and the particle diameter distribution should preferably be kept as narrow as possible. When the average particle diameter exceeds 0.5 $\mu$m, transparency and the ultraviolet shielding ability are likely to be lowered due to the scattering of the visible light caused by the large particle diameter. On the other hand, when the average particle diameter is not greater than 0.5 $\mu$m, and even if the difference between the refractive index of the composite fine particles and that of the dispersion medium were large, the transparency of the composite fine particles can be maintained at a high level without scattering of the visible light. The average particle diameter mentioned herein is measured by dispersing a cake comprising the composite fine particles after the coating treatment in water and obtaining a particle diameter using a particle size analyzer (for example, a laser doppler-type particle size analyzer "DLS-700," manufactured by OTSUKA ELECTRONICS CO., LTD.).

The ultraviolet shielding composite fine particles of the present invention can be obtained by the production method explained above, and the structure of the ultraviolet shielding composite fine particles is such that the matrix particles comprise aggregates of primary particles which are formed while the primary particles retain their shapes, each primary particle being aggregated in a close-packed state, and that the daughter particles are dispersed on the surface and in the inner portion of the matrix particles, the composite fine particles comprising the daughter particles and the matrix particles being preferably coated with an inorganic material having substantially no catalytic activities. When the dispersibility of the daughter particles is poor, they do not show good optical properties. When the daughter particles are present on the surface of the matrix particles, the ultraviolet light which collides with the daughter particles is partially absorbed while the remaining ultraviolet light is scattered from the composite fine particles. The ultraviolet light which does not collide with the daughter particles on the surface and further enters the inner portion of the matrix particles is absorbed and scattered by the daughter particles contained in the inner portion of the matrix particles, so that the ultraviolet light is effectively shielded. Also, because the coating layer comprises the inorganic materials, the catalytic activities of the daughter particles and the matrix particles are substantially inhibited, so that the composite fine particles can be stably present in a given medium without causing a deterioration of the medium.

The shapes and the sizes of the final product of the composite fine particle powders of the present invention obtainable after the drying and pulverization step (d) above are not particularly limited, and various shapes and sizes can be used according to different cases. For instance, when used as cosmetic powders, spherical particle powders having a particle diameter ranging from sub-microns to several micrometers are preferably used from the viewpoints of a good sense of touch and easy handling, and the plate-like particle powders having the particle diameter ranges given above are preferably used from the viewpoints of providing strong adherence to the skin, excellent spreading on the skin, and easy handling.

5. Optical Properties of Composite Fine Particles

The optical properties of the ultraviolet shielding composite fine particles of the present invention can be quantitatively evaluated by measuring their light transmittance by an ultraviolet-visible light spectrophotometer.

The preferred ultraviolet shielding ability for the ultraviolet shielding composite fine particles of the present invention is determined by a light transmittance of not less than 80% at a wavelength of 800 nm, a light transmittance of not less than 20% at a wavelength of 400 nm, and a light transmittance of not more than 5% at least at one wavelength within the range from 380 nm to 300 nm. The light transmittance is determined by suspending the composite fine particles in a medium having substantially the same refractive index level as the composite fine particles, and measuring with an ultraviolet-visible light spectrophotometer using an optical cell having an optical path length of 1 mm. By having the above optical properties, a high light transmittance particularly in the visible light region as well as a high shielding ability in the ultraviolet light region can be satisfactorily achieved. Here, the phrase "a light transmittance of not more than 5% at least at one wavelength within the range from 380 nm to 300 nm" means that the light transmittance is not more than 5% at least at certain wavelengths within the range of 380 nm to 300 nm, including cases where the light transmittance exceeds 5% in certain other ranges within wavelengths of 380 nm to 300 nm. Incidentally, the phrase "a medium having substantially the same refractive index level as the composite fine particles" means that the difference in the refractive indices between a sample of the composite fine particles and the medium is within ±0.1, preferably within ±0.05. In this case, the concentration of the composite fine particles dispersed in the medium is, for instance, not less than 0.1% by weight.

The ultraviolet shielding ability mentioned above can be evaluated by an ultraviolet-visible light spectroscopy specified below.

The composite fine particles of the present invention are suspended in a medium having substantially the same refractive index level as the composite fine particles to prepare a suspension of composite fine particles having a given concentration. In order to prepare a uniform suspension, the composite fine particles are stirred and well dispersed using, for instance, an ultrasonic disperser, etc. An optical cell having an optical path length of 1 mm is filled with the above suspension. An optical cell used herein has no absorption or produces no scattering of the light in the ultraviolet light region and the visible light region, and, for instance, a silica cell can be used therefor. The light transmittance through the optical cell is measured using an ultraviolet-visible light spectrophotometer. In this method, the other optical cell filled with a medium without suspending the composite fine particles is used as a control to remove background.

Also, the composite fine particles of the present invention have substantially no catalytic activities, which may be verified by the following method. Specifically, the composite fine particles are dispersed in white vaseline in an amount of 1% by weight, and the resulting mixture is subjected to a 60-minute irradiation treatment with ultraviolet light having a central wavelength of 312 nm using an ultraviolet light source ("ENB-260C/J," manufactured by SPECTRONICS CORPORATION), to determine whether or not discoloration of white vaseline takes place in the resulting mixture by the irradiation treatment mentioned above. In the case where the white vaseline is affected by the catalytic activities, a color change undergoes of from white to brown, and thus is easily verified by the above method.

Accordingly, in the present specification, the phrase "the composite fine particles having substantially no catalytic activities" refers to the composite fine particles whose catalytic activities are inhibited to such an extent that for practical purposes they show substantially no catalytic activities For instance, when the catalytic activities are tested by the above method, the color change of the vaseline is not found.

6. Cosmetics

The cosmetics of the present invention may be prepared by optionally blending various kinds of adjuncts conventionally used for cosmetics and the dispersion oil agents used as a medium for dispersing the ultraviolet shielding composite fine particles, in addition to the above ultraviolet shielding composite fine particles. Examples of the cosmetic adjuncts are given below.

(1) Inorganic powders such as talc, kaolin, sericite, muscovite, phlogopite, lepidolite, biotite, synthetic golden mica, vermiculite, magnesium carbonate, calcium carbonate, diatomateous earth, magnesium silicate, calcium silicate, aluminum silicate, barium silicate, barium sulfate, strontium silicate, metallic tungustates, silica, hydroxylapatite, zeolite, boron nitride, and ceramic powders.

(2) Organic powders such as nylon powders, polyethylene powders, polystyrene powders, benzoguanamine resin powders, polytetrafluoroethylene powders, distyrenebenzene polymer powders, epoxy resin powders, acrylic resin powders, and fine crystalline cellulose.

(3) Inorganic white pigments such as titanium oxide and zinc oxide; inorganic red pigments such as iron oxide (red oxide) and iron titanate; inorganic brown pigments such as γ-iron oxide; inorganic yellow pigments such as yellow iron oxide and yellow ochre; inorganic black pigments such as black iron oxide and carbon black; inorganic violet pigments such as manganese violet and cobalt violet; inorganic green pigments such as chromium oxide, chromium hydroxide, and cobalt titanate; inorganic blue pigments such as ultramarine and Prussian blue; pearl-like pigments such as mica coated with titanium oxide, oxychlorobismuth coated with titanium oxide, oxychlorobismuth, talc coated with titanium oxide, fish scale flake, mica coated with colored titanium oxide; and metal powder pigments such as aluminum powders and copper powders.

(4) Organic pigments including Pigment Red 57-1, Pigment Red 57, Pigment Red 53 (Ba), Pigment Red 49 (Na), Pigment Red 63 (Ca), Vat Red 1, Pigment Red 4, Pigment Red 48, Pigment Orange 5, Pigment Orange 13, Pigment Yellow 12, Pigment Yellow 1, and Pigment Blue 15; organic pigments including zirconium lakes, barium lakes, and aluminum lakes of Acid Red 51, Acid Red 92, Acid Red 52, Acid Red 33, Acid Red 87, Acid Violet 9, Solvent Orange 7, Acid Orange 7, Acid Yellow 23, Acid Yellow 5, Acid Yellow 73, Acid Yellow 3, Food Green 3, and Food Blue 1.

(5) Natural pigments such as chlorophyll and β-carotene (6) Various hydrocarbons, higher fatty acids, fats and oils, esters, higher alcohols, and waxes, such as squalane, paraffin wax, liquid paraffin, Vaseline™, microcrystalline wax, ozocerite, ceresine, myristic acid, palmitic acid, stearic acid, oleic acid, isostearic acid, cetyl alcohol, hexadecyl alcohol, oleyl alcohol, cetyl 2-ethylhexanoate, 2-ethylhexyl palmitate, 2-octyldodecyl myristate, neopentyl glycol di-2-ethylhexanoate, glycerol tri-2-ethylhexanoate, 2-octyldodecyl oleate, isopropyl myristate, glycerol triisostearate, coconut fatty acid triglyceride, olive oil, avocado oil, camellia oil, jojoba oil, beeswax, spermaceti, carnauba wax, myristyl myristate, mink oil, and lanoline; silicone oils such as volatile silicone oils and non-volatile silicone oils.

(7) The ultraviolet protecting agents such as ultraviolet light absorbents may be optionally added, if necessary. Examples of the ultraviolet light absorbents include the following:

1) Benzoic acid derivatives:

p-Aminobenzoic acid (PABA), glycerol mono-p-aminobenzoate, ethyl p-N,N-dipropoxyaminobenzoate, ethyl p-N,N-diethoxyaminobenzoate, ethyl p-N,N-dimethylaminobenzoate, butyl p-N,N-dimethylaminobenzoate, amyl p-N,N-dimethylaminobenzoate, and octyl p-N,N-dimethylaminobenzoate.

2) Anthranilic acid derivatives:
Homomenthyl N-acetylanthranilate.

3) Salicylic acid derivatives:
Amyl salicylate, menthyl salicylate, homomenthyl salicylate, octyl salicylate, phenyl salicylate, benzyl salicylate, and p-isopropanolphenyl salicylate.

4) Cinnamic acid derivatives:
Octylcinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, and glycerol mono-2-ethylhexanoyl-diparamethoxycinnamate.

5) Benzophenone derivatives:
2,4-Dihydroxybenzophenone, 2,2'-dihydroxy 4-methoxybenzophenone, 2,2'-dihydroxy 4,4'-dimethoxybenzophenone, 2,2',4,4'-tetrahydroxy benzophenone, 2-hydroxy 4-methoxybenzophenone, 2-hydroxy 4-methoxy-4'-methylbenzophenone, 2-hydroxy 4-methoxybenzophenone-5-sulfonate, 4-phenylbenzophenone, 2-ethylhexyl 4'-phenylbenzophenone-2-carboxylate, 2-hydroxy 4-n-octoxybenzophenone, and 4-hydroxy 3-carboxybenzophenone.

6) Other ultraviolet absorbents:
3-(4'-Methylbenzylidene) d,l-camphor, 3-benzylidene d,l-camphor, urocanic acid, ethyl urocanate, 2-phenyl 5-methylbenzoxazole, 2,2'-hydroxy 5-methylphenylbenzotriazole, 2-(2'-hydroxy-5' t-octylphenyl)benzotriazole, dibenzarsine, dianisoylmethane, 4-methoxy 4'-t-butyldibenzoylmethane, 5-(3,3'-dimethyl-2-norbornylidene)-3-pentane-2-one, and 1-(3,4-dimethoxyphenyl)-4,4'-dimethyl-1,3-pentadione.

(8) Also, surfactants may be optionally used.
Examples of the surfactants include polyoxyethylene alkyl ethers, polyoxyethylene fatty acid esters, polyoxyethylene sorbitan fatty acid esters, polyoxyethylene sorbitol fatty acid esters, alkyl polyoxyethylene hardened castor oil sulfates, alkyl polyoxyethylene sulfates, alkyl phosphates, alkyl polyoxyethylene phosphates, alkali metal salts of fatty acids, sorbitan fatty acid esters, glycerol fatty acid esters, and silicone-based surfactants, such as polyether-modified silicones.

(9) Further, water-soluble polyhydric alcohols may be optionally used. Examples of the water-soluble polyhydric alcohols are water-soluble polyhydric alcohols having two or more hydroxyl groups in a molecule, including ethylene glycol, propylene glycol, 1,3-butylene glycol, 1,4-butylene glycol, dipropylene glycol, glycerol, polyglycerols, such as diglycerol, triglycerol, and tetraglycerol, glucose, maltose, maltitol, sucrose, fructose, xylitol, sorbitol, maltotriose, threitol, erythritol, and sugar alcohol derived from decomposed starch.

(10) In addition, other cosmetic adjuncts may be optionally added, including amino acids, such as lysine and arginine; organic acids, such as lactic acid, citric acid, succinic acid, and glycolic acid, and organic salts thereof; resins, such as alkyd resins and urea resins; plasticizers, such as camphor and tributyl citrate; antioxidants, such as α-tocopherol; antiseptics, such as butyl p-hydroxybenzoate and methyl p-hydroxybenzoate; extracts from plants, such as cornflower, althea, and *Hypericuor erectum*; bioactive substances such as retinol and allantoin; binders such as xanthan gum and carrageenan; and perfumes.

In order to improve the sense of touch and enjoy the continuality of the ultraviolet shielding effects, one or more silicone oils and ether-modified silicones may be incorporated in the cosmetics of the present invention.

The silicones are not particularly limited as long as they are those normally incorporated in cosmetics. Examples thereof include octamethyl polysiloxane, tetradecamethyl polysiloxane, methyl polysiloxane, high-molecular methyl polysiloxane, methylphenyl polysiloxane, octamethyl cyclotetrasiloxane, decamethyl cyclopentasiloxane, trimethylsiloxysilicate, and organopolysiloxanes having a repeating unit represented by the general formula (1) or the general formula (2) given below:

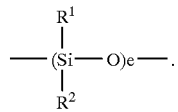

(1)

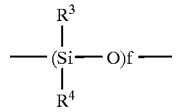

(2)

wherein $R^1$ and $R^2$, which may be identical or different, independently stand for an alkyl group having 1 to 4 carbon atoms; $R^3$ stands for a linear, branched, or cyclic alkyl group, a linear, branched, or cyclic alkenyl group, or a linear, branched, or cyclic fluoroalkyl group, each having 1 to 40 carbon atoms; "e" stands for a number of not less than 2, and "f" stands for a number of not less than 3, wherein the sum of "e" and "f" is a number 5 to 6,000.

The amount of the silicone oils given above is from 2 to 80% by weight, preferably from 5 to 50% by weight, more preferably from 8 to 40% by weight in the cosmetic composition.

The ether-modified silicones are not particularly limited as long as they are compounds in which at least a part of the siloxane is substituted by one or more groups having an ether bond. Examples thereof are given below, which may be used singly or in a combination of two or more kinds.

Specific examples of the ether-modified silicones include the following compounds (1) to (4):

[1] The ether-modified silicones having the following genera formula (3):

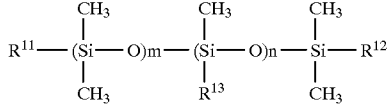

(3)

wherein at least one of $R^{11}$, $R^{12}$, and $R^{13}$ stands for a group having the general formula $R^{14}(OC_3H_6)_b(OC_2H_4)_aO(CH_2)_p$—, wherein $R^{14}$ stands for a hydrogen atom or an alkyl group having 1 to 12 carbon atoms; "a" and "b" independently stand for a number of from 0 to 35, "a" and "b" being average values; and p stands for a number of from 1 to 5, and the remaining $R^{11}$, $R^{12}$, and $R^{13}$ excluding those defined above each stands for a methyl group; "m" stands for a number of from 1 to 200, and "n" stands for a number of from 0 to 50, "m" and "n" being average values.

Among the ether-modified silicones defined in [1] above, a preference is given to those having a molecular weight of from 2,000 to 50,000 where the amount occupied by substituents $R^{11}$ to $R^{13}$ is from 5 to 40% Further, in the general formula (3), a preference given to the ether-modified silicones defined in [1] above wherein "m" is from 5 to 80, "n" is from 0 to 2, "a" is from 9 to 10, "b" is equal to 0, "p" is equal to 3, and $R^{14}$ stands for a hydrogen atom, or the ether-modified silicones defined in [1] above wherein "m" is from 90 to 110, "n" is equal to 0, "a" is from 11 to 13, "b" is equal to 0, "p" is equal to 3, and $R^{14}$ stands for a hydrogen atom.

Specific examples of the ether-modified silicones having the general formula (3) above include a commercially available product "SH-3775 Series" manufactured by Toray-Dow Corning Corporation.

[2] The polyether-alkyl-modified silicones having the following general formula (4):

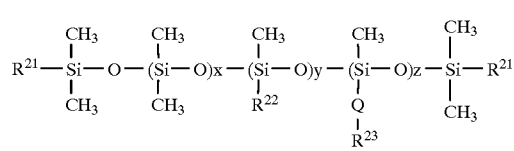

(4)

wherein $R^{21}$ stands for a hydrocarbon group having 1 to 5 carbon atoms, $R^{22}$ stands for a hydrocarbon group having 6 to 16 carbon atoms, Q stands for an alkylene group, $R^{23}$ stands for a group having the general formula —$(OC_2H_4)_q$—$(OC_3H_6)_r$—$OR^{24}$, wherein $R^{24}$ stands for a hydrogen atom or a lower alkyl group, "q" and "r" each stands for a number satisfying the relationship of $q \leq r$, wherein the molecular weight of a —$(OC_2H_4)_q$—$(OC_3H_6)_r$— moiety is from 600 to 3,500; z stands for a number of from 1 to 3; x and y each stands for a number satisfying the relationships of x<3y and x+y+z=30 to 400, with proviso that the entire weight of the —$(OC_2H_4)_q$—$(OC_3H_6)_r$— moiety does not exceed one-third of the entire weight of the polyether-alkyl-modified silicone.

The hydrocarbon groups having 1 to 5 carbon atoms represented by $R^{21}$ in the general formula (4) include alkyl groups and alkenyl groups having 1 to 5 carbon atoms. Examples thereof include a methyl group, an ethyl group, a propyl group, an isopropyl group, a butyl group, a pentyl group, or a vinyl group, among which a preference is given to a methyl group. In addition, examples of the hydrocarbon groups having 6 to 16 carbon atoms represented by $R^{22}$ include linear alkyl groups, such as a hexyl group, a heptyl group, an octyl group, a nonyl group, a decyl group, an undecyl group, a dodecyl group, a tetradodecyl group, a hexadecyl group; branched alkyl groups, such as an isooctyl group, an s-octyl group, and a 2-ethylhexyl group, among which a preference is given to a dodecyl group. Incidentally, in the case where y is greater than 1, $R^{22}$ may be identical or different for each of the repeating units.

Examples of the alkylene groups represented by Q in the general formula (4) include a methylene group, an ethylene group, a propylene group, a trimethylene group, and a tetramethylene group, among which a preference is given to a propylene group and a trimethylene group.

In the general formula (4), $R^{24}$, which is a group included in a group represented by $R^{23}$, stands for a hydrogen atom or a lower alkyl group, such as a methyl group, an ethyl group, a propyl group, an isopropyl group, or a butyl group, among which a preference is given to a hydrogen atom. In addition, preferred values of "q" and "r" are q=15 and r=0; or q=r=25; or q=29 and r=7.

Specific examples of the polyether-alkyl-modified silicones having the general formula (4) include "DC Q2-2500," manufactured by Toray-Dow Corning Corporation (laurylmethycone copolyol, wherein $R^{21}$ stands for a methyl group, $R^{22}$ stands for a dodecyl group, and x is equal to 0 in the general formula (4).

[3] The alkylglycerylether-modified silicones having the following general formula (5):

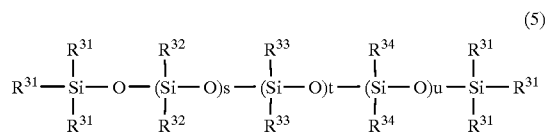

(5)

wherein at least one of $R^{31}$, $R^{32}$, $R^{33}$, and $R^{34}$ stands for a group having the general formula (6) —A—$OCH_2CH(OR^{41})CH_2OR^{42}$, wherein A stands for a divalent hydrocarbon group having 3 to 20 carbon atoms; and $R^{41}$ and $R^{42}$ each independently stands for a hydrogen atom or a hydrocarbon group having 1 to 5 carbon atoms, with proviso that at least one of $R^{41}$ and $R^{42}$ is a hydrogen atom; the remaining $R^{31}$, $R^{32}$, $R^{33}$, and $R^{34}$ excluding those defined above each stands for a linear, branched, or cyclic hydrocarbon group having 1 to 30 carbon atoms, or a group having the general formula -$BR^{43}$, wherein B stands for a divalent hydrocarbon group having an ether bond and/or an ester bond; $R^{43}$ stands for a linear, branched, or cyclic hydrocarbon group having 1 to 30 carbon atoms; "s", "t", and "u" each independently stands for a number of from 0 to 200, and when s+t+u=0, one or more $R^{31}$ groups stand for a group having the general formula (6) defined above, excluding the case where at least one of $R^{31}$ having the general formula (6) is such that A stands for a trimethylene group, each of $R^{41}$ and $R^{42}$ stands for a hydrogen atom; and each of the remaining substituents $R^{31}$, $R^{32}$, $R^{33}$, and $R^{34}$ which is not defined above stands for a methyl group.

Examples of the divalent hydrocarbon groups having 3 to 20 carbon atoms represented by A in the general formula (5) above include linear alkylene groups, such as a trimethylene group, a tetramethylene group, a pentamethylene group, a hexamethylene group, a heptamethylene group, an octamethylene group, a nonamethylene group, a decamethylene group, an undecamethylene group, a dodecamethylene group, a tetradecamethylene group, a hexadecamethylene group, and an octadecamethylene group; and branched alkylene groups, such as a propylene group, a 2-methyltrimethylene group, a 2-methyltetramethylene group, a 2-methylpentamethylene group, and a 3-pentamethylene group. Examples of the hydrocarbon groups having 1 to 5 carbon atoms represented by $R^{41}$ and $R^{42}$ include linear, branched, or cyclic alkyl groups, such as a methyl group, an ethyl group, a propyl group, an isopropyl group, a butyl group, a pentyl group, an s-butyl group, a t-butyl group, a neopentyl group, and a cyclopentyl group. Further, examples of the divalent hydrocarbon groups having an ether bond and/or an ester bond represented by B include groups having the following general formulas: —$(CH_2)_h$—$(OC_2H_4)_i$—$(OC_3H_6)_j$—O—, —$(CH_2)_h$—O—CO—, and —$(CH_2)_h$—COO—, wherein "h" stands for an integer of from 3 to 20, and "i" and "j" independently represents a number of from 0 to 50.

In addition, examples of the linear, branched, or cyclic hydrocarbon groups having 1 to 30 carbon atoms represented by $R^{43}$ include linear alkyl groups, such as a methyl group, an ethyl group, a propyl group, a butyl group, a pentyl group, a hexyl group, a heptyl group, an octyl group, a nonyl group, a decyl group, an undecyl group, a dodecyl group, a tetradecyl group, a hexadecyl group, an octadecyl group, an eicosyl group, a doeicosyl, a tetraeicosyl group, a hexaeicosyl group, an octaeicosyl group, and a triacontyl group; branched alkyl groups, such as an isopropyl group, an s-butyl group, a t-butyl group, a neopentyl group, a 1-ethylpropyl group, and a 1-heptyldecyl group; and cyclic alkyl groups, such as a cyclopentyl group, a cyclohexyl group, an abietyl group, and a cholesteryl group.

The alkylglyceryl ether-modified silicones represented by the general formula (5) can be produced by the method disclosed in Japanese Patent Laid-Open No. 4-108795.

The amount of the ether-modified silicones given above is preferably from 0.05 to 20% by weight, particularly 1 to 10% by weight in the cosmetic composition.

Although an amount of the ultraviolet shielding composite fine particles of the present invention in cosmetics depends upon the kinds of cosmetics produced, the amount is preferably 0.01 to 50% by weight, more preferably 0.05 to 40% by weight, particularly 0.1 to 30% by weight. When the amount of the ultraviolet shielding composite fine particles is less than 0.01% by weight, sufficient shielding effects against the ultraviolet light cannot be achieved, and when the amount exceeds 50% by weight, a pleasant sense of touch when used as cosmetics are undesirably lost. The amount of the ultraviolet shielding composite fine particles when using a dispersion oil agent composition thereof for cosmetics is determined so as to satisfy the amount specified in the cosmetics contained in the dispersion oil agent, the cosmetics comprising the ultraviolet shielding composite fine particles mentioned above.

The cosmetics of the present invention may be formulated in various forms as conventionally prepared. Although the forms are not particularly limited, the cosmetics may be formulated as various make-up products including lotions, emulsions, creams, ointments, aerosol cosmetics, powdery foundations, powdery eyeshadows, emulsified foundation creams, lipsticks, hair care preparations, and skin cleaners.

In addition, the cosmetics of the present invention preferably have SPF of not less than 8 and changes in color before and after skin application, determined as ΔE measured by color-and-color difference meter of not more than 3. From the viewpoint of sufficiently exhibiting the ultraviolet shielding effects, SPF is preferably not less than 8, more preferably not less than 10, particularly not less than 13. From the viewpoint of maintaining good appearance upon skin application, $\Delta E^*_{ab}$ is preferably not more than 3, more preferably not more than 2, particularly not more than 1. In the present invention, SPF is measured by using an analyzer "SPF-290" (manufactured by The Optometrics Group), and $\Delta E^*_{ab}$ is a value defined in JIS Z8729-1980.

The present invention will be explained hereinafter in more detail by means of the following examples, without intending to limit the scope of the present invention thereto.

EXAMPLE 1

366.5 g of a silica sol ("ST-C," manufactured by Nissan Chemical Industries, Ltd.; $SiO_2$ concentration: 20.5% by weight) and 20.0 g of titanium oxide ultrafine particles ("TTO-51(A)," manufactured by Ishihara Sangyo Kaisha, Ltd.; rutile-type) were mixed. To the mixture, water was added to make up a volume of one liter, yielding a starting material liquid mixture Specifically, the concentrations of $SiO_2$ and $TiO_2$ in the starting material liquid mixture were 1.25 mol/liter and 0.25 mol/liter, respectively, and the amount of the daughter-and-matrix particle mixture contained in the above starting material liquid mixture was about 10% by weight.

Next, glass beads (average particle diameter: 0.1 mm) were added to the above starting material liquid mixture, to give a weight ratio of the starting material liquid mixture to the glass beads of 175:325. The resulting mixture was subjected to a dispersion treatment for 6 hours using a beads mill ("TSG-6H," manufactured by Igarashi Kikai) at an agitation speed of 2000 r.p.m. After termination of the dispersion treatment, the glass beads were removed to give a liquid dispersion containing the composite fine particles of $TiO_2/SiO_2$ (the expression indicated herein is used in terms of daughter particles/matrix particles, the same could be said for the other examples set forth below).

84.6 g of the above liquid dispersion, 1500 g of ethanol, and 16.26 g of tetraethoxysilane were mixed, and the contents were heated to 50° C. in a water bath. After the temperature of the resulting mixture reached 50° C., a mixed solution of 3.9 ml of 1 N-hydrochloric acid and 300 g of ethanol was added dropwise to the liquid dispersion. After the dropwise addition was completed, the contents were allowed to react with one another at 50° C. for 2 hours and 30 minutes, to thereby surface-coat the composite fine particles with $SiO_2$. After the coating treatment was completed, a mixed solution of 0.98 ml of 4 N-sodium hydroxide aqueous solution and 50 g of ethanol was added to the resulting mixture to neutralize the hydrochloric acid. All of the above steps were carried out under stirring.

After the coating treatment, the liquid dispersion was subjected to a solid-liquid separation using a centrifuge, to give an ethanol-containing cake. The procedure of adding ethanol to the resulting cake to disperse the cake in ethanol and then subjecting the resulting dispersion to a solid-liquid separation using a centrifuge was repeated five times, to give an ethanol-containing cake of the composite fine particles having a solid component concentration of about 40% by weight.

Thereafter, 12.5 g of the ethanol-containing cake obtained above was mixed with 500 g of acetone, and the resulting mixture was subjected to an ultrasonic dispersion treatment. After the cake was completely dispersed in acetone, a water-repellent treatment was carried out by adding and mixing 2.0 g of methyl hydrogen polysiloxane ("KF99P," manufactured by Shin-Etsu Silicone Corporation) with the liquid dispersion obtained above. Thereafter, a drying treatment for the composite fine particles was carried out by drying the resulting liquid dispersion at 80° C., and then baking the resulting mixture at 130° C. for 2 hours. The resulting powder was repeatedly pulverized ten times using a mill ("A10," manufactured by IKA-Labourtechnik), to give the composite fine particles.

The particle diameter of the composite fine particles before the water-repellent treatment was measured by dispersing the ethanol-containing cake of the composite fine particles in water and obtaining the particle diameter using a laser-doppler type particle size analyzer ("DLS-700," manufactured by OTSUKA ELECTRONICS CO., LTD.). It was found that the average particle diameter, based on volume, was about 0.08 μm.

After the water-repellent treatment, the composite fine particles were white. The particles were observed by a scanning electron microscope (JSM-T100, manufactured by JEOL Ltd.). As a result, it was found that the particles had an average particle diameter of about 1 μm. Also, a cross section of the particles was observed by a transmission electron microscope (JEM-2000FX, manufactured by JEOL Ltd.) using an ultrathin sectioning method. Consequently, it was found that $TiO_2$ ultrafine particles (average particle diameter: about 0.01 μm) were dispersed in and supported by aggregates of $SiO_2$ ultrafine particles (average particle diameter: about 0.01 μm). In other words, the composite fine particles were $TiO_2/SiO_2$ composite fine particles; matrix particles were the aggregates of $SiO_2$ particles having a band gap energy of about 6.2 eV and a refractive index of about 1.46; and daughter particles were $TiO_2$ particles having a band gap energy of about 3.3 eV and a refractive index of about 2.71 (rutile-type).

The amount of the daughter particles in the above composite fine particles was about 8.5% by volume, which was calculated based on the compositional ratio of particles in the starting material liquid mixture and the amount of $SiO_2$ coating, wherein particle densities of $SiO_2$ and $TiO_2$ were 2.27 g/cm$^3$ and 3.84 g/cm$^3$, respectively. The refractive index of the composite fine particles was about 1.57, the refractive index being calculated from the amount of the daughter particles in the composite fine particles. Incidentally, the amount of the daughter particles dispersed in and supported by aggregates of the matrix particles, which did not include the $SiO_2$ coating layer portion, was about 13.6% by volume.

The composite fine particles before and after the water-repellent treatment were dispersed in white vaseline (manufactured by Wako Pure Chemical Industries, Ltd.), so as to have a concentration of the daughter particles of 1% by weight in a mixture comprising white vaseline and the composite fine particles. The resulting mixture was subjected to a 60-minute irradiation treatment with ultraviolet light having a central wavelength of 312 nm using an ultraviolet light source ("ENB-260C/J," manufactured by SPECTRONICS CORPORATION). As a result, for both liquid dispersions containing the composite fine particles before and after the water-repellent treatment, no color change of the white vaseline was observed The above showed that the catalytic activities were substantially inhibited in the resulting composite fine particles.

After the water-repellent treatment, when the composite fine particles were mixed with water, they showed a strong water repellent property When the composite fine particles were mixed with a silicone oil ("KF96A," manufactured by Shin-Etsu Silicone Corporation; refractive index: 1.40), the composite fine particles were rapidly dispersed in the silicone oil. 8.4 mg of the composite fine particles having the above refractive index were dispersed in 2 g of the silicone oil. The light transmittance of the resulting liquid dispersion was evaluated by an ultraviolet-visible light spectrophotometer ("UV-160A," manufactured by Shimadzu Corporation). The light transmittance was measured using a silicious cell having an optical path length of 1 mm in a wavelength of from 200 to 800 nm. The results are shown in FIG. 1.

In the figure, the light transmittance of the composite fine particles was substantially equal to 0% in the ultraviolet region B and the ultraviolet region C, the wavelengths of which were not longer than 300 nm. On the other hand, the composite fine particles showed remarkably high light transmittance values in the entire visible light region at a wavelength of from 400 to 800 nm, the light transmittance at 400 nm being 52%, and at 800 nm being 81%. Accordingly, the composite fine particles thus produced had a high transparency in the visible light region and a high shielding ability in the ultraviolet region.

EXAMPLE 2

366.5 g of a silica sol ("ST-C," manufactured by Nissan Chemical Industries, Ltd.; $SiO_2$ concentration: 20.5% by weight) and 20.3 g of zinc oxide ultrafine particles ("FINEX 75," manufactured by Sakai Chemical Industry Co., Ltd.) were mixed. To the mixture, water was added to make up a volume of one liter, yielding a starting material liquid mixture. Specifically, the concentrations of $SiO_2$ and ZnO in the starting material liquid mixture were 1.25 mol/liter and 0.25 mol/liter, respectively, and the amount of the daughter-and-matrix particle mixture contained in the above starting material liquid mixture was about 10% by weight.

Thereafter, the procedure of dispersing the starting material liquid mixture thus prepared using a high-pressure dispersing device ("LA-31," manufactured by Nanomizer INC.) was repeated ten times under the disintegration pressure of 1000 kg/cm$^2$. By the above dispersion treatment, a liquid dispersion containing $ZnO/SiO_2$ composite fine particles was obtained.

1500 g of ethanol, 16.26 g of tetraethoxysilane, and 3.9 ml of 1 N-hydrochloric acid were mixed, and the contents were heated to 50° C. in a water bath. After the temperature of the resulting mixture reached 50° C., the reaction mixture was matured for 2 hours and 30 minutes. After the maturation was completed, a mixed solution of 0.98 ml of 4 N-sodium hydroxide aqueous solution and 50 g of ethanol was added to the reaction mixture to neutralize the hydrochloric acid. Thereafter, a mixed solution of 84.6 g of the above liquid dispersion and 300 g of ethanol was added dropwise to the neutralized solution. After the dropwise addition was completed, the contents were allowed to react with one another at 50° C., to thereby surface-coat the composite fine particles with $SiO_2$. All of the above steps were carried out under stirring.

After the coating treatment, the liquid dispersion was subjected to a solid-liquid separation in the same manner as in Example 1, to give an ethanol-containing cake of the composite fine particles having a solid component concentration of about 40% by weight Thereafter, 12.5 g of the ethanol-containing cake obtained above was mixed with 500 g of acetone, and the resulting mixture was subjected to an ultrasonic dispersion treatment. After the cake was completely dispersed in acetone, a water-repellent treatment was carried out by adding and mixing 0.5 g of methyl hydrogen polysiloxane ("KF99P," manufactured by Shin-Etsu Silicone Corporation) with the liquid dispersion obtained above. Thereafter, a drying treatment for the composite fine particles was carried out by drying the resulting liquid dispersion at 80° C., and then baking the resulting mixture at 130° C. for 2 hours. The resulting powder was repeatedly pulverized ten times using a mill ("A10," manufactured by IKA-Labourtechnik), to give the composite fine particles.

The particle diameter of the composite fine particles before the water-repellent treatment was measured by dispersing the ethanol-containing cake of the composite fine particles in water and obtaining the particle diameter in the same manner as in Example 1. It was found that the average particle diameter, based on volume, was about 0.07 μm.

After the water-repellent treatment, the composite fine particles were white. The particles were observed by a scanning electron microscope (JSM-T100, manufactured by JEOL Ltd.). As a result, it was found that the particles had an average particle diameter of about 1 μm. Also, a cross section of the particles was observed by a transmission electron microscope (JEM-2000FX, manufactured by JEOL Ltd.) using an ultrathin sectioning method. Consequently, it was found that ZnO ultrafine particles (average particle diameter: about 0.01 μm) were dispersed in and supported by aggregates of $SiO_2$ ultrafine particles (average particle diameter: about 0.01 μm). In other words, the composite fine particles were $ZnO/SiO_2$ composite fine particles; matrix particles were the aggregates of $SiO_2$ particles having a band gap energy of about 6.2 eV and a refractive index of about 1.46; and daughter particles were ZnO particles having a band gap energy of about 3.2 eV and a refractive index of about 1.99.

The amount of the daughter particles in the above composite fine particles was about 5.9% by volume, which was calculated based on the compositional ratio of particles in the starting material liquid mixture and the amount of $SiO_2$ coating, wherein particle densities of $SiO_2$ and ZnO were 2.27 $g/cm^3$ and 5.78 $g/cm^3$, respectively. The refractive index of the composite fine particles was about 1.49, the refractive index being calculated from the amount of the daughter particles in the composite fine particles. Incidentally, the amount of the daughter particles dispersed in and supported by aggregates of the matrix particles, which did not include the $SiO_2$ coating layer portion, was about 9.6% by volume.

The composite fine particles before and after the water-repellent treatment were dispersed in white vaseline (manufactured by Wako Pure Chemical Industries, Ltd.), so as to have a concentration of the ZnO particles of 1% by weight in a mixture comprising white vaseline and the composite fine particles. Thereafter, the determination of color change was carried out in the same manner as in Example 1. The above showed that no color change took place in the white vaseline, and that the catalytic activities were substantially inhibited in the resulting composite fine particles.

Figure 2:
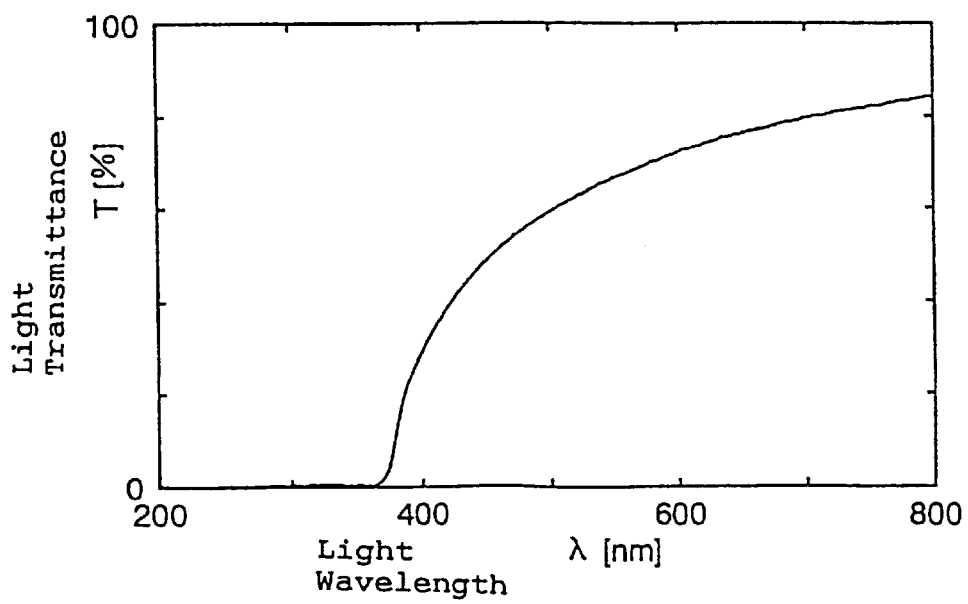
FIG. 2 is a graph showing the relationship between light wavelength and light transmittance of the ultraviolet shielding composite fine particles obtained in Example 2, as measured by an ultraviolet-visible light spectrophotometer.

After the water-repellent treatment, when the composite fine particles were mixed with water, they showed a strong water repellent property. When the composite fine particles were mixed with a silicone oil ("KF96A," manufactured by Shin-Etsu Silicone Corporation; refractive index: 1.40), the composite fine particles were rapidly dispersed in the silicone oil. 28 mg of the composite fine particles having the above refractive index were dispersed in 2 g of the silicone oil. The light transmittance of the resulting liquid dispersion was evaluated in the same manner as in Example 1. The results are shown in FIG. 2.

In the figure, the light transmittance of the composite fine particles was substantially equal to 0% in the ultraviolet region A, the ultraviolet region B, and the ultraviolet region C, the wavelengths of which were not longer than 350 nm. On the other hand, the composite fine particles show remarkably high light transmittance values in the entire visible light region at a wavelength of from 400 to 800 nm, the light transmittance at 400 nm being 30%, and at 800 nm being 84%. Accordingly, the composite fine particles thus produced had a high transparency in the visible light region and a high shielding ability in the ultraviolet region.

EXAMPLE 3

The formation of the $TiO_2/SiO_2$ composite fine particles, the $SiO_2$ surface coating treatment, and the solid-liquid separation were carried out in the same manner as in Example 1, to give an ethanol-containing cake of the composite fine particles having a solid component concentration of about 40% by weight.

Thereafter, 12.5 g of the ethanol-containing cake obtained above was mixed with 500 g of ethyl acetate, and the resulting mixture was subjected to an ultrasonic dispersion treatment. After the cake was completely dispersed in ethyl acetate, a water-repellent treatment was carried out by adding 2.5 g of an amino-modified silicone ("X-22-9261," manufactured by Shin-Etsu Silicone Corporation; molecular weight: 30000; and amino equivalency: 4980) to the liquid dispersion obtained above, and subjecting the resulting mixture to a further ultrasonic treatment at 50° C. for 3 hours.

42.5 g of a silicone oil ("KF96A," manufactured by Shin-Etsu Silicone Corporation; refractive index: 1.40) was added to the above liquid dispersion, followed by stirring and mixing. Thereafter, the resulting mixture was subjected to a topping treatment at 80° C. using a rotary evaporator to remove ethyl acetate, so that the composite fine particles were phase-transferred and dispersed in the silicone oil, to give a silicone oil dispersion of the composite fine particles having a concentration of the composite fine particles of 10% by weight.

The particle diameter of the composite fine particles before the water-repellent treatment was measured by dispersing the ethanol-containing cake of the composite fine particles in water and measuring the particle diameter in the same manner as in Example 1. It was found that the average particle diameter, based on volume, was about 0.08 μm.

After the water-repellent treatment, a cross section of the composite fine particles was observed by a transmission electron microscope (JEM-2000FX, manufactured by JEOL Ltd.) using an ultrathin sectioning method. Consequently, it was found that $TiO_2$ ultrafine particles (average particle diameter: about 0.01 μm) were dispersed in and supported by aggregates of $SiO_2$ ultrafine particles (average particle diameter: about 0.01 μm). In other words, the composite fine particles were $TiO_2/SiO_2$ composite fine particles; matrix particles were the aggregates of $SiO_2$ particles having a band gap energy of about 6.2 eV and a refractive index of about 1.46; and daughter particles were $TiO_2$ particles having a band gap energy of about 3.3 eV and a refractive index of about 2.71.

The amount of the daughter particles in the above composite fine particles was about 8.5% by volume, which was calculated based on the compositional ratio of the particles in the starting material liquid mixture and the amount of $SiO_2$ coating, wherein particle densities of $SiO_2$ and $TiO_2$ were 2.27 $g/cm^3$ and 3.84 $g/cm^3$, respectively. The refractive index of the composite fine particles was about 1.57, the refractive index being calculated from the amount of the daughter particles in the composite fine particles. Incidentally, the amount of the daughter particles dispersed in and supported by aggregates of the matrix particles, which did not include the $SiO_2$ coating layer portion, was about 13.6% by volume.

The silicone oil dispersion of the composite fine particles thus obtained was diluted in white vaseline (manufactured by Wako Pure Chemical Industries, Ltd.), so as to have a concentration of the $TiO_2$ particles of 1% by weight in a mixture comprising white vaseline and the composite fine particles. Thereafter, the determination of color change was carried out in the same manner as in Example 1. The above showed that no color change took place in the white vaseline, and that the catalytic activities were substantially inhibited in the resulting composite fine particles.

Figure 3:
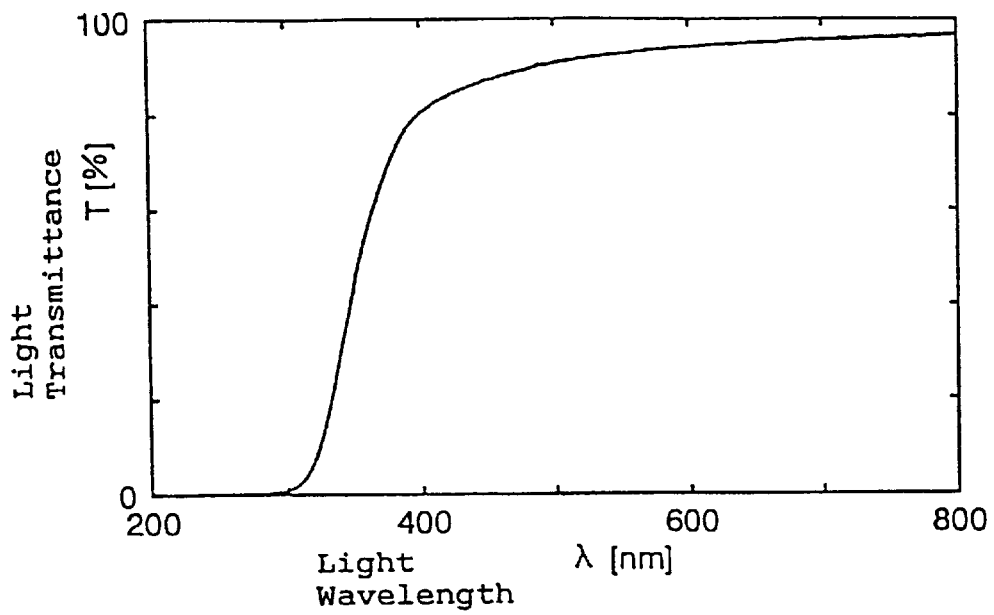
FIG. 3 is a graph showing the relationship between light wavelength and light transmittance of the ultraviolet shielding composite fine particles obtained in Example 3, as measured by an ultraviolet-visible light spectrophotometer.

After 0.1 g of the silicone oil dispersion of the composite fine particles thus obtained was diluted with 4.9 g of the silicone oil ("KP96A" used above), the light transmittance of the resulting liquid dispersion was evaluated in the same manner as in Example 1. The results are shown in FIG. 3.

In the figure, the light transmittance of the composite fine particles was substantially equal to 0% in the ultraviolet region B and the ultraviolet region C, the wavelengths of which were not longer than 300 nm. On the other hand, the composite fine particles show extremely high light transmittance values in the entire visible light region at a wavelength of from 400 to 800 nm, the light transmittance at 400 nm being 80%, and at 800 nm being 97%. Accordingly, the composite fine particles thus produced had a high transparency in the visible light region and a high shielding ability in the ultraviolet region.

EXAMPLE 4

366.5 g of a silica sol ("ST-C," manufactured by Nissan Chemical Industries, Ltd.; $SiO_2$ concentration: 20.5% by weight), 10.0 g of titanium oxide ultrafine particles ("TTO-51(A)," manufactured by Ishihara Sangyo Kaisha, Ltd.; rutile-type), and 40.7 g of zinc oxide ultrafine particles ("FINEX 75," manufactured by Sakai Chemical Industry Co., Ltd.) were mixed. To the mixture, water was added to make up a volume of one liter, yielding a starting material liquid mixture. Specifically, the concentrations of $SiO_2$, $TiO_2$, and ZnO in the starting material liquid mixture were 1.25 mol/liter, 0.125 mol/liter, and 0.5 mol/liter, respectively, and the amount of the daughter-and-matrix particle mixture contained in the above starting material liquid mixture was about 12% by weight.

The resulting starting material liquid mixture was subjected to a dispersion treatment in the same manner as in Example 1, to give a liquid dispersion containing the composite fine particles of $TiO_2+ZnO/SiO_2$. Thereafter, the resulting liquid dispersion was subjected to a $SiO_2$ surface-coating treatment, which was carried out in the same manner as in Example 2. Subsequent to the coating treatment, after the liquid dispersion was heated to 70° C., a water-repellent treatment was carried out by adding 0.74 g of an amino-modified silicone ("XF42-B0819," manufactured by Toshiba Silicone Corporation; molecular weight: 10000; and amino equivalency: 1600) to the liquid dispersion obtained above, and subjecting the resulting mixture to a further ultrasonic treatment for the composite fine particles of $TiO_2+ZnO/SiO_2$ at 70° C. for 2 hours.

After the water-repellent treatment, the liquid dispersion was subjected to a topping treatment at 75° C. using a rotary evaporator to remove ethanol and water, to thereby produce a liquid dispersion which was concentrated three times that of the liquid dispersion before the topping treatment. Thereafter, 900 g of n-hexane was added, and the resulting mixture was subjected to a reflux and dehydration treatment at 70° C.

After the reflux and dehydration treatment, 132.8 g of a silicone oil ("KF96A," manufactured by Shin-Etsu Silicone Corporation; refractive index: 1.40) was added to the above liquid dispersion, followed by stirring and mixing. Thereafter, the resulting mixture was subjected to a topping treatment at 80° C. using a rotary evaporator to remove ethanol and water, so that the composite fine particles were phase-transferred and dispersed in the silicone oil, to give a silicone oil dispersion of the composite fine particles having a concentration of the composite fine particles of 10% by weight.

After the coating treatment, the liquid dispersion was subjected to a solid-liquid separation in the same manner as in Example 1, to give an ethanol containing-cake of the composite fine particles. Thereafter, the particle diameter of the composite fine particles before the water-repellent treatment was measured by dispersing the ethanol-containing cake of the composite fine particles in water and obtaining the particle diameter using a laser-doppler type particle size analyzer ("DLS-700," manufactured by OTSUKA ELECTRONICS CO., LTD.). It was found that the average particle diameter, based on volume, was about 0.09 $\mu$m.

After the water-repellent treatment, a cross section of the composite fine particles was observed by a transmission electron microscope (JEM-2000FX, manufactured by JEOL Ltd.) using an ultrathin sectioning method. Consequently, it was found that $TiO_2$ ultrafine particles (average particle diameter: about 0.01 $\mu$m) and ZnO ultrafine particles (average particle diameter: about 0.01 $\mu$m) were dispersed in and supported by aggregates of $SiO_2$ ultrafine particles (average particle diameter: about 0.01 $\mu$m). In other words, the composite fine particles were $TiO_2+ZnO/SiO_2$ composite fine particles; matrix particles were the aggregates of $SiO_2$ particles having a band gap energy of about 6.2 eV and a refractive index of about 1.46; and daughter particles comprise $TiO_2$ particles having a band gap energy of about 3.3 eV and a refractive index of about 2.71 and ZnO particles having a band gap energy of about 3.2 eV and a refractive index of about 1.99.

The amount of the daughter particles in the above composite fine particles was about 14.1% by volume, which was calculated based on the compositional ratio of particles in the starting material liquid mixture and the amount of $SiO_2$ coating, wherein particle densities of $SiO_2$, $TiO_2$, and ZnO were 2.27 g/cm$^3$, 3.84 g/cm$^3$, and 5.78 g/cm$^3$, respectively. The refractive index of the composite fine particles was about 1.56, the refractive index being calculated from the amount of the daughter particles in the composite fine particles. Incidentally, the amount of the daughter particles dispersed in and supported by aggregates of the matrix particles, which did not include the $SiO_2$ coating layer portion, was about 22.6% by volume The composite fine particles before the water-repellent treatment were diluted in white vaseline (manufactured by Wako Pure Chemical Industries, Ltd.), so as to have a concentration of the $TiO_2$ particles of 1% by weight in a mixture comprising white vaseline and the composite fine particles. Thereafter, the determination of color change was carried out in the same manner as in Example 1. The above showed that no color change took place in the white vaseline, and that the catalytic activities were substantially inhibited in the resulting composite fine particles.

Figure 4:
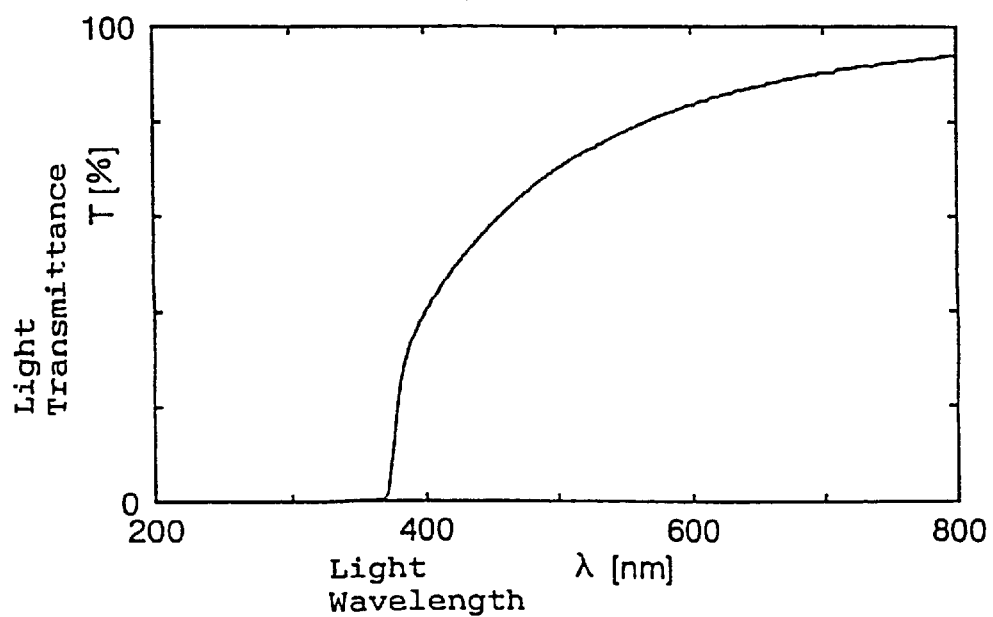
FIG. 4 is a graph showing the relationship between light wavelength and light transmittance of the ultraviolet shielding composite fine particles obtained in Example 4, as measured by an ultraviolet-visible light spectrophotometer.

After 0.1 g of the silicone oil dispersion of the composite fine particles thus obtained was diluted with 4.9 g of the silicone oil ("KP96A" used above), the light transmittance of the resulting liquid dispersion was evaluated in the same manner as in Example 1. The results are shown in FIG. 4.

In the figure, the light transmittance of the composite fine particles was substantially equal to 0% in the ultraviolet region A, the ultraviolet region B, and the ultraviolet region C, the wavelengths of which were not longer than 350 nm. On the other hand, the composite fine particles show extremely high light transmittance values in the entire visible light region at a wavelength of from 400 to 800 nm, the light transmittance at 400 nm being 40%, and at 800 nm being 94%. Accordingly, the composite fine particles thus produced had a high transparency in the visible light region and a high shielding ability in the ultraviolet region.

EXAMPLE 5

The preparation of the starting material liquid mixture and the dispersion treatment were carried out in the same manner as in Example 1, to give a liquid dispersion containing the composite fine particles of $TiO_2/SiO_2$.

84.6 g of the above liquid dispersion, 1500 g of ethanol, and 16.26 g of tetraethoxysilane were mixed, and the contents were heated to 50° C. in a water bath. After the temperature of the resulting mixture reached 50° C., a mixed solution of 3.9 ml of 1 N-hydrochloric acid and 300 g of ethanol was added dropwise to the liquid dispersion. After the dropwise addition was completed, the contents were allowed to react with one another at 50° C. for 2 hours and 30 minutes, to thereby surface-coat the composite fine particles with $SiO_2$. After the formation of the $SiO_2$ surface-coating was completed, 199.1 g of an isopropyl alcohol solution containing 0.04% by weight of aluminum isopropoxide was added dropwise to the resulting mixture, and the mixture was allowed to react with one another at 75° C. for 5 hours, to thereby further form an $Al_2O_3$ surface coating. After the coating treatment was completed, a mixed solution of 0.98 ml of 4 N-sodium hydroxide aqueous solution and 50 g of ethanol was added to the resulting mixture to neutralize the hydrochloric acid. All of the above steps were carried out under stirring.

After the coating treatment, 6.6 g of oleic acid was added to the liquid dispersion, and the resulting mixture was stirred. Thereafter, a water-repellent treatment was carried out for the $TiO_2/SiO_2$ composite fine particles by subjecting the resulting mixture to an ultrasonic treatment at 50° C. for 3 hours.

After the water-repellent treatment, the liquid dispersion was subjected to a topping treatment at 75° C. using a rotary evaporator to remove ethanol, isopropyl alcohol, and water, to thereby produce a liquid dispersion which was concentrated three times that of the liquid dispersion before the topping treatment. Thereafter, 900 g of n-hexane was added, and the resulting mixture was subjected to a reflux and dehydration treatment at 70° C.

After the reflux and dehydration treatment, 111.7 g of a silicone oil ("KF96A," manufactured by Shin-Etsu Silicone Corporation; refractive index: 1.40) was added to the above liquid dispersion, followed by stirring and mixing. Thereafter, the resulting mixture was subjected to a topping treatment at 80° C. using a rotary evaporator to remove ethanol, isopropyl alcohol, and water, so that the composite fine particles were phase-transferred and dispersed in the silicone oil, to give a silicone oil dispersion of the composite fine particles having a concentration of the composite fine particles of 10% by weight.

After the water-repellent treatment, a cross section of the composite fine particles was observed by a transmission electron microscope (JEM-2000FX, manufactured by JEOL Ltd.) using an ultrathin sectioning method. Consequently, it was found that $TiO_2$ ultrafine particles (average particle diameter: about 0.01 μm) were dispersed in and supported by aggregates of $SiO_2$ ultrafine particles (average particle diameter: about 0.01 μm). In other words, the composite fine particles were $TiO_2/SiO_2$ composite fine particles; matrix particles were the aggregates of $SiO_2$ particles having a band gap energy of about 6.2 eV and a refractive index of about 1.46; and daughter particles were $TiO_2$ particles having a band gap energy of about 3.3 eV and a refractive index of about 2.71 (rutile-type).

The amount of the daughter particles in the above composite fine particles was about 8.5% by volume, which was calculated based on the compositional ratio of particles in the starting material liquid mixture and the amount of $SiO_2$ coating, wherein particle densities of $SiO_2$ and $TiO_2$ were 2.27 $g/cm^3$ and 3.84 $g/cm^3$, respectively. The refractive index of the composite fine particles was about 1.57, the refractive index being calculated from the amount of the daughter particles in the composite fine particles. Incidentally, the amount of the daughter particles dispersed in and supported by aggregates of the matrix particles, which did not include the $SiO_2$ coating layer portion, was about 13.6% by volume.

The composite fine particles before and after the water-repellent treatment were dispersed in white vaseline (manufactured by Wako Pure Chemical Industries, Ltd.), so as to have a concentration of the daughter particles of 1% by weight in a mixture comprising white vaseline and the composite fine particles. Thereafter, the determination of color change was carried out in the same manner as in Example 1. The above showed that no color change took place in the white vaseline, and that the catalytic activities were substantially inhibited in the resulting composite fine particles.

After the coating treatment, the liquid dispersion was subjected to a solid-liquid separation in the same manner as in Example 1, to give an ethanol containing-cake of the composite fine particles. Thereafter, the particle diameter of the composite fine particles before the water-repellent treatment was measured by dispersing the ethanol-containing cake of the composite fine particles in water and obtaining the particle diameter using a laser-doppler type particle size analyzer ("DLS-700," manufactured by OTSUKA ELECTRONICS CO., LTD.). It was found that the average particle diameter, based on volume, was about 0.09 μm.

Figure 5:
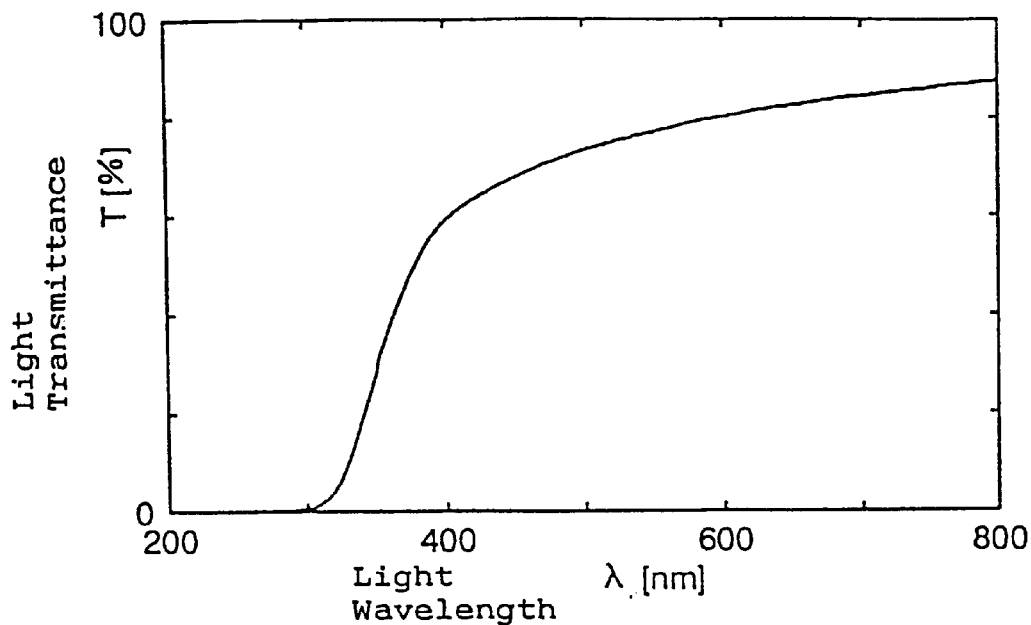
FIG. 5 is a graph showing the relationship between light wavelength and light transmittance of the ultraviolet shielding composite fine particles obtained in Example 5, as measured by an ultraviolet-visible light spectrophotometer.

After 0.15 g of the silicone oil dispersion of the composite fine particles thus obtained was diluted with 4.85 g of the silicone oil ("KP96A" used above), the light transmittance of the resulting liquid dispersion was evaluated in the same manner as in Example 1. The results are shown in FIG. 5.

In the figure, the light transmittance of the composite fine particles was substantially equal to 0% in the ultraviolet region B and the ultraviolet region C, the wavelengths of which were not longer than 300 nm. On the other hand, the composite fine particles show extremely high light transmittance values in the entire visible light region at a wavelength of from 400 to 800 nm, the light transmittance at 400 nm being 59%, and the light transmittance at 800 nm being 87%. Accordingly, the composite fine particles thus produced had a high transparency in the visible light region and a high shielding ability in the ultraviolet region.

EXAMPLE 6

The preparation of the starting material liquid mixture and the dispersion treatment were carried out in the same manner as in Example 4, to give a liquid dispersion containing the composite fine particles of $TiO_2+ZnO/SiO_2$.

1500 g of ethanol, 16.26 g of tetraethoxysilane, and 3.9 ml of 1 N-hydrochloric acid were mixed, and the contents were heated to 50° C. in a water bath. After the temperature of the resulting mixture reached 50° C., the reaction mixture was matured for 2 hours and 30 minutes. After the maturation was completed, a mixed solution of 0.98 ml of 4 N-sodium hydroxide aqueous solution and 50 g of ethanol was added to the reaction mixture to neutralize the hydrochloric acid. Thereafter, a mixed solution of 84.6 g of the above liquid dispersion containing the $TiO_2+ZnO/SiO_2$ composite fine particles and 300 g of ethanol was added dropwise to the neutralized solution. After the dropwise addition was completed, the contents were allowed to react with one another at 50° C. for 2 hours and 30 minutes, to thereby surface-coat the $TiO_2+ZnO/SiO_2$ composite fine particles with $SiO_2$. After the formation of the $SiO_2$ surface-coating was completed, 199.1 g of an isopropyl alcohol solution containing 0.04% by weight of aluminum isopropoxide was added dropwise to the resulting mixture, and the mixture was allowed to react with one another at 75° C. for 5 hours, to thereby further form an $Al_2O_3$ surface coating. All of the above steps were carried out under stirring.

After the coating treatment, 1.5 g of stearic acid was added to the liquid dispersion, and the resulting mixture was stirred. Thereafter, a water-repellent treatment was carried out for the $TiO_2+ZnO/SiO_2$ composite fine particles by subjecting the liquid dispersion obtained to an ultrasonic treatment at 70° C. for 2 hours.

The liquid dispersion obtained by the water-repellent treatment was subjected to a reflux and dehydration treatment in the same manner as in Example 5. After the reflux and dehydration treatment, 132.0 g of a silicone oil ("KF96A," manufactured by Shin-Etsu Silicone Corporation; refractive index: 1.40) was added to the above liquid dispersion, followed by stirring and mixing. Thereafter, the resulting mixture was subjected to a topping treatment at 80° C. using a rotary evaporator to remove ethanol, isopropyl alcohol, and water, so that the composite fine particles were phase-transferred and dispersed in the silicone oil, to give a silicone oil dispersion of the composite fine particles having a concentration of the composite fine particles of 10% by weight.

After the water-repellent treatment, a cross section of the composite fine particles was observed by a transmission electron microscope (JEM-2000FX, manufactured by JEOL Ltd.) using an ultrathin sectioning method. Consequently, it was found that ZnO ultrafine particles (average particle diameter: about 0.01 μm) and $TiO_2$ ultrafine particles (average particle diameter: about 0.01 μm) were dispersed in and supported by aggregates of $SiO_2$ ultrafine particles (average particle diameter: about 0.01 μm). In other words, the composite fine particles were $TiO_2+ZnO/SiO_2$ composite fine particles; matrix particles were the aggregates of $SiO_2$ particles having a band gap energy of about 6.2 eV and a refractive index of about 1.46; and daughter particles comprise ZnO particles having a band gap energy of about 3.2 eV and a refractive index of about 1.99 and $TiO_2$ particles having a band gap energy of about 3.3 eV and a refractive index of about 2.71.

The amount of the daughter particles in the above composite fine particles was about 14.1% by volume, which was calculated based on the compositional ratio of particles in the starting material liquid mixture and the amount of $SiO_2$ coating, wherein particle densities of $SiO_2$, $TiO_2$, and ZnO were 2.27 g/cm$^3$, 3.84 g/cm$^3$, and 5.78 g/cm$^3$, respectively. The refractive index of the composite fine particles was about 1.56, the refractive index being calculated from the amount of the daughter particles in the composite fine particles. Incidentally, the amount of the daughter particles dispersed in and supported by aggregates of the matrix particles, which did not include the $SiO_2$ coating layer portion, was about 22.6% by volume.

After the coating treatment, the liquid dispersion was subjected to a solid-liquid separation in the same manner as in Example 1, to give an ethanol containing-cake of the composite fine particles. Thereafter, the particle diameter of the composite fine particles before the water-repellent treatment was measured by dispersing the ethanol-containing cake of the composite fine particles in water and obtaining the particle diameter using a laser-doppler type particle size analyzer ("DLS-700" manufactured by OTSUKA ELECTRONICS CO., LTD.). It was found that the average particle diameter, based on volume, was about 0.10 μm.

The composite fine particles before the water-repellent treatment obtainable from the ethanol-containing cake of the composite fine particles were diluted in white vaseline (manufactured by Wako Pure Chemical Industries, Ltd.), so as to have a concentration of the $TiO_2$ particles of 1% by weight in a mixture comprising white vaseline and the composite fine particles. Thereafter, the determination of color change was carried out in the same manner as in Example 1. The above showed that no color change took place in the white vaseline, and that the catalytic activities were substantially inhibited in the resulting composite fine particles.

Figure 6:
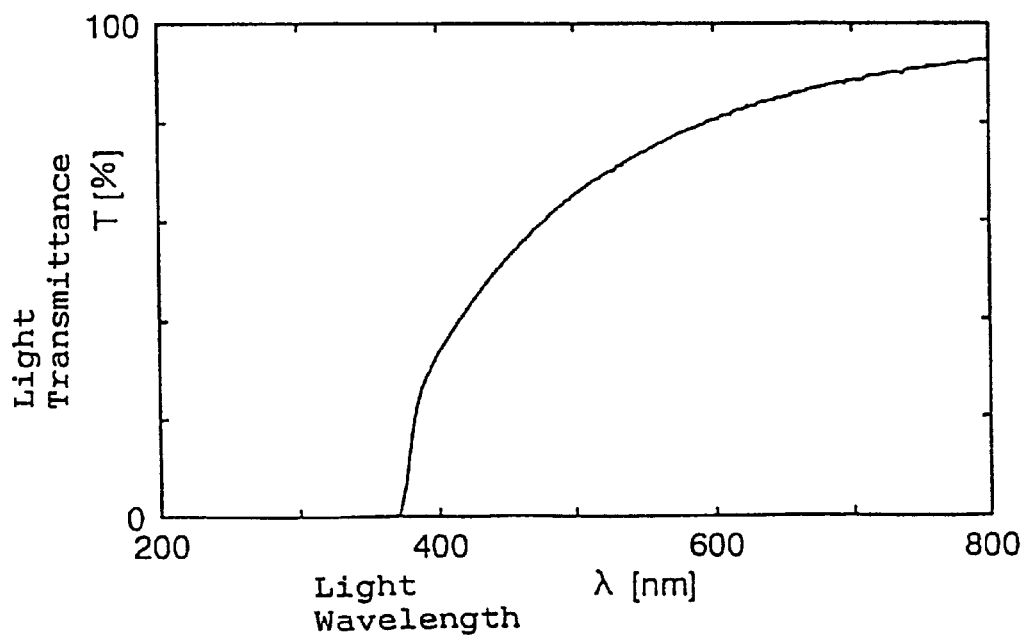
FIG. 6 is a graph showing the relationship between light wavelength and light transmittance of the ultraviolet shielding composite fine particles obtained in Example 6, as measured by an ultraviolet-visible light spectrophotometer.

After 0.1 g of the silicone oil dispersion of the composite fine particles obtained above was diluted with 4.9 g of the silicone oil ("KP96A" used above), the light transmittance of the resulting liquid dispersion was evaluated in the same manner as in Example 1. The results are shown in FIG. 6.

In the figure, the light transmittance of the composite fine particles was substantially equal to 0% in the ultraviolet region A, the ultraviolet region B, and the ultraviolet region C, the wavelengths of which were not longer than 350 nm. On the other hand, the composite fine particles show high light transmittance values in the entire visible light region at a wavelength of from 400 to 800 nm, the light transmittance at 400 nm being 33%, and at 800 nm being 93%. Accordingly, the composite fine particles thus produced had a high transparency in the visible light region and a high shielding ability in the ultraviolet region.

EXAMPLE 7

The formation of the $TiO_2/SiO_2$ composite fine particles was carried out in the same manner as in Example 1. Subsequently, the $SiO_2$ surface-coating treatment and the $Al_2O_3$ surface-coating treatment were carried out in the same manner as in Example 5.

After the surface-coating treatment, a water-repellent treatment was carried out by adding 0.66 g of dialkylphosphate ("DAP60H," manufactured by Kao Corporation) to the liquid dispersion, and subjecting the resulting mixture containing the $TiO_2/SiO_2$ composite fine particles to a further ultrasonic treatment at 75° C. for 1 hour.

After the water-repellent treatment, the liquid dispersion was subjected to a topping treatment at 75° C. using a rotary evaporator to remove ethanol, isopropyl alcohol, and water, to thereby produce a liquid dispersion which was concentrated three times that of the liquid dispersion before the topping treatment. Thereafter, 900 g of cyclohexane was added, and the resulting mixture was subjected to a reflux and dehydration treatment at 70° C.

After the reflux and dehydration treatment, 117.7 g of a silicone oil ("KF96A," manufactured by Shin-Etsu Silicone Corporation; refractive index: 1.40) was added to the above liquid dispersion, followed by stirring and mixing. Thereafter, the resulting mixture was subjected to a topping treatment at 80° C. using a rotary evaporator to remove ethanol, isopropyl alcohol, and water, so that the composite fine particles were phase-transferred and dispersed in the silicone oil, to give a silicone oil dispersion of the composite fine particles having a concentration of the composite fine particles of 10% by weight.

After the water-repellent treatment, a cross section of the composite fine particles was observed by a transmission electron microscope (JEM-2000FX, manufactured by JEOL Ltd.) using an ultrathin sectioning method. Consequently, it was found that $TiO_2$ ultrafine particles (average particle diameter: about 0.01 µm) were dispersed in and supported by aggregates of $SiO_2$ ultrafine particles (average particle diameter: about 0.01 µm). In other words, the composite fine particles were $TiO_2/SiO_2$ composite fine particles; matrix particles were the aggregates of $SiO_2$ particles having a band gap energy of about 6.2 eV and a refractive index of about 1.46; and daughter particles comprise $TiO_2$ particles having a band gap energy of about 3.3 eV and a refractive index of about 2.71.

The amount of the daughter particles in the above composite fine particles was about 8.5% by volume, which was calculated based on the compositional ratio of particles in the starting material liquid mixture and the amount of $SiO_2$ coating, wherein particle densities of $SiO_2$ and $TiO_2$ were 2.27 g/cm$^3$ and 3.84 g/cm$^3$, respectively. The refractive index of the composite fine particles was about 1.57, the refractive index being calculated from the amount of the daughter particles in the composite fine particles. Incidentally, the amount of the daughter particles dispersed in and supported by aggregates of the matrix particles, which did not include the $SiO_2$ coating layer portion, was about 13.6% by volume.

After the coating treatment, the liquid dispersion was subjected to a solid-liquid separation in the same manner as in Example 1, to give an ethanol containing-cake of the composite fine particles. Thereafter, the particle diameter of the composite fine particles before the water-repellent treatment was measured by dispersing the ethanol-containing cake of the composite fine particles in water and obtaining the particle diameter using a laser-doppler type particle size analyzer ("DLS-700," manufactured by OTSUKA ELECTRONICS CO., LTD.). It was found that the average particle diameter, based on volume, was about 0.09 µm.

The composite fine particles before the water-repellent treatment obtainable from the ethanol-containing cake of the composite fine particles were diluted in white vaseline (manufactured by Wako Pure Chemical Industries, Ltd.), so as to have a concentration of the $TiO_2$ particles of 1% by weight in a mixture comprising white vaseline and the composite fine particles Thereafter, the determination of color change was carried out in the same manner as in Example 1. The above showed that no color change took place in the white vaseline, and that the catalytic activities were substantially inhibited in the resulting composite fine particles.

Figure 7:
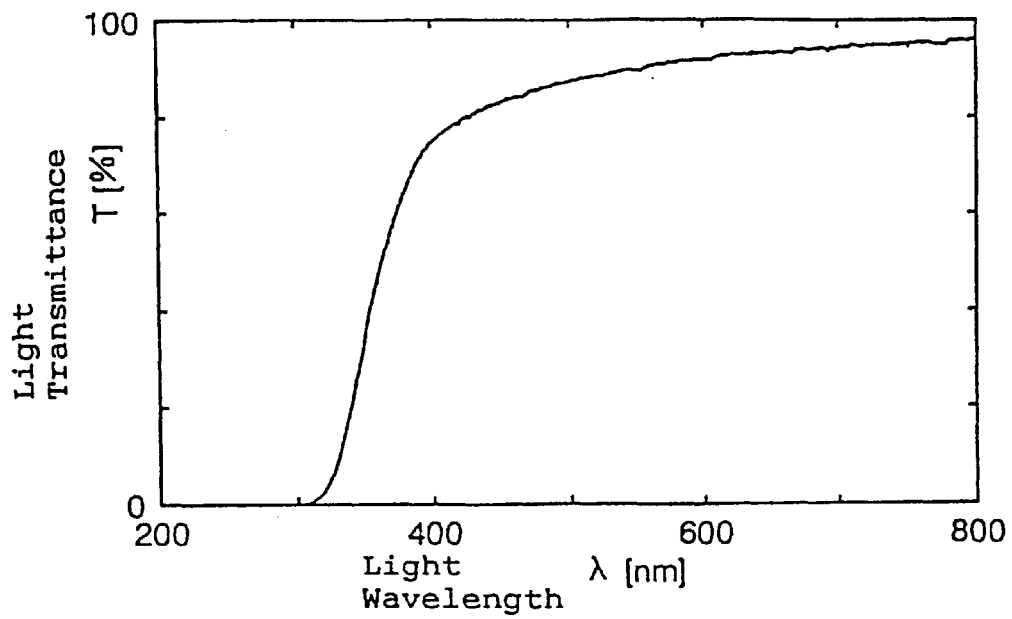
FIG. 7 is a graph showing the relationship between light wavelength and light transmittance of the ultraviolet shielding composite fine particles obtained in Example 7, as measured by an ultraviolet-visible light spectrophotometer.

After 0.1 g of the silicone oil dispersion of the composite fine particles obtained above was diluted with 4.9 g of the silicone oil ("KP96A" used above), the light transmittance of the resulting liquid dispersion was evaluated in the same manner as in Example 1. The results are shown in FIG. 7.

In the figure, the light transmittance of the composite fine particles was substantially equal to 0% in the ultraviolet region B and the ultraviolet region C, the wavelengths of which were not longer than 300 nm. On the other hand, the composite fine particles show extremely high light transmittance values in the entire visible light region at a wavelength of from 400 to 800 nm, the light transmittance at 400 nm being 74%, and at 800 nm being 96% Accordingly, the composite fine particles thus produced had a high transparency in the visible light region and a high shielding ability in the ultraviolet region.

EXAMPLE 8

The formation of the $TiO_2+ZnO/SiO_2$ composite fine particles, the $SiO_2$ surface-coating treatment, and the $Al_2O_3$ surface-coating treatment were carried out in the same manner as in Example 6.

After the surface-coating treatments, a water-repellent treatment was carried out by adding 0.74 g of dialkylphosphate ("DAP60H," manufactured by Kao Corporation) to the liquid dispersion, and subjecting the resulting mixture containing the $TiO_2+ZnO/SiO_2$ composite fine particles to a further ultrasonic treatment at 75° C. for 1 hour.

After the water-repellent treatment, the liquid dispersion was subjected to a reflux and dehydration treatment in the same manner as in Example 5. After the reflux and dehydration treatment, 132.8 g of a silicone oil ("KF96A," manufactured by Shin-Etsu Silicone Corporation; refractive index: 1.40) was added to the above liquid dispersion, followed by stirring and mixing. Thereafter, the resulting mixture was subjected to a topping treatment at 80° C. using a rotary evaporator to remove ethanol, isopropyl alcohol, and water, so that the composite fine particles were phase-transferred and dispersed in the silicone oil, to give a silicone oil dispersion of the composite fine particles having a concentration of the composite fine particles of 10% by weight.

After the water-repellent treatment, a cross section of the composite fine particles was observed by a transmission electron microscope (JEM-2000FX, manufactured by JEOL Ltd.) using an ultrathin sectioning method. Consequently, it was found that ZnO ultrafine particles (average particle diameter: about 0.01 µm) and $TiO_2$ ultrafine particles (average particle diameter: about 0.01 µm) were dispersed in and supported by aggregates of $SiO_2$ ultrafine particles (average particle diameter: about 0.01 µm). In other words, the composite fine particles were $TiO_2+ZnO/SiO_2$ composite fine particles; matrix particles were the aggregates of $SiO_2$ particles having a band gap energy of about 6.2 eV and a refractive index of about 1.46; and daughter particles comprise ZnO particles having a band gap energy of about 3.2 eV and a refractive index of about 1.99 and $TiO_2$ particles having a band gap energy of about 3.3 eV and a refractive index of about 2.71.

The amount of the daughter particles in the above composite fine particles was about 14.1% by volume, which was calculated based on the compositional ratio of particles in the starting material liquid mixture and the amount of $SiO_2$ coating, wherein particle densities of $SiO_2$, $TiO_2$, and ZnO were 2.27 g/cm$^3$, 3.84 g/cm$^3$, and 5.78 g/cm$^3$, respectively. The refractive index of the composite fine particles was about 156, the refractive index being calculated from the amount of the daughter particles in the composite fine particles. Incidentally, the amount of the daughter particles dispersed in and supported by aggregates of the matrix particles, which did not include the $SiO_2$ coating layer portion, was about 22.6% by volume.

After the coating treatment, the liquid dispersion was subjected to a solid-liquid separation in the same manner as in Example 1, to give an ethanol containing-cake of the composite fine particles. Thereafter, the particle diameter of the composite fine particles before the water-repellent treatment was measured by dispersing the ethanol-containing cake of the composite fine particles in water and obtaining the particle diameter using a laser-doppler type particle size analyzer ("DLS-700," manufactured by OTSUKA ELECTRONICS CO., LTD.). It was found that the average particle diameter, based on volume, was about 0.10 µm.

The composite fine particles before the water-repellent treatment obtainable from the ethanol-containing cake of the composite fine particles were diluted in white vaseline (manufactured by Wako Pure Chemical Industries, Ltd.), so as to have a concentration of the $TiO_2$ particles of 1% by weight in a mixture comprising white vaseline and the composite fine particles. Thereafter, the determination of color change was carried out in the same manner as in Example 1. The above showed that no color change took place in the white vaseline, and that the catalytic activities were substantially inhibited in the resulting composite fine particles.

Figure 8:
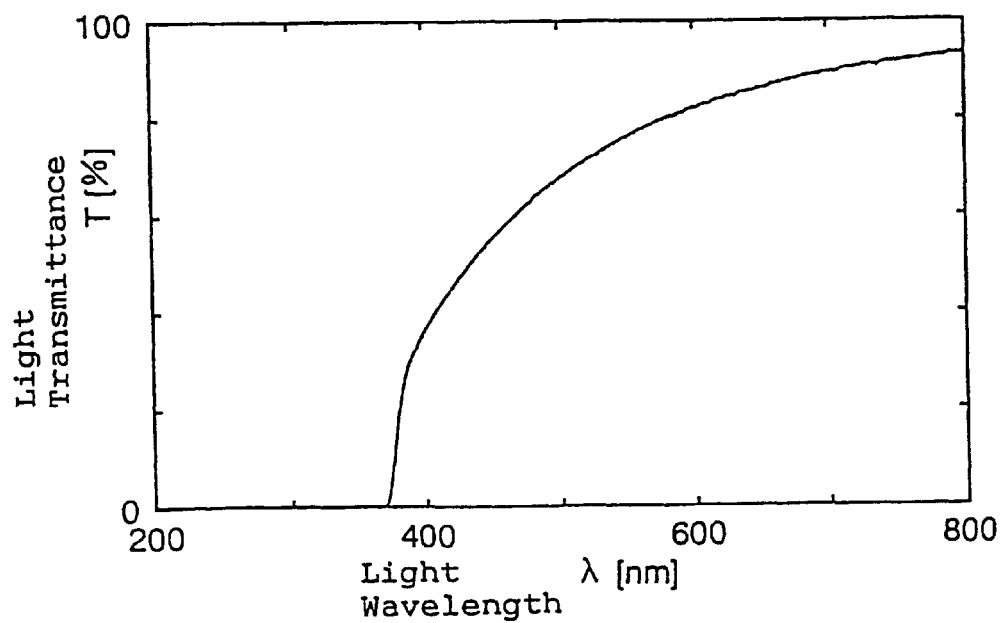
FIG. 8 is a graph showing the relationship between light wavelength and light transmittance of the ultraviolet shielding composite fine particles obtained in Example 8, as measured by an ultraviolet-visible light spectrophotometer.

After 0.1 g of the silicone oil dispersion of the composite fine particles obtained above was diluted with 4.9 g of the silicone oil ("KP96A" used above), the light transmittance of the resulting liquid dispersion was evaluated in the same manner as in Example 1. The results are shown in FIG. 8.

In the figure, the light transmittance of the composite fine particles was substantially equal to 0% in the ultraviolet region A, the ultraviolet region B, and the ultraviolet region C, the wavelengths of which were not longer than 350 nm. On the other hand, the composite fine particles show extremely high light transmittance values in the entire visible light region at a wavelength of from 400 to 800 nm, the light transmittance at 400 nm being 36%, and at 800 nm being 93%. Accordingly, the composite fine particles thus produced had a high transparency in the visible light region and a high shielding ability in the ultraviolet region.

EXAMPLE 9

The preparation of the starting material liquid mixture and the dispersion treatment were carried out in the same manner as in Example 2, to give a liquid dispersion containing the composite fine particles of $ZnO/SiO_2$.

1500 g of ethanol, 16.26 g of tetraethoxysilane, and 3.9 ml of 1 N-hydrochloric acid were mixed, and the contents were heated to 50° C. in a water bath. After the temperature of the resulting mixture reached 50° C, the reaction mixture was matured for 2 hours and 30 minutes. After the maturation was completed, a mixed solution of 0.98 ml of 4 N-sodium hydroxide aqueous solution and 50 g of ethanol was added to the reaction mixture to neutralize the hydrochloric acid. Thereafter, a mixed solution of 84.6 g of the above liquid dispersion containing the $ZnO/SiO_2$ composite fine particles and 300 g of ethanol was added dropwise to the neutralized solution. After the dropwise addition was completed, the contents were allowed to react with one another at 50° C., to thereby surface-coat the $ZnO/SiO_2$ composite fine particles with $SiO_2$. After the formation of the $SiO_2$ surface-coating was completed, 9.6 g of a mixed solution of aluminum tri-sec-butoxide, isopropyl alcohol and ethanol solution (weight ratio: 1:9:90 (% by weight)) was added dropwise to the resulting mixture, and the mixture was allowed to react with one another at 75° C. for 5 hours, to thereby further form an $Al_2O_3$ surface coating. All of the above steps were carried out under stirring.

After the surface-coating treatment, a water-repellent treatment was carried out by adding 0.66 g of dialkylphosphate ("DAP60H," manufactured by Kao Corporation) to the liquid dispersion, and subjecting the resulting mixture containing the $ZnO/SiO_2$ composite fine particles to an ultrasonic treatment at 75° C. for 1 hour.

After the water-repellent treatment, the liquid dispersion was subjected to a reflux and dehydration treatment in the same manner as in Example 5. After the reflux and dehydration treatment, 117.7 g of a silicone oil ("KF96A," manufactured by Shin-Etsu Silicone Corporation; refractive index: 1.40) was added to the above liquid dispersion, followed by stirring and mixing. Thereafter, the resulting mixture was subjected to a topping treatment at 80° C. using a rotary evaporator to remove ethanol, isopropyl alcohol, and water, so that the composite fine particles were phase-transferred and dispersed in the silicone oil, to give a silicone oil dispersion of the composite fine particles having a concentration of the composite fine particles of 10% by weight.

After the water-repellent treatment, a cross section of the composite fine particles was observed by a transmission electron microscope (JEM-2000FX, manufactured by JEOL Ltd.) using an ultrathin sectioning method. Consequently, it was found that ZnO ultrafine particles (average particle diameter: about 0.01 $\mu$m) were dispersed in and supported by aggregates of $SiO_2$ ultrafine particles (average particle diameter: about 0.01 $\mu$m). In other words, the composite fine particles were $ZnO/SiO_2$ composite fine particles; matrix particles were the aggregates of $SiO_2$ particles having a band gap energy of about 6.2 eV and a refractive index of about 1.46; and daughter particles comprise ZnO particles having a band gap energy of about 3.2 eV and a refractive index of about 1.99.

The amount of the daughter particles in the above composite fine particles was about 5.9% by volume, which was calculated based on the compositional ratio of particles in the starting material liquid mixture and the amount of $SiO_2$ coating, wherein particle densities of $SiO_2$ and ZnO were 2.27 g/cm$^3$ and 5.78 g/cm$^3$, respectively. The refractive index of the composite fine particles was about 1.49, the refractive index being calculated from the amount of the daughter particles in the composite fine particles. Incidentally, the amount of the daughter particles dispersed in and supported by aggregates of the matrix particles, which did not include the $SiO_2$ coating layer portion, was about 9.6% by volume.

After the coating treatment, the liquid dispersion was subjected to a solid-liquid separation in the same manner as in Example 1, to give an ethanol containing-cake of the composite fine particles. Thereafter, the particle diameter of the composite fine particles before the water-repellent treatment was measured by dispersing the ethanol-containing cake of the composite fine particles in water and obtaining the particle diameter using a laser-doppler type particle size analyzer ("DLS-700," manufactured by OTSUKA ELECTRONICS CO, LTD.). It was found that the average particle diameter, based on volume, was about 0.08 $\mu$m.

The composite fine particles before the water-repellent treatment obtainable from the ethanol-containing cake of the composite fine particles were diluted in white vaseline (manufactured by Wako Pure Chemical Industries, Ltd.), so as to have a concentration of the ZnO particles of 1% by weight in a mixture comprising white vaseline and the composite fine particles. Thereafter, the determination of color change was carried out in the same manner as in Example 1. The above showed that no color change took place in the white vaseline, and that the catalytic activities were substantially inhibited in the resulting composite fine particles.

Figure 9:
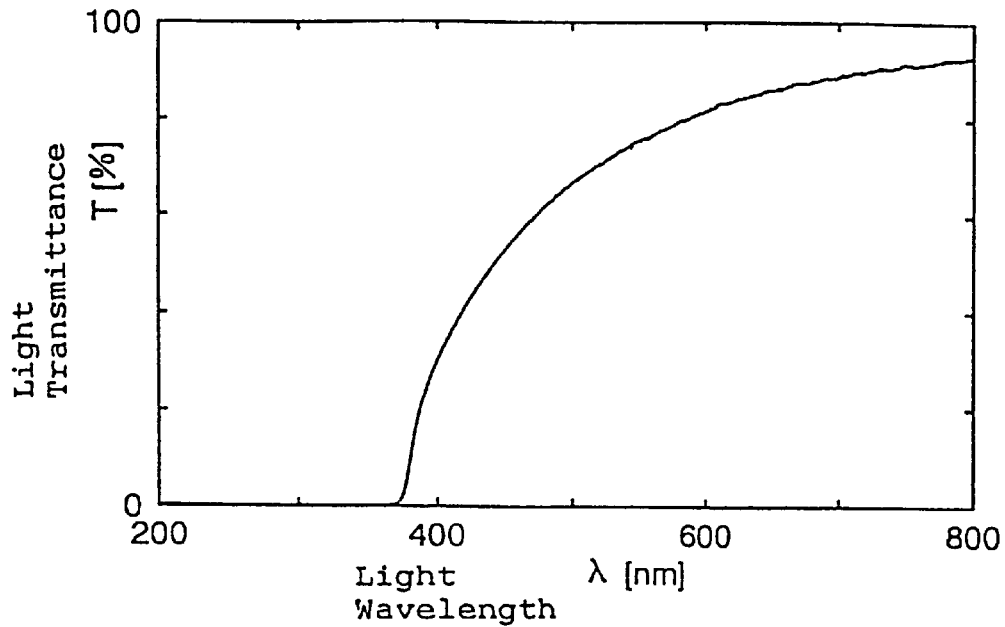
FIG. 9 is a graph showing the relationship between light wavelength and light transmittance of the ultraviolet shielding composite fine particles obtained in Example 9, as measured by an ultraviolet-visible light spectrophotometer.

After 0.4 g of the silicone oil dispersion of the composite fine particles obtained above was diluted with 4.6 g of the silicone oil ("KP96A" used above), the light transmittance of the resulting liquid dispersion was evaluated in the same manner as in Example 1. The results are shown in FIG. 9.

In the figure, the light transmittance of the composite fine particles was substantially equal to 0% in the ultraviolet region A, the ultraviolet region B, and the ultraviolet region C, the wavelengths of which were not longer than 350 nm.

On the other hand, the composite fine particles show high light transmittance values in the entire visible light region at a wavelength of from 400 to 800 nm, the light transmittance at 400 nm being 30%, and at 800 nm being 93%. Accordingly, the composite fine particles thus produced had a high transparency in the visible light region and a high shielding ability in the ultraviolet region.

EXAMPLE 10

366.5 g of a silica sol ("ST-C," manufactured by Nissan Chemical Industries, Ltd.; $SiO_2$ concentration: 20.5% by weight) and 39.9 g of titanium oxide ultrafine particles ("IT-S," manufactured by Idemitsu Kosan Co., Ltd.; amorphous-type) were mixed. To the mixture, water was added to make up a volume of one liter, yielding a starting material liquid mixture. Specifically, the concentrations of $SiO_2$ and $TiO_2$ in the starting material liquid mixture were 1.25 mol/liter and 0.5 mol/liter, respectively, and the amount of the daughter-and-matrix particle mixture contained in the above starting material liquid mixture was about 11% by weight.

The above starting material liquid mixture thus prepared was subjected to a dispersion treatment for 30 minutes using a disperser ("BIOMIXER," manufactured by Nippon Seiki Co., Ltd.) at an agitation speed of 15000 r.p.m., to give a liquid dispersion containing the composite fine particles of $TiO_2/SiO_2$.

After the surface-coating treatment, a water-repellent treatment was carried out by adding 0.70 g of dialkylphosphate ("DAP60H," manufactured by Kao Corporation) to the liquid dispersion, and subjecting the resulting mixture containing the $TiO_2/SiO_2$ composite fine particles to an ultrasonic treatment at 75° C. for 1 hour.

After the water-repellent treatment, the liquid dispersion was subjected to a reflux and dehydration treatment in the same manner as in Example 5. After the reflux and dehydration treatment, 125.6 g of a silicone oil ("KF96A," manufactured by Shin-Etsu Silicone Corporation; refractive index: 1.40) was added to the liquid dispersion followed by stirring and mixing. Thereafter, the resulting mixture was subjected to a topping treatment at 80° C. using a rotary evaporator to remove ethanol, isopropyl alcohol, and water, so that the composite fine particles were phase-transferred and dispersed in the silicone oil, to give a silicone oil dispersion of the composite fine particles having a concentration of the composite fine particles of 10% by weight.

After the water-repellent treatment, a cross section of the composite fine particles was observed by a transmission electron microscope (JEM-2000FX, manufactured by JEOL Ltd.) using an ultrathin sectioning method. Consequently, it was found that $TiO_2$ ultrafine particles (average particle diameter: about 0.01 μm) were dispersed in and supported by aggregates of $SiO_2$ ultrafine particles (average particle diameter: about 0.01 μm). In other words, the composite fine particles were $TiO_2/SiO_2$ composite fine particles; matrix particles were the aggregates of $SiO_2$ particles having a band gap energy of about 6.2 eV and a refractive index of about 1.46; and daughter particles were $TiO_2$ particles having a band gap energy of about 3.4 eV and a refractive index of about 2.52.

The amount of the daughter particles in the above composite fine particles was about 15.1% by volume, which was calculated based on the compositional ratio of particles in the starting material liquid mixture and the amount of $SiO_2$ coating, wherein particle densities of $SiO_2$ and $TiO_2$ were 2.27 g/cm³ and 3.84 g/cm³, respectively. The refractive index of the composite fine particles was about 1.62, the refractive index being calculated from the amount of the daughter particles in the composite fine particles. Incidentally, the amount of the daughter particles dispersed in and supported by aggregates of the matrix particles, which did not include the $SiO_2$ coating layer portion, was about 23.9% by volume.

After the coating treatment, the liquid dispersion was subjected to a solid-liquid separation in the same manner as in Example 1, to give an ethanol containing-cake of the composite fine particles. Thereafter, the particle diameter of the composite fine particles before the water-repellent treatment was measured by dispersing the ethanol-containing cake of the composite fine particles in water and obtaining the particle diameter using a laser-doppler type particle size analyzer ("DLS-700," manufactured by OTSUKA ELECTRONICS CO., LTD.). It was found that the average particle diameter, based on volume, was about 0.10 μm.

The composite fine particles before and after the water-repellent treatment were dispersed in white vaseline (manufactured by Wako Pure Chemical Industries, Ltd.), so as to have a concentration of the $TiO_2$ particles of 1% by weight in a mixture comprising white vaseline and the composite fine particles. Thereafter, the determination of color change was carried out in the same manner as in Example 1. The above showed that no color change took place in the white vaseline, and that the catalytic activities were substantially inhibited in the resulting composite fine particles.

Figure 10:
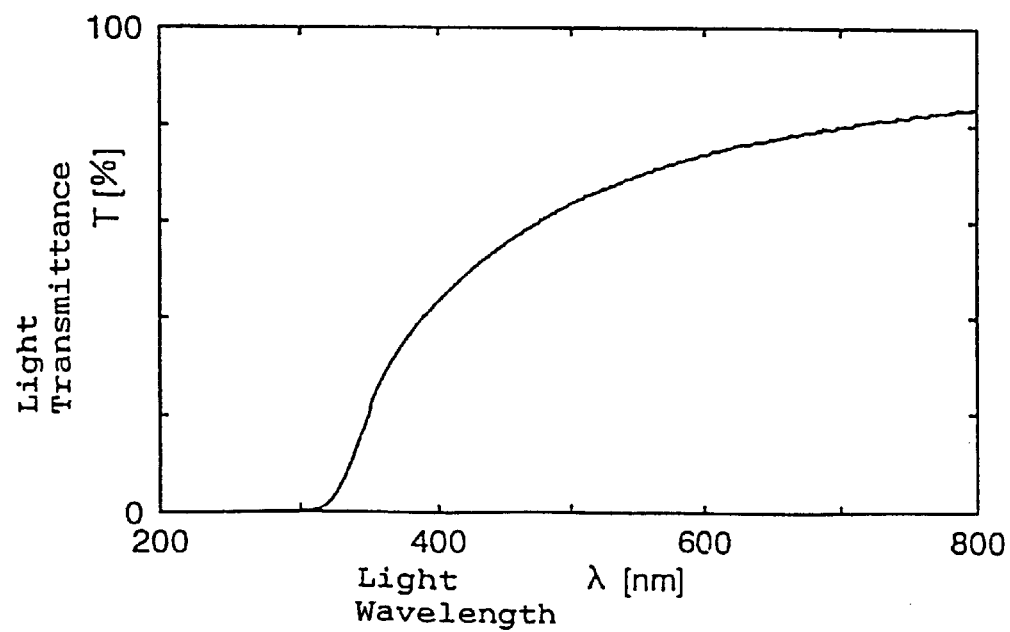
FIG. 10 is a graph showing the relationship between light wavelength and light transmittance of the ultraviolet shielding composite fine particles obtained in Example 10, as measured by an ultraviolet-visible light spectrophotometer.

After 0.1 g of the silicone oil dispersion of the composite fine particles obtained above was diluted with 4.9 g of the silicone oil ("KP96A" used above), the light transmittance of the resulting liquid dispersion was evaluated in the same manner as in Example 1. The results are shown in FIG. 10.

In the figure, the light transmittance of the composite fine particles was substantially equal to 0% in the ultraviolet region B and the ultraviolet region C, the wavelengths of which were not longer than 300 nm. On the other hand, the composite fine particles show high light transmittance values in the entire visible light region at a wavelength of from 400 to 800 nm, the light transmittance at 400 nm being 43%, and at 800 nm being 83%. Accordingly, the composite fine particles thus produced had a high transparency in the visible light region and a high shielding ability in the ultraviolet region.

EXAMPLE 11

268.3 g of a silica sol ("ST-C," manufactured by Nissan Chemical Industries, Ltd.; $SiO_2$ concentration: 20.5% by weight) and 50.0 g of titanium oxide ultrafine particles ("TTO-51(A)," manufactured by Ishihara Sangyo Kaisha, Ltd.; rutile-type) were mixed. To the mixture, water was added to make up a volume of one liter, yielding a starting material liquid mixture. Specifically, the concentrations of $SiO_2$ and $TiO_2$ in the starting material liquid mixture were 0.92 mol/liter and 0.63 mol/liter, respectively, and the amount of the daughter-and-matrix particle mixture contained in the above starting material liquid mixture was about 11% by weight.

The above starting material liquid mixture thus prepared was subjected to a dispersion treatment for 30 minutes using a dynomill ("KDL-PILOT," manufactured by Willy A. Bachofen AG) under the conditions of an agitation speed of 3600 r.p.m. and a solution/media ratio of 600 cc/1200 cc, for 8 minutes, the treatment procedure being repeated two more times, to give a liquid dispersion containing $TiO_2/SiO_2$ ultrafine aggregates comprising $TiO_2$ as the daughter particles and $SiO_2$ as the matrix particles.

188 g of the above liquid dispersion, 1400 g of ethanol, and 32.6 g of tetraethoxysilane were mixed, and the contents were heated to 50° C. in a water bath. After the temperature of the resulting mixture reached 50° C., a mixed solution of 1.56 ml of 1 N-hydrochloric acid and 600 g of ethanol was added dropwise to the liquid dispersion. After the dropwise addition was completed, the contents were allowed to react with one another at 50° C. for 2 hours and 30 minutes, to thereby surface-coat the composite fine particles with $SiO_2$. All of the above steps were carried out under stirring.

After the topping treatment, the liquid dispersion was further subjected to a topping treatment at 75° C. using a rotary evaporator to remove ethanol and water, to thereby produce a liquid dispersion which was concentrated ten times that of the liquid dispersion before the topping treatment. Thereafter, 2782 g of isopropyl alcohol was added dropwise to the concentrated liquid dispersion under stirring.

After the above topping treatment, the liquid dispersion was subjected to a further topping treatment at 75° C. using a rotary evaporator to remove ethanol, isopropyl alcohol, and water, to thereby produce a liquid dispersion which was concentrated five times the liquid dispersion before the topping treatment.

After the concentration of the liquid dispersion was completed, a mixed solution of 0.39 ml of 4 N-sodium hydroxide aqueous solution and 20 g of ethanol was added to the liquid dispersion to neutralize the hydrochloric acid. All of the above steps were carried out under stirring.

While stirring the liquid dispersion obtained above, 600 g of a silicone oil ("SH244," manufactured by Toray-Dow Corning Corporation; refractive index: 1.39) was added dropwise, and mixed with the liquid dispersion. Thereafter, a water-repellent treatment for the $TiO_2/SiO_2$ composite fine particles was carried out by the steps of adding dropwise a mixed solution of 0.6 g of an amino-modified silicone ("XF42-B0819," manufactured by Toshiba Silicone Corporation; molecular weight: 10000; and amino equivalency: 1600) and 240 g of the silicone oil ("SH244" used above) and mixing the mixed solution with the resulting liquid dispersion; subjecting the resulting liquid dispersion to a topping treatment at 80° C. using a rotary evaporator to remove ethanol, isopropyl alcohol, and water; and adding dropwise a mixed solution of 2.4 g of the amino-modified silicone ("XF42-B0819" used above) and 360 g of the silicone oil ("SH244" used above) and mixing the mixed solution with the liquid dispersion after the topping treatment.

The resulting liquid dispersion was subjected to a dispersion treatment using an ultrasonic disperser for one hour. Thereafter, the resulting mixture was subjected to a topping treatment at 80° C. using a rotary evaporator to remove ethanol, isopropyl alcohol, water, and a silicone oil, so that the composite fine particles were phase-transferred and dispersed in the silicone oil, to give a silicone oil dispersion of the composite fine particles having a concentration of the composite fine particles of 35% by weight.

After the coating treatment, the liquid dispersion was subjected to a solid-liquid separation in the same manner as in Example 1, to give an ethanol containing-cake of the composite fine particles. Thereafter, the particle diameter of the composite fine particles before the water-repellent treatment was measured by dispersing the ethanol-containing cake of the composite fine particles in water and obtaining the particle diameter using a laser-doppler type particle size analyzer ("DLS-700," manufactured by OTSUKA ELECTRONICS CO., LTD.). It was found that the average particle diameter, based on volume, was about 0.08 μm.

After the water-repellent treatment, a cross section of the composite fine particles was observed by a transmission electron microscope (JEM-2000FX, manufactured by JEOL Ltd.) using an ultrathin sectioning method. Consequently, it was found that $TiO_2$ ultrafine particles (average particle diameter: about 0.01 μm) were dispersed in and supported by aggregates of $SiO_2$ ultrafine particles (average particle diameter: about 0.01 μm). In other words, the composite fine particles were $TiO_2/SiO_2$ composite fine particles; matrix particles were the aggregates of $SiO_2$ particles having a band gap energy of about 6.2 eV and a refractive index of about 1.46; and daughter particles comprise $TiO_2$ particles having a band gap energy of about 3.3 eV and a refractive index of about 2.71.

The amount of the daughter particles in the above composite fine particles was about 22.3% by volume, which was calculated based on the compositional ratio of particles in the starting material liquid mixture and the amount of $SiO_2$ coating, wherein particle densities of $SiO_2$ and $TiO_2$ were 2.27 g/cm$^3$ and 3.84 g/cm$^3$, respectively. The refractive index of the composite fine particles was about 1.74, the refractive index being calculated from the amount of the daughter particles in the composite fine particles. Incidentally, the amount of the daughter particles dispersed in and supported by aggregates of the matrix particles, which did not include the $SiO_2$ coating layer portion, was about 35.0% by volume.

The composite fine particles before the water-repellent treatment were diluted in white vaseline (manufactured by Wako Pure Chemical Industries, Ltd.), so as to have a concentration of the $TiO_2$ particles of 1% by weight in a mixture comprising white vaseline and the composite fine particles. Thereafter, the determination of color change was carried out in the same manner as in Example 1. The above showed that no color change took place in the white vaseline, and that the catalytic activities were substantially inhibited in the resulting composite fine particles.

Figure 11:
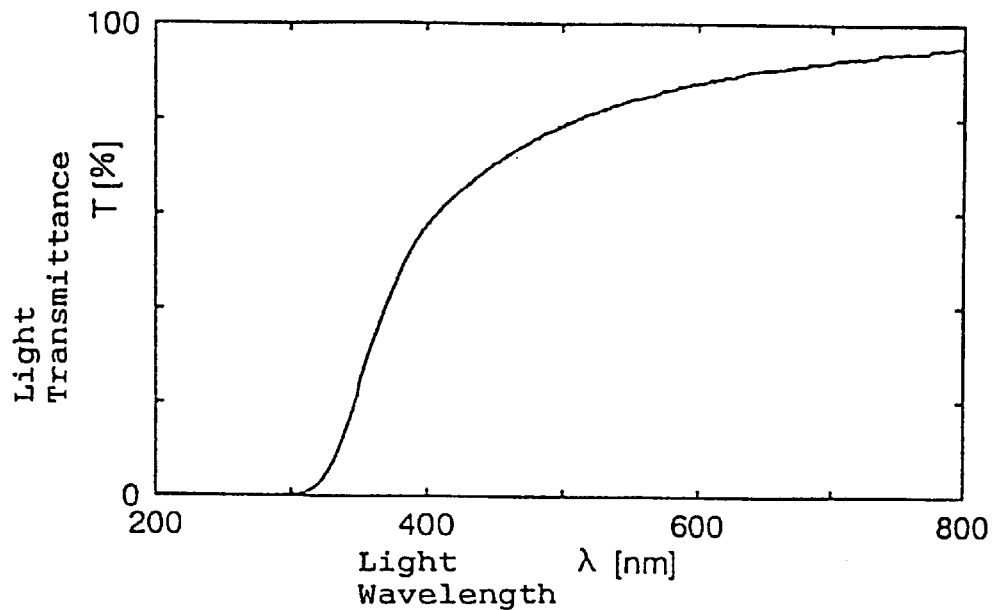
FIG. 11 is a graph showing the relationship between light wavelength and light transmittance of the ultraviolet shielding composite fine particles obtained in Example 11, as measured by an ultraviolet-visible light spectrophotometer.

After 0.057 g of the silicone oil dispersion of the composite fine particles obtained above was diluted with 9.943 g of the silicone oil ("KP96A" used above), the light transmittance of the resulting liquid dispersion was evaluated in the same manner as in Example 1. The results are shown in FIG. 11.

In the figure, the light transmittance of the composite fine particles was substantially equal to 0% in the ultraviolet region B and the ultraviolet region C, the wavelengths of which were not longer than 300 nm. On the other hand, the composite fine particles show extremely high light transmittance values in the entire visible light region at a wavelength of from 400 to 800 nm, the light transmittance at 400 nm being 57%, and at 800 nm being 95%. Accordingly, the composite fine particles thus produced had a high transparency in the visible light region and a high shielding ability in the ultraviolet region.

EXAMPLE 12

The formation of the $TiO_2/SiO_2$ composite fine particles and the $SiO_2$ surface-coating treatment were carried out in the same manner as in Example 11.

After the coating step was completed, a mixed solution of 0.39 ml of 4 N-sodium hydroxide aqueous solution and 20 g of ethanol was added to the reaction mixture to neutralize the hydrochloric acid. All of the above steps were carried out under stirring.

While stirring the liquid dispersion obtained above, a water-repellent treatment for the $TiO_2/SiO_2$ composite fine particles was carried out by the steps of adding dropwise a solution. comprising 3.0 g of an oxazoline-modified silicone ("OS96-20," manufactured by Kao Corporation) dissolved in 860 g of ethanol and mixing the mixed solution with the liquid dispersion.

After the water-repellent treatment, the liquid dispersion was subjected to a topping treatment at 75° C. using a rotary evaporator to remove ethanol and water, to thereby produce a liquid dispersion which was concentrated five times that of the liquid dispersion before the topping treatment.

While stirring the liquid dispersion obtained above, 575 g of a silicone oil ("SH244," manufactured by Toray-Dow Corning Corporation; refractive index: 1.39) was added dropwise, and mixed with the liquid dispersion. Thereafter, the resulting liquid dispersion was subjected to a topping treatment at 80° C. using a rotary evaporator to remove ethanol and water.

The resulting liquid dispersion was subjected to a dispersion treatment using a homogenizer for one hour. Thereafter, the resulting mixture was subjected to a topping treatment at 80° C. using a rotary evaporator to remove ethanol, water, and a silicone oil, so that the composite fine particles were phase-transferred and dispersed in the silicone oil, to give a silicone oil dispersion of the composite fine particles having a concentration of the composite fine particles of 15% by weight.

After the coating treatment, the liquid dispersion was subjected to a solid-liquid separation in the same manner as in Example 1, to give an ethanol containing-cake of the composite fine particles. Thereafter, the particle diameter of the composite fine particles before the water-repellent treatment was measured by dispersing the ethanol-containing cake of the composite fine particles in water and obtaining the particle diameter using a laser-doppler type particle size analyzer ("DLS-700," manufactured by OTSUKA ELECTRONICS CO., LTD.). It was found that the average particle diameter, based on volume, was about 0.08 $\mu$m.

After the water-repellent treatment, a cross section of the composite fine particles was observed by a transmission electron microscope (JEM-2000FX, manufactured by JEOL Ltd.) using an ultrathin sectioning method. Consequently, it was found that $TiO_2$ ultrafine particles (average particle diameter: about 0.01 $\mu$m) were dispersed in and supported by aggregates of $SiO_2$ ultrafine particles (average particle diameter: about 0.01 $\mu$m). In other words, the composite fine particles were $TiO_2/SiO_2$ composite fine particles; matrix particles were the aggregates of $SiO_2$ particles having a band gap energy of about 6.2 eV and a refractive index of about 146; and daughter particles comprise $TiO_2$ particles having a band gap energy of about 3.3 eV and a refractive index of about 2.71.

The amount of the daughter particles in the above composite fine particles was about 22.3% by volume, which was calculated based on the compositional ratio of particles in the starting material liquid mixture and the amount of $SiO_2$ coating, wherein particle densities of $SiO_2$ and $TiO_2$ were 2.27 g/cm$^3$ and 3.84 g/cm$^3$, respectively. The refractive index of the composite fine particles was about 1.74, the refractive index being calculated from the amount of the daughter particles in the composite fine particles. Incidentally, the amount of the daughter particles dispersed in and supported by aggregates of the matrix particles, which did not include the $SiO_2$ coating layer portion, was about 35.0% by volume.

The composite fine particles before the water-repellent treatment were diluted in white vaseline (manufactured by Wako Pure Chemical Industries, Ltd.), so as to have a concentration of the $TiO_2$ particles of 1% by weight in a mixture comprising white vaseline and the composite fine particles. Thereafter, the determination of color change was carried out in the same manner as in Example 1. The above showed that no color change took place in the white vaseline, and that the catalytic activities were substantially inhibited in the resulting composite fine particles.

Figure 12:
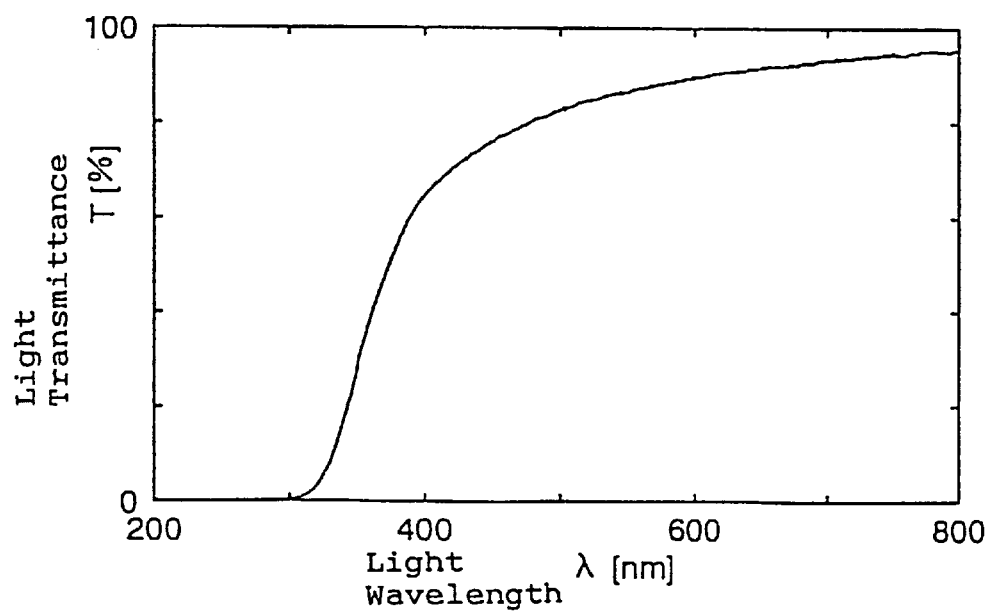
FIG. 12 is a graph showing the relationship between light wavelength and light transmittance of the ultraviolet shielding composite fine particles obtained in Example 12, as measured by an ultraviolet-visible light spectrophotometer.

After 0.13 g of the silicone oil dispersion of the composite fine particles obtained above was diluted with 9.87 g of the silicone oil ("KP96A" used above), the light transmittance of the resulting liquid dispersion was evaluated in the same manner as in Example 1. The results are shown in FIG. 12.

In the figure, the light transmittance of the composite fine particles was substantially equal to 0% in the ultraviolet region B and the ultraviolet region C, the wavelengths of which were not longer than 300 nm. On the other hand, the composite fine particles show extremely high light transmittance values in the entire visible light region at a wavelength of from 400 to 800 nm, the light transmittance at 400 nm being 65%, and at 800 nm being 95%. Accordingly, the composite fine particles thus produced had a high transparency in the visible light region and a high shielding ability in the ultraviolet region.

EXAMPLE 13

The formation of the $TiO_2/SiO_2$ composite fine particles and the $SiO_2$ surface-coating treatment were carried out in the same manner as in Example 11.

After the coating step was completed, a mixed solution of 0.39 ml of 4 N-sodium hydroxide aqueous solution and 20 g of ethanol was added to the reaction mixture to neutralize the hydrochloric acid. All of the above steps were carried out under stirring.

While stirring the liquid dispersion obtained above, a mixed solution comprising 0.6 g of a polyvinyl pyrrolidone ("K-30," for cosmetics, manufactured by Wako Pure Chemical Industries, Ltd.) dissolved in 30 g of ethanol was added dropwise, and the mixed solution was blended with the liquid dispersion. Thereafter, a water-repellent treatment for the $TiO_2/SiO_2$ composite fine particles was carried out by the steps of adding dropwise a mixed solution of 3.0 g of an oxazoline-modified silicone ("OS96-20," manufactured by Kao Corporation) and 860 g of ethanol and mixing the mixed solution with the liquid dispersion.

The liquid dispersion thus obtained was subjected to a topping treatment at 75° C. using a rotary evaporator to remove ethanol and water, to thereby produce a liquid dispersion which was concentrated five times that of the liquid dispersion before the topping treatment.

While stirring the liquid dispersion obtained above, 575 g of a silicone oil ("SH244," manufactured by Toray-Dow Corning Corporation; refractive index: 139) was added dropwise, and mixed with the liquid dispersion. Thereafter, the resulting liquid dispersion was subjected to a topping treatment at 80° C. using a rotary evaporator to remove ethanol and water.

The resulting liquid dispersion was subjected to a dispersion treatment using a homogenizer for one hour. Thereafter, the resulting mixture was subjected to a topping treatment at 80° C. using a rotary evaporator to remove ethanol, water, and a silicone oil, so that the composite fine particles were phase-transferred and dispersed in the silicone oil, to give a silicone oil dispersion of the composite fine particles having a concentration of the composite fine particles of 25% by weight.

After the coating treatment, the liquid dispersion was subjected to a solid-liquid separation in the same manner as in Example 1, to give an ethanol containing-cake of the composite fine particles. Thereafter, the particle diameter of the composite fine particles before the water-repellent treatment was measured by dispersing the ethanol-containing cake of the composite fine particles in water and obtaining the particle diameter using a laser-doppler type particle size analyzer ("DLS-700," manufactured by OTSUKA ELECTRONICS CO., LTD.). It was found that the average particle diameter, based on volume, was about 0.08 μm.

After the water-repellent treatment, a cross section of the composite fine particles was observed by a transmission electron microscope (JEM-2000FX, manufactured by JEOL Ltd.) using an ultrathin sectioning method. Consequently, it was found that $TiO_2$ ultrafine particles (average particle diameter: about 0.01 μm) were dispersed in and supported by aggregates of $SiO_2$ ultrafine particles (average particle diameter: about 0.01 μm). In other words, the composite fine particles were $TiO_2/SiO_2$ composite fine particles; matrix particles were the aggregates of $SiO_2$ particles having a band gap energy of about 6.2 eV and a refractive index of about 1.46; and daughter particles comprise $TiO_2$ particles having a band gap energy of about 3.3 eV and a refractive index of about 2.71.

The amount of the daughter particles in the above composite fine particles was about 22.3% by volume, which was calculated based on the compositional ratio of particles in the starting material liquid mixture and the amount of $SiO_2$ coating, wherein particle densities of $SiO_2$ and $TiO_2$ were 2.27 g/cm$^3$ and 3.84 g/cm$^3$, respectively. The refractive index of the composite fine particles was about 1.74, the refractive index being calculated from the amount of the daughter particles in the composite fine particles. Incidentally, the amount of the daughter particles dispersed in and supported by aggregates of the matrix particles, which did not include the $SiO_2$ coating layer portion, was about 35.0% by volume.

The composite fine particles before the water-repellent treatment were diluted in white vaseline (manufactured by Wako Pure Chemical Industries, Ltd.), so as to have a concentration of the $TiO_2$ particles of 1% by weight in a mixture comprising white vaseline and the composite fine particles. Thereafter, the determination of color change was carried out in the same manner as in Example 1. The above showed that no color change took place in the white vaseline, and that the catalytic activities were substantially inhibited in the resulting composite fine particles.

Figure 13:
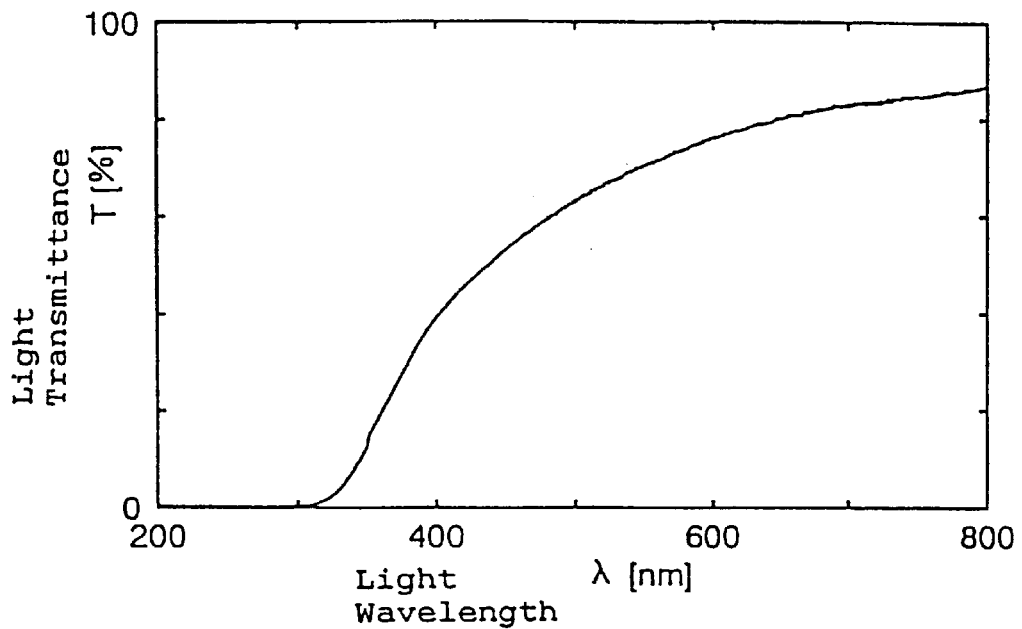
FIG. 13 is a graph showing the relationship between light wavelength and light transmittance of the ultraviolet shielding composite fine particles obtained in Example 13, as measured by an ultraviolet-visible light spectrophotometer.

After 0.08 g of the silicone oil dispersion of the composite fine particles obtained above was diluted with 9.92 g of the silicone oil ("KP96A" used above), the light transmittance of the resulting liquid dispersion was evaluated in the same manner as in Example 1. The results are shown in FIG. 13.

In the figure, the light transmittance of the composite fine particles was substantially equal to 0% in the ultraviolet region B and the ultraviolet region C, the wavelengths of which were not longer than 300 nm. On the other hand, the composite fine particles show extremely high light transmittance values in the entire visible light region at a wavelength of from 400 to 800 nm, the light transmittance at 400 nm being 39%, and at 800 nm being 87%. Accordingly, the composite fine particles thus produced had a high transparency in the visible light region and a high shielding ability in the ultraviolet region.

EXAMPLE 14

The formation of the $TiO_2/SiO_2$ composite fine particles and the $SiO_2$ surface-coating treatment were carried out in the same manner as in Example 11.

After the coating step was completed, a mixed solution of 0.39 ml of 4 N-sodium hydroxide aqueous solution and 20 g of ethanol was added to the reaction mixture to neutralize the hydrochloric acid. All of the above steps were carried out under stirring.

While stirring the liquid dispersion obtained above, a mixed solution comprising 0.6 g of a polyvinyl pyrrolidone ("K-30," for cosmetics, manufactured by Wako Pure Chemical Industries, Ltd.) dissolved in 30g of ethanol was added dropwise, and the mixed solution was blended with the liquid dispersion. Thereafter, a water-repellent treatment for the $TiO_2/SiO_2$ composite fine particles was carried out by the steps of adding dropwise a mixed solution of 3.0 g of an oxazoline-modified silicone ("OS96-20," manufactured by Kao Corporation) and 860 g of ethanol and blending the mixed solution with the liquid dispersion.

The liquid dispersion obtained above was subjected to a drying treatment at 80° C., to thereby dry the composite fine particles. The resulting powder was pulverized twice using a mill ("A10," manufactured by IKA-Labourtechnik), to give the composite fine particles.

After the coating treatment, the liquid dispersion was subjected to a solid-liquid separation in the same manner as in Example 1, to give an ethanol containing-cake of the composite fine particles. Thereafter, the particle diameter of the composite fine particles before the water-repellent treatment was measured by dispersing the ethanol-containing cake of the composite fine particles in water and obtaining the particle diameter using a laser-doppler type particle size analyzer ("DLS-700," manufactured by OTSUKA ELECTRONICS CO., LTD.). It was found that the average particle diameter, based on volume, was about 0.08 μm.

After the water-repellent treatment, a cross section of the composite fine particles was observed by a transmission electron microscope (JEM-2000FX, manufactured by JEOL Ltd.) using an ultrathin sectioning method. Consequently, it was found that $TiO_2$ ultrafine particles (average particle diameter: about 0.01 μm) were dispersed in and supported by aggregates of $SiO_2$ ultrafine particles (average particle diameter: about 0.01 μm). In other words, the composite fine particles were $TiO_2/SiO_2$ composite fine particles; matrix particles were the aggregates of $SiO_2$ particles having a band gap energy of about 6.2 eV and a refractive index of about 1.46; and daughter particles comprise $TiO_2$ particles having a band gap energy of about 3.3 eV and a refractive index of about 2.71.

The amount of the daughter particles in the above composite fine particles was about 22.3% by volume, which was calculated based on the compositional ratio of particles in the starting material liquid mixture and the amount of $SiO_2$ coating, wherein particle densities of $SiO_2$ and $TiO_2$ were 2.27 g/cm$^3$ and 3.84 g/cm$^3$, respectively. The refractive index of the composite fine particles was about 1.74, the refractive index being calculated from the amount of the daughter particles in the composite fine particles. Incidentally, the amount of the daughter particles dispersed in and supported by aggregates of the matrix particles, which did not include the $SiO_2$ coating layer portion, was about 35.0% by volume.

The composite fine particles before and after the water-repellent treatment were diluted in white vaseline (manufactured by Wako Pure Chemical Industries, Ltd.), so as to have a concentration of the $TiO_2$ particles of 1% by weight in a mixture comprising white vaseline and the composite fine particles. Thereafter, the determination of color change was carried out in the same manner as in Example 1. The above showed that no color change took place in the white vaseline, and that the catalytic activities were substantially inhibited in the resulting composite fine particles.

After the water-repellent treatment, when the composite fine particles were mixed with water, they showed a strong water repellent property. When the composite fine particles were mixed with a silicone oil ("SH244," manufactured by Toray-Dow Corning Corporation; refractive index: 1.39), the composite fine particles were rapidly dispersed in the silicone oil.

Figure 14:
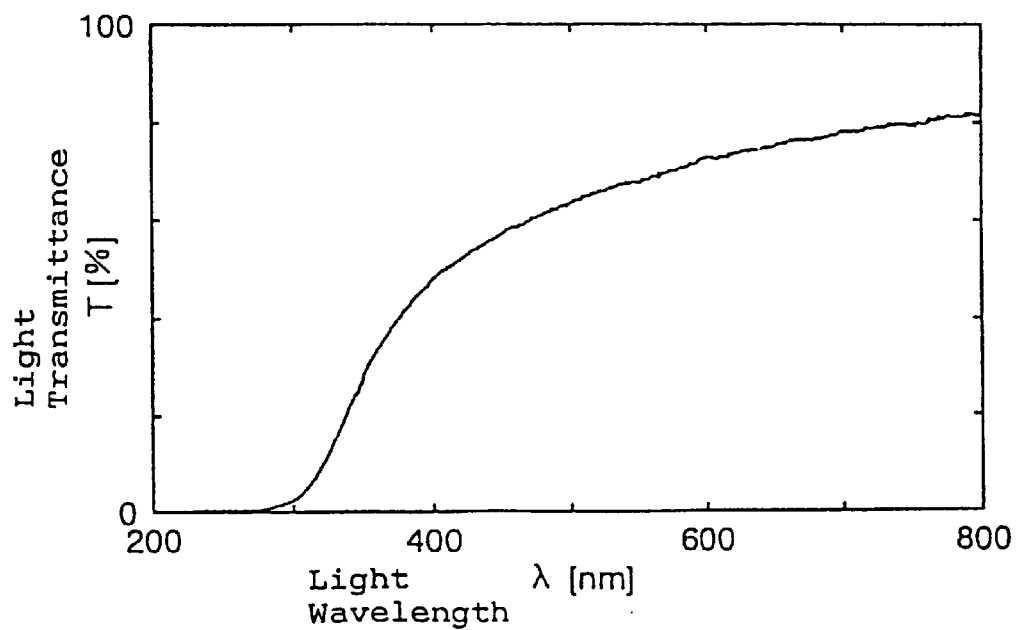
FIG. 14 is a graph showing the relationship between light wavelength and light transmittance of the ultraviolet shielding composite fine particles obtained in Example 14, as measured by an ultraviolet-visible light spectrophotometer.

Ten mg of the composite fine particles having the above refractive index was dispersed in 10 g of the above silicone oil. The light transmittance of the resulting liquid dispersion was evaluated in the same manner as in Example 1. The results are shown in FIG. 14.

In the figure, the light transmittance of the composite fine particles was not more than 3% in the ultraviolet region B, the wavelength of which was not longer than 300 nm, and it was substantially equal to 0% in the ultraviolet region C, the wavelength of which was not longer than 260 nm. On the other hand, the composite fine particles show extremely high light transmittance values in the entire visible light region at a wavelength of from 400 to 800 nm, the light transmittance at 400 nm being 48%, and at 800 nm being 82%. Accordingly, the composite fine particles thus produced had a high transparency in the visible light region and a high shielding ability in the ultraviolet region.

EXAMPLE 15

61.0 g of a silica sol ("ST-C," manufactured by Nissan Chemical Industries, Ltd.; $SiO_2$ concentration: 20.5% by weight) and 87.5 g of titanium oxide ultrafine particles ("MT-600B," manufactured by TAYCA CORPORATION; rutile-type) were mixed. To the mixture, water was added to make up a volume of one liter, yielding a starting material liquid mixture. Specifically, the concentrations of $SiO_2$ and $TiO_2$ in the starting material liquid mixture were 0.21 mol/liter and 1.10 mol/liter, respectively, and the amount of the daughter-and-matrix particle mixture contained in the above starting material liquid mixture was about 10% by weight.

The above starting material liquid mixture thus prepared was subjected to a pretreatment using a homogenizer ("T.K.-ROBOMICS," manufactured by Tokushu Kika Kogyo Co., Ltd.) at 12000 r.p.m. for 90 minutes. Thereafter, while agitating at 7000 r.p.m., the pretreated starting material liquid mixture was further subjected to a dispersion treatment for 30 minutes using a dynomill ("KDL-PILOT," manufactured by Willy A. Bachofen AG) under the conditions of an agitation speed of 3600 r.p.m. and a solution/media ratio of 600 cc/1200 cc, for 8 minutes, the treatment procedure being repeated two more times, to give a liquid dispersion containing $TiO_2/SiO_2$ ultrafine aggregates comprising $TiO_2$ as the daughter particles and $SiO_2$ as the matrix particles.

188 g of the above liquid dispersion was subjected to a topping treatment using a rotary evaporator to remove water, to thereby produce a liquid dispersion which was concentrated about three times that of the liquid dispersion before the topping treatment. Thereafter, while agitating with a homogenizer ("T.K.-ROBOMICS" used above), the liquid dispersion was added dropwise to and dispersed in 1300 g of ethanol. Further, the resulting liquid dispersion was subjected to a dispersion treatment using an ultrasonic disperser for 30 minutes. Subsequently, a mixture comprising 32.6 g of tetraethoxysilane dissolved in 100 g ethanol was added and mixed with the above liquid dispersion, and the contents were heated to 50° C. in a water bath. After the temperature of the resulting mixture reached 50° C., a mixed solution of 1.56 ml of 1 N-hydrochloric acid and 600 g of ethanol was added dropwise to the liquid dispersion. After the dropwise addition was completed, the mixture was allowed to react with one another at 50° C. for 2 hours and 30 minutes, to thereby surface-coat the composite fine particles with $SiO_2$. All of the above steps were carried out under stirring.

After the coating treatment was completed, a mixed solution of 0.39 ml of 4 N-sodium hydroxide aqueous solution and 20 g of ethanol was added to the reaction mixture to neutralize the hydrochloric acid. All of the above steps were carried out under stirring.

While stirring the liquid dispersion obtained above, a water-repellent treatment for the $TiO_2/SiO_2$ composite fine particles was carried out by the steps of adding dropwise a mixed solution comprising 2.9 g of an oxazoline-modified silicone ("OS96-20," manufactured by Kao Corporation) dissolved in 842 g of ethanol and blending the mixed solution with the liquid dispersion.

The liquid dispersion thus obtained was further subjected to a topping treatment at 75° C. using a rotary evaporator to remove ethanol and water, to thereby produce a liquid dispersion which was concentrated about five times that of the liquid dispersion before the topping treatment.

While stirring the liquid dispersion obtained above, 582.8 g of a silicone oil ("SH244," manufactured by Toray-Dow Corning Corporation; refractive index: 1.39) was added dropwise, and mixed with the liquid dispersion. Thereafter, the resulting liquid dispersion was subjected to a topping treatment at 80° C. using a rotary evaporator to remove ethanol and water.

The resulting liquid dispersion was subjected to a dispersion treatment using a homogenizer for one hour. Thereafter, the resulting mixture was subjected to a topping treatment at 80° C. using a rotary evaporator to remove ethanol, water, and a silicone oil, so that the composite fine particles were phase-transferred and dispersed in the silicone oil, to give a silicone oil dispersion of the composite fine particles having a concentration of the composite fine particles of 25% by weight.

After the coating treatment, the liquid dispersion was subjected to a solid-liquid separation in the same manner as in Example 1, to give an ethanol containing-cake of the composite fine particles. Thereafter, the particle diameter of the composite fine particles before the water-repellent treatment was measured by dispersing the ethanol-containing cake of the composite fine particles in water and obtaining the particle diameter using a laser-doppler type particle size analyzer ("DLS-700," manufactured by OTSUKA ELECTRONICS CO., LTD.). It was found that the average particle diameter, based on volume, was about 0.10 $\mu$m.

After the water-repellent treatment, a cross section of the composite fine particles was observed by a transmission electron microscope (JEM-2000FX, manufactured by JEOL Ltd.) using an ultrathin sectioning method. Consequently, it was found that $TiO_2$ ultrafine particles (average particle diameter: about 0.01 $\mu$m) were dispersed in and supported by aggregates of $SiO_2$ ultrafine particles (average particle diameter: about 0.01 $\mu$m). In other words, the composite fine particles were $TiO_2/SiO_2$ composite fine particles; matrix particles were the aggregates of $SiO_2$ particles having a band gap energy of about 6.2 eV and a refractive index of about 1.46; and daughter particles comprise $TiO_2$ particles having a band gap energy of about 3.3 eV and a refractive index of about 2.71.

The amount of the daughter particles in the above composite fine particles was about 45.3% by volume, which was calculated based on the compositional ratio of particles in the starting material liquid mixture and the amount of $SiO_2$ coating, wherein particle densities of $SiO_2$ and $TiO_2$ were 2.27 g/cm$^3$ and 3.84 g/cm$^3$, respectively. The refractive index of the composite fine particles was about 2.03, the refractive index being calculated from the amount of the daughter particles in the composite fine particles. Incidentally, the amount of the daughter particles dispersed in and supported by aggregates of the matrix particles, which did not include the $SiO_2$ coating layer portion, was about 80.5% by volume.

The composite fine particles before the water-repellent treatment were diluted in white vaseline (manufactured by Wako Pure Chemical Industries, Ltd.), so as to have a concentration of the $TiO_2$ particles of 1% by weight in a mixture comprising white vaseline and the composite fine particles. Thereafter, the determination of color change was carried out in the same manner as in Example 1. The above showed that no color change took place in the white vaseline, and that the catalytic activities were substantially inhibited in the resulting composite fine particles.

Figure 15:
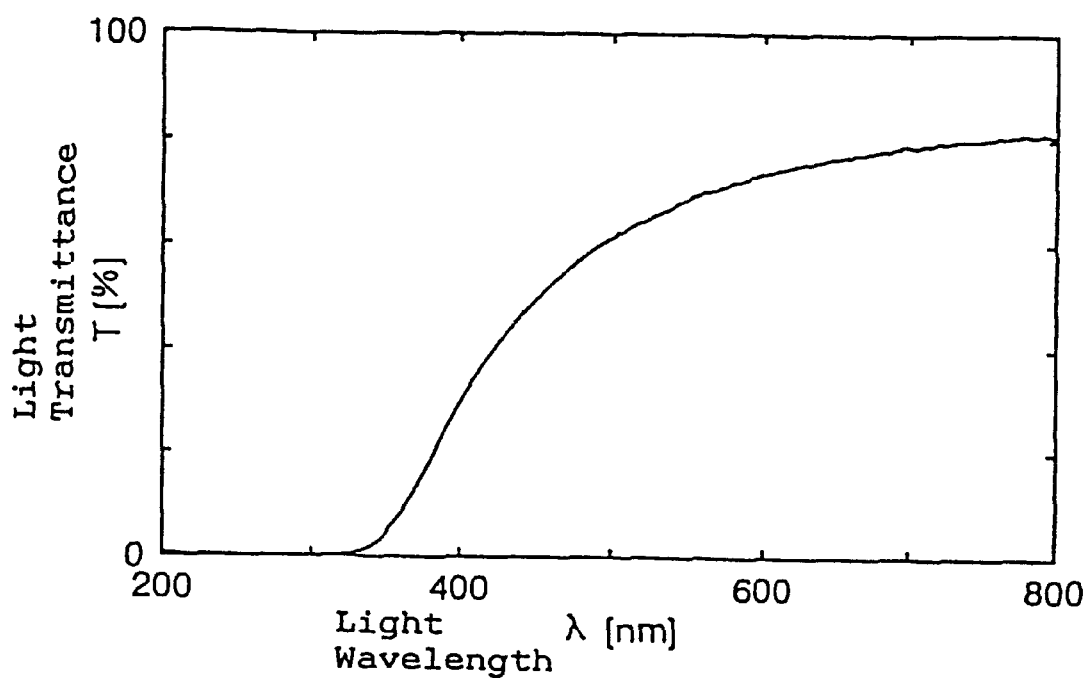
FIG. 15 is a graph showing the relationship between light wavelength and light transmittance of the ultraviolet shielding composite fine particles obtained in Example 15, as measured by an ultraviolet-visible light spectrophotometer.

After 0.046 g of the silicone oil dispersion of the composite fine particles obtained above was diluted with 9.954 g of the silicone oil ("KP96A" used above), the light transmittance of the resulting liquid dispersion was evaluated in the same manner as in Example 1. The results are shown in FIG. 15.

In the figure, the light transmittance of the composite fine particles was substantially equal to 0% in the ultraviolet region B and the ultraviolet region C, the wavelengths of which were not longer than 300 nm. On the other hand, the composite fine particles show high light transmittance values in the entire visible light region at a wavelength of from 400 to 800 nm, the light transmittance at 400 nm being 30%, and at 800 nm being 81%. Accordingly, the composite fine particles thus produced had a high transparency in the visible light region and a high shielding ability in the ultraviolet region.

EXAMPLE 16 (Lotion)

| Ingredients | Amount (weight %) |
| --- | --- |
| Ethanol | 30.0 |
| Glycerol | 5.0 |
| Polyethylene glycol 1500 | 4.0 |
| Polyoxyethylene(20) oleyl ether | 1.0 |
| Polyoxyethylene(30) hydrogenated castor oil | 0.5 |
| Composite Fine Particles (Produced in Example 2) | 10.0 |
| Urocanic acid | 2.0 |
| Perfume | 0.2 |
| Distilled Water | Balance |

The lotion having the above composition was evaluated with respect to SPF using an SPF analyzer. As a result, SPF was 3.0 and PFA was 1.5. It was found that skin after lotion application was free from unnatural whitening, showing that the cosmetics had an excellent ultraviolet shielding effect.

EXAMPLE 17 (Emulsion)

| Ingredients | Amount (weight %) |
| --- | --- |
| Cetanol | 1.0 |
| Squalane | 2.0 |
| Olive Oil | 5.0 |
| Octyl methoxycinnamate | 4.0 |
| Polyoxyethylene(10) hydrogenated castor oil | 1.0 |
| Sorbitan monostearate | 1.0 |
| Dispersion Oil Containing Composite Fine Particles (Produced in Example 3) | 25.0 |
| Butyl p-hydroxybenzoate | 0.1 |
| Methyl p-hydroxybenzoate | 0.1 |
| Ethanol | 3.0 |
| Glycerol | 2.0 |
| 1,3-Butylene glycol | 2.0 |
| Perfume | 0.1 |
| Distilled Water | Balance |

The emulsion having the above composition was evaluated with respect to SPF using an SPF analyzer. As a result, SPF was 15.9 and PFA was 5.0. It was found that skin after emulsion application was free from unnatural whitening, showing that the cosmetics had an excellent ultraviolet shielding effect.

EXAMPLE 18 (Emulsion)

| Ingredients | Amount (weight %) |
| --- | --- |
| Dispersion Oil Containing Composite Fine Particles (Produced in Example 3) | 30.0 |
| Dimethylsiloxane-methyl (polyoxyethylene)-siloxane copolymer | 3.5 |
| Octamethyltetracyclosiloxane | 20.0 |
| Organopolysiloxane B | 1.0 |
| Squalane | 2.0 |
| Octyldodecyl myristate | 1.0 |
| Butyl p-hydroxybenzoate | 0.1 |
| Methyl p-hydroxybenzoate | 0.1 |
| Glycerol | 5.0 |
| Perfume | 0.1 |
| Distilled Water | Balance |

The emulsion having the above composition was evaluated with respect to SPF using an SPF analyzer. As a result, SPF was 2.5 and PFA was 1.2. It was found that skin after emulsion application was free from unnatural whitening, showing that the cosmetics had an excellent ultraviolet shielding effect.

EXAMPLE 19 (Cream)

| Ingredients | Amount (weight %) |
| --- | --- |
| Stearic Acid | 2.0 |
| Cetanol | 1.0 |
| Cholesterol | 1.0 |
| Squalane | 5.0 |
| Olive Oil | 5.0 |
| Octyl methoxycinnamate | 4.0 |
| Cetyl phosphate | 0.5 |
| Sorbitan monostearate | 2.0 |
| Polyoxyethylene(40) hydrogenated castor oil | 0.5 |
| Composite Fine Particles (Produced in Example 4) | 15.0 |
| Titanium Oxide Fine Particles | 2.0 |

EXAMPLE 20 (Cream)

| Ingredients | Amount (weight %) |
| --- | --- |
| Dispersion Oil Containing Composite Fine Particles (Produced in Example 4) | 20.0 |
| Dimethylsiloxane-methyl (polyoxyethylene) siloxane copolymer | 4.0 |
| Methyl polysiloxane (6 cSt) | 5.0 |
| 2-Ethylhexyl p-methoxycinnamate | 3.0 |
| 4-Methoxy-4'-t-butylbenzoyl methane | 2.0 |
| Octamethyl tetracyclosiloxane | 10.0 |
| Squalane | 2.0 |
| Octyldodecyl myristate | 1.0 |
| Magnesium sulfate | 0.5 |
| Butyl p-hydroxybenzoate | 0.1 |
| Methyl p-hydroxybenzoate | 0.1 |
| Glycerol | 6.0 |
| Diglycerol | 2.0 |
| Polymethyl silsesquioxane powder | 4.0 |
| Perfume | 0.1 |
| Distilled Water | Balance |

*(continued from previous page)*

| Ingredients | Amount (weight %) |
| --- | --- |
| Butyl p-hydroxybenzoate | 0.1 |
| Methyl p-hydroxybenzoate | 0.1 |
| Glycerol | 10.0 |
| L-Arginine | 0.3 |
| Perfume | 0.1 |
| Distilled Water | Balance |

The cream having the above composition was evaluated with respect to SPF using an SPF analyzer. As a result, SPF was 18.5 and PFA was 7.2. It was found that skin after cream application was free from unnatural whitening, showing that the cosmetics had an excellent ultraviolet shielding effect.

The cream having the above composition was evaluated with respect to SPF using an SPF analyzer. As a result, SPF was 23.0 and PFA was 12.2. It was found that skin after cream application was free from unnatural whitening, showing that the cosmetics had an excellent ultraviolet shielding effect.

EXAMPLE 21 (Aerosol Cosmetics)

| Ingredients | Amount (weight %) |
| --- | --- |
| Triclosan | 0.01 |
| Aluminum hydroxychloride | 1.5 |
| Talc | 1.0 |
| Composite Fine Particles (Produced in Example 2) | 5.0 |
| Isopropyl myristate | 2.0 |
| Perfume | 0.2 |
| Propellant | Balance |

The aerosol cosmetics having the above composition were evaluated with respect to SPF using an SPF analyzer. As a result, SPF was 1.4 and PFA was 1.2. Also, it was found that the cosmetics had an excellent ultraviolet shielding effect.

EXAMPLE 22 (Powdery Foundation)

| | Ingredients | Amount (weight %) |
| --- | --- | --- |
| (1) | Composite Fine Particles (Produced in Example 3) | 10.0 |
| (2) | Fluorine Compound-Treated (*1) Mica | Balance |
| (3) | Fluorine Compound-Treated (*1) Talc | 20.0 |
| (4) | Fluorine Compound-Treated (*1) Titanium Oxide | 8.0 |
| (5) | Fluorine Compound-Treated (*1) Iron Oxide (Red, Yellow, Black) | 3.0 |
| (6) | Fluorine Compound-Treated (*1) Zinc Oxide Fine Particles | 2.0 |
| (7) | Fluorine Compound-Treated (*1) Titanium Oxide Fine Particles (Average, Particle Diameter: 35 nm) | 1.0 |
| (8) | Fluorine Compound-Treated (*1) Nylon Powder | 10.0 |
| (9) | Methyl polysiloxane (10 cSt) | 4.0 |
| (10) | Perfluoropolyether ("FOMBLIN HC-04," manufactured by AUSIMONT CO.) | 8.0 |
| (11) | Hydrogenated Oil (Synchrowax) | 1.0 |
| (12) | Octyl methoxycinnamate | 1.0 |
| (13) | Antiseptics, Perfume | 1.0 |

Note
(*1): Treatment was carried out by coating with 2% by weight of perfluoroalkyl ethyl phosphate.

Ingredients (1) to (8) were blended in a Henschel mixer. Ingredients (9) to (13) subjected to blending and heating at 80° C. in advance were added to the mixture comprising the ingredients (1) to (8). The resulting mixture was pulverized using a pulverizer. A given amount of the pulverized product was taken out on a metallic pan and pressed by a pressing machine, to give a powdery foundation.

The resulting powdery foundation had remarkably advantageous effects in shielding ultraviolet light and had good spreadability, giving natural feeling after application.

EXAMPLE 23 (Two-Way Powdery Foundation)

| | Ingredients | Amount (weight %) |
| --- | --- | --- |
| (1) | Composite Fine Particles (Produced in Example 2) | 20.0 |
| (2) | Silicone-Treated (*2) Mica | Balance |
| (3) | Silicone-Treated (*2) Talc | 20.0 |
| (4) | Silicone-Treated (*2) Titanium Oxide | 9.0 |
| (5) | Silicone-Treated (*2) Iron Oxide Red, Yellow, Black) | 4.0 |
| (6) | Silicone-Treated (*2) Zinc Oxide Fine Particles Coated with 30% by weight of Nylon Powder | 8.0 |
| (7) | Methyl polysiloxane (10,000 cSt) | 0.2 |
| (8) | Methyl polysiloxane (6 cSt) | 8.0 |
| (9) | Hydrogenated Oil (Synchrowax) | 1.0 |
| (10) | Octyl methoxycinnamate | 2.0 |
| (11) | Antiseptics, Perfume | 1.0 |

Note
(*2): Treatment was carried out by coating with 2% by weight of methylhydrogenpolysiloxane.

Ingredients (1) to (6) were blended in a Henschel mixer. Ingredients (7) to (11) subjected to blending and heating at 80° C. in advance were added to the mixture comprising the ingredients (1) to (6). The resulting mixture was pulverized using a pulverizer. A given amount of the pulverized product was taken out on a metallic pan, and pressed by a pressing machine, to give a two-way cake-foundation.

The resulting cake-foundation had remarkably advantageous effects in shielding ultraviolet light and had good spreadability, and natural feeling after application.

EXAMPLE 24 (Powdery Eye Shadow)

| | Ingredients | Amount (weight %) |
|---|---|---|
| (1) | Dispersion Oil Containing Composite Fine Particles (Produced in Example 5) | 11.0 |
| (2) | Lecithin-Treated (*3) Mica | Balance |
| (3) | Lecithin-Treated (*3) Titanated Mica | 6.0 |
| (4) | Silicone-Treated (*4) Ultramarine | 8.0 |
| (5) | Silicone-Treated (*4) Prussian blue | 10.0 |
| (6) | Silicone-Treated (*4) Iron Oxide (Red, Yellow, Black) | 2.0 |
| (7) | Spherical Silicone Resin Powder ("TOSPEARL 145," manufactured by Toshiba Silicone Corpation) | 10.0 |
| (8) | Diisostearyl malate | 3.0 |
| (9) | Hydrogenated Oil (Synchrowax) | 0.5 |
| (10) | Vaseline | 1.0 |
| (11) | Antiseptics, Perfume | 1.0 |

Notes
(*3): Treatment was carried out by coating with 5% by weight of soybean lecithin.
(*4): Treatment was carried out by coating with 2% by weight of methylhydrogenpolysiloxane.

Ingredients (1) to (7) were blended in a Henschel mixer. Ingredients (8) to (11) subjected to blending and heating at 80° C. in advance were added to the mixture comprising the ingredients (1) to (7). The resulting mixture was pulverized using a pulverizer. A given amount of the pulverized product was taken out on a metallic pan, and pressed by a pressing machine, to give a powdery eye shadow.

The resulting powdery eye shadow had remarkably advantageous effects in shielding the ultraviolet light and had good spreadability, and provided good coloring to the skin.

EXAMPLE 25 (Emulsion Type's Foundation)

| | Ingredients | Amount (weight %) |
|---|---|---|
| (1) | Dispersion Oil Containing Composite Fine Particles (Produced in Example 7) | 25.0 |
| (2) | Silicone-Treated (*5) Titanium Oxide | 3.0 |
| (3) | Silicone-Treated (*5) Iron Oxide (Red, Yellow, Black) | 1.5 |
| (4) | Silicone-Treated (*5) Zinc Oxide Fine Particles | 3.0 |
| (5) | Dimethylcyclopolysiloxane | 10.0 |
| (6) | Octyl methoxycinnamate | 2.0 |
| (7) | Dimethylsiloxane-methylpolyoxyethylene-siloxane copolymer | 1.0 |
| (8) | Glycerol | 2.0 |
| (9) | Ethanol | 10.0 |
| (10) | Distilled water | Balance |

Notes
(*5): Treatment was carried out by coating with 2% by weight of methylhydrogenpolysiloxane.

Ingredients (1) to (4) were blended in a Henschel mixer. Ingredients (5) to (7) were separately blended, and the mixture comprising the ingredients (1) to (4) blended in advance was added to a mixture comprising the ingredients (5) to (7), and the obtained mixture was dispersed with a stirrer. A mixture comprising ingredients (8) to (10) was gradually added over a period of 30 minutes to the above dispersed mixture while stirring. The obtained mixture containing all ingredients listed above was then emulsified by stirring with a homomixer for 10 minutes. The obtained emulsion was defoamed, and then filled into a bottle to give an emulsion type's foundation.

The resulting emulsion type's foundation had remarkably advantageous effects in shielding ultraviolet light and had good spreadability, and natural feeling after application.

EXAMPLE 26 (Lipstick)

| | Ingredients | Amount (weight %) |
|---|---|---|
| (1) | Dispersion Oil Containing Composite Fine Particles (Produced in Example 8) | 11.0 |
| (2) | Silicone-Treated (*6) Pigment Red 57-1 | 1.0 |
| (3) | Silicone-Treated (*6) Pigment Red 57 | 2.0 |
| (4) | Silicone-Treated (*6) Acid Yellow 23 Aluminum Lake | 1.0 |
| (5) | Silicone-Treated (*6) Titanium Oxide | 1.0 |
| (6) | Paraffin wax | 5.0 |
| (7) | Candelilla wax | 10.0 |
| (8) | Carnauba wax | 9.0 |
| (9) | Isopropyl isopalmitate | 20.0 |
| (10) | Isononyl isononanate | 15.0 |
| (11) | Isostearyl malate | 20.0 |
| (12) | Methyl polysiloxane (1000 cSt) | 5.0 |

Note
(*6): Treatment was carried out by coating with 2% by weight of methylhydrogenpolysiloxane.

Ingredients (1) to (12) were heated to 80° C. and blended to give a homogeneous mixture, and the obtained mixture was cooled to a temperature of 30° C. The cooled mixture was sufficiently blended with a triple roller, and then reheated to 80° C. The obtained mixture was casted into a mold and then solidified by cooling to give a lipstick.

The resulting lipstick had remarkably advantageous effects in shielding ultraviolet light and had good spreadability, thus providing good coloring to the lip. Incidentally, in the case where the oil used for the dispersion oil containing the composite fine particles produced in Example 8 was changed from a silicone oil to an ester oil (diisostearyl malate: "COSMOL 222," manufactured by The Nisshin Oil Mills, Ltd.), substantially the same level of the ultraviolet shielding effects can be obtained.

In the following Examples and Comparative Examples, the following five kinds of ether-modified silicones were used, but the ether-modified silicones in the present invention are not limited thereto.

(i) Ether-modified Silicone A:
Dimethylsiloxane-methyl (polyoxyethylene)siloxane copolymer represented by the general formula (3), with proviso that $R^{11}$ and $R^{12}$ both stand for methyl groups; $R^{13}$ stands for $H(OC_3H_6)_b(OC_2H_4)_aO(CH_2)_p$—, wherein "a" is a number of from 7 to 15, "b" is equal to 0, and "p" is equal to 3; "m" is a number of from 50 to 100; and "n" is a number of from 1 to 5.

(ii) Ether-modified Silicone B:
Dimethylsiloxane-methyl (polyoxyethylene)siloxane copolymer represented by the general formula (3), with proviso that $R^{11}$ and $R^{12}$ both stand for methyl groups; $R^{13}$ stands for $H(OC_3H_6)_b(OC_2H_4)_aO(CH_2)_p$—, wherein "a" is a number of from 2 to 5, "b" is equal to 0, and "p" is equal to 3; "m" is a number of from 20 to 30; and "n" is a number of from 2 to 5.

(iii) Ether-modified Silicone C:
Dimethylsiloxane-methyl (polyoxyethylene)siloxane copolymer represented by the general formula (3), with proviso that $R^{11}$ and $R^{12}$ both stand for methyl groups; $R^{13}$ stands for $H(OC_3H_6)_b(OC_2H_4)_aO(CH_2)_p$—, wherein "a" is equal to 0, "b" is a number of from 7 to 13, and "p" is equal to 3; "m" is a number of from 4 to 10; and "n" is a number of from 1 to 6.

(iv) Ether-modified Silicone D:

Laurylmethycone copolyol represented by the general formula (4), wherein $R^{21}$ stands for a methyl group; $R^{22}$ stands for a dodecyl group; $R^{23}$ stands for —$(OC_2H_4)_q$ $(OC_3H_6)_r$—OH, wherein "q" is a number of from 10 to 30, and "r" is a number of from 10 to 30; Q stands for a trimethylene group; "x" is equal to 0; "y" is a number of from 30 to 70; and "z" is a number of from 1 to 6.

(v) Ether-modified Silicone E:

Alkylglycerylether-modified silicones represented by the general formula (5), with proviso that at least one of $R^{34}$ stands for —A—$OCH_2CH(OR^{41})CH_2OR^{42}$, wherein "A" stands for $C_{11}H_{23}$; and $R^{41}$ and $R^{42}$ both stand for a hydrogen atom; "s" and "t" are numbers where the sum thereof equals to 60; "u" is equal to 40.

EXAMPLE 27 (Emulsion)

| | Ingredients | Amount (weight %) |
|---|---|---|
| (1) | Cetanol | 1.0 |
| (2) | Squalane | 2.0 |
| (3) | Jojoba oil | 4.0 |
| (4) | Octyl methoxycinnamate | 4.0 |
| (5) | Polyoxyethylene(10) hydrogenated castor oil | 1.0 |
| (6) | Sorbitan monostearate | 1.0 |
| (7) | Dispersion Oil Containing Composite Fine Particles (Produced in Example 12) | 25.0 |
| (8) | Butyl p-hydroxybenzoate | 0.1 |
| (9) | Methyl p-hydroxybenzoate | 0.1 |
| (10) | Ethanol | 3.0 |
| (11) | Glycerol | 4.0 |
| (12) | Perfume | 0.05 |
| (13) | Distilled water | Balance |

The emulsion having the above composition was evaluated with respect to SPF using an SPF analyzer. As a result, SPF was 15.9 and PFA was 6.2. It was found that skin after emulsion application was free from unnatural whitening, showing that the cosmetics had an excellent ultraviolet shielding effect.

EXAMPLE 28 (Cream)

| | Ingredients | Amount (weight %) |
|---|---|---|
| (1) | Cetanol | 1.0 |
| (2) | Stearic Acid | 2.0 |
| (3) | Cholesterol | 1.0 |
| (4) | Squalane | 5.0 |
| (5) | Jojoba oil | 4.0 |
| (6) | Octyl methoxycinnamate | 4.0 |
| (7) | Polyoxyethylene(40) hydrogenated castor oil | 1.0 |
| (8) | Sorbitan monostearate | 2.0 |
| (9) | Dispersion Oil Containing Composite Fine Particles (Produced in Example 13) | 15.0 |
| (10) | Butyl p-hydroxybenzoate | 0.1 |
| (11) | Methyl p-hydroxybenzoate | 0.1 |
| (12) | Ethanol | 3.0 |
| (13) | Glycerol | 10.0 |
| (14) | Perfume | 0.05 |
| (15) | Distilled water | Balance |

The cream having the above composition was evaluated with respect to SPF using an SPF analyzer As a result, SPF was 15.7 and PFA was 6.3. It was found that skin after cream application was free from unnatural whitening, showing that the cosmetics had an excellent ultraviolet shielding effect.

EXAMPLE 29 (Emulsion Type's Foundation)

| | Ingredients | Amount (weight %) |
|---|---|---|
| (1) | Dispersion Oil Containing Composite Fine Particles (Produced in Example 13) | 25.0 |
| (2) | Silicone-Treated (*7) Titanium Oxide | 3.0 |
| (3) | Silicone-Treated (*7) Iron Oxide (Red, Yellow, Black) | 1.5 |
| (4) | Silicone-Treated (*7) Zinc Oxide Fine Particles | 3.0 |
| (5) | Dimethylcyclopolysiloxane | 10.0 |
| (6) | Octyl methoxycinnamate | 2.0 |
| (7) | Dimethylsiloxane-methylpolyoxyethylene-siloxane copolymer | 1.0 |
| (8) | Glycerol | 2.0 |
| (9) | Ethanol | 10.0 |
| (10) | Distilled water | Balance |

Notes
(*7): Treatment was carried out by coating with 2% by weight of methylhydrogenpolysiloxane.

The emulsion types foundation prepared above was evaluated with respect to SPF and PFA in the same manner as in Example 1. As a result, substantially the same or higher level of the ultraviolet shielding ability when compared to that of Example 1 was achieved.

EXAMPLE 30 (Lipstick)

| | Ingredients | Amount (weight %) |
|---|---|---|
| (1) | Dispersion Oil Containing Composite Fine Particles (Produced in Example 13) | 11.0 |
| (2) | Silicone-Treated (*8) Pigment Red 57-1 | 1.0 |
| (3) | Silicone-Treated (*8) Pigment Red 57 | 2.0 |
| (4) | Silicone-Treated (*8) Acid Yellow 23 Aluminum Lake | 1.0 |
| (5) | Silicone-Treated (*8) Titanium Oxide | 1.0 |
| (6) | Paraffin wax | 5.0 |
| (7) | Candelilla wax | 10.0 |
| (8) | Carnauba wax | 9.0 |
| (9) | Isopropyl isopalmitate | 20.0 |
| (10) | Isononyl isononanate | 15.0 |
| (11) | Isostearyl malate | 20.0 |
| (12) | Methyl polysiloxane (1000 cSt) | 5.0 |

Note
(*8): Treatment was carried out by coating with 2% by weight of methylhydrogenpolysiloxane.

The lipstick prepared above was evaluated with respect to SPF and PFA in the same manner as in Example 1. As a result, substantially the same or higher level of the ultraviolet shielding ability when compared to that of Example 1 was achieved.

EXAMPLE 31 (Water-in-Oil Type Cream)

| | Ingredients | Amount (weight %) |
|---|---|---|
| (1) | Dispersion Oil Containing Composite Fine Particles (Produced in Example 13) | 25.0 |
| (2) | Ether-modified silicone A ("SH-3775C," manufactured by Toray-Dow Corning) | 2.0 |
| (3) | α-Monomethyl-branched isostearyl glyceryl ether | 2.0 |
| (4) | Methyl polysiloxane (6 cSt) | 5.0 |
| (5) | 2-Ethylhexyl p-methoxycinnamate | 3.0 |
| (6) | Magnesium sulfate | 0.5 |

-continued

| Ingredients | | Amount (weight %) |
|---|---|---|
| (7) | Glycerol | 5.0 |
| (8) | Butyl p-hydroxybenzoate | 0.1 |
| (9) | Methyl p-hydroxybenzoate | 0.1 |
| (10) | Perfume | 0.05 |
| (11) | Distilled water | Balance |

The cream having the above composition was evaluated with respect to SPF using an SPF analyzer. As a result, SPF was 19.6 and PFA was 9.2. It was found that skin after cream application was free from unnatural whitening, showing that the cosmetics had an excellent ultraviolet shielding effect.

EXAMPLE 32 (Water-in-Oil Type Emulsion)

| Ingredients | | Amount (weight %) |
|---|---|---|
| (1) | Dispersion Oil Containing Composite Fine Particles (Produced in Example 13) | 25.0 |
| (2) | Ether-modified silicone C ("FZ-2110C," manufactured by Nippon Unicar) | 1.5 |
| (3) | Ether-modified silicone B ("KF-6015," manufactured by Shin-Etsu Silicone) | 1.5 |
| (4) | Ether-modified silicone D ("DC Q2-2500," manufactured by Toray-Dow Corning) | 1.0 |
| (5) | Methyl polysiloxane (6 cst) | 5.0 |
| (6) | Decamethyl cyclopentasiloxane | 5.0 |
| (7) | 2-Ethylhexyl p-methoxycinnamate | 3.0 |
| (8) | Squalane | 2.0 |
| (9) | Glycerol | 3.0 |
| (10) | Butyl p-hydroxybenzoate | 0.1 |
| (11) | Methyl p-hydroxybenzoate | 0.1 |
| (12) | Perfume | 0.05 |
| (13) | Distilled water | Balance |

The emulsion having the above composition was evaluated with respect to SPF using an SPF analyzer. As a result, SPF was 19.2 and PFA was 8.7. It was found that skin after emulsion application was free from unnatural whitening, showing that the cosmetics had an excellent ultraviolet shielding effect.

EXAMPLE 33 (Water-in-Oil Type Cream)

| Ingredients | | Amount (weight %) |
|---|---|---|
| (1) | Dispersion Oil Containing Composite Fine Particles (Produced in Example 12) | 20.0 |
| (2) | Ether-modified silicone E | 1.5 |
| (3) | Ether-modified silicone B ("KF-6015," manufactured by Shin-Etsu Silicone) | 0.5 |
| (4) | Methyl polysiloxane (6 cSt) | 5.0 |
| (5) | Decamethyl cyclopentasiloxane | 5.0 |
| (6) | 2-Ethylhexyl p-methoxycinnamate | 3.0 |
| (7) | 4-Methoxy-4'-t-butylbenzoylmethane | 2.0 |
| (8) | Squalane | 2.0 |
| (9) | Magnesium sulfate | 0.5 |
| (10) | Glycerol | 5.0 |
| (11) | Butyl p-hydroxybenzoate | 0.1 |
| (12) | Methyl p-hydroxybenzoate | 0.1 |
| (13) | Perfume | 0.05 |
| (14) | Distilled water | Balance |

The cream having the above composition was evaluated with respect to SPF using an SPF analyzer. As a result, SPF was 15.8 and PFA was 10.2. It was found that skin after cream application was free from unnatural whitening, showing that the cosmetics had an excellent ultraviolet shielding effect.

EXAMPLE 34 (Water-in-Oil Type Emulsion)

| Ingredients | | Amount (weight %) |
|---|---|---|
| (1) | Dispersion Oil Containing Composite Fine Particles (Produced in Example 12) | 5.0 |
| (2) | Ether-modified silicone B ("KF-6015," manufactured by Shin-Etsu Silicone) | 0.5 |
| (3) | Ether-modified silicone A ("SH-3775C," manufactured by Toray-Dow Corning) | 1.0 |
| (4) | Methyl polysiloxane (6 cst) | 5.0 |
| (5) | Decamethyl cyclopentasiloxane | 5.0 |
| (6) | 4-Methoxy-4'-t-butylbenzoylmethane | 2.0 |
| (7) | 2-Ethylhexyl p-methoxycinnamate | 3.0 |
| (8) | Squalane | 2.0 |
| (9) | Glycerol | 3.0 |
| (10) | Butyl p-hydroxybenzoate | 0.1 |
| (11) | Methyl p-hydroxybenzoate | 0.1 |
| (12) | Perfume | 0.05 |
| (13) | Distilled water | Balance |

The emulsion having the above composition was evaluated with respect to SPF using an SPF analyzer. As a result, SPF was 14.9 and PFA was 10.8. It was found that skin after emulsion application was free from unnatural whitening, showing that the cosmetics had an excellent ultraviolet shielding effect.

EXAMPLE 35 (Water-in-Oil Type Cream)

| Ingredients | | Amount (weight %) |
|---|---|---|
| (1) | Composite Fine Particles (Produced in Example 12) | 5.0 |
| (2) | Ether-modified silicone A ("SH-3775C," manufactured by Toray-Dow Corning) | 2.0 |
| (3) | α-Monomethyl-branched isostearyl glyceryl ether | 2.0 |
| (4) | Methyl polysiloxane (6 cst) | 5.0 |
| (5) | 2-Ethylhexyl p-methoxycinnamate | 3.0 |
| (6) | Magnesium sulfate | 0.5 |
| (7) | Glycerol | 5.0 |
| (8) | Butyl p-hydroxybenzoate | 0.1 |
| (9) | Methyl p-hydroxybenzoate | 0.1 |
| (10) | Perfume | 0.05 |
| (11) | Distilled water | Balance |

The cream having the above composition was evaluated with respect to SPF using an SPF analyzer. As a result, SPF was 17.5 and PFA was 6.9. It was found that skin after cream application was free from unnatural whitening, showing that the cosmetics had an excellent ultraviolet shielding effect.

EXAMPLE 36 (Water-in-Oil Type Emulsion)

| Ingredients | | Amount (weight %) |
|---|---|---|
| (1) | Composite Fine Particles (Produced in Example 12) | 5.0 |
| (2) | Ether-modified silicone C ("FZ-2110C," manufactured by Nippon Unicar) | 1.5 |
| (3) | Ether-modified silicone B ("KF-6015," manufactured by Shin-Etsu Silicone) | 1.5 |

| Ingredients | | Amount (weight %) |
|---|---|---|
| (4) | Ether-modified silicone D ("DC Q2-2500," manufactured by Toray-Dow Corning) | 1.0 |
| (5) | Methyl polysiloxane (6 cSt) | 5.0 |
| (6) | Dedamethyl cyclopentasiloxane | 5.0 |
| (7) | 2-Ethylhexyl p-methoxycinnamate | 3.0 |
| (8) | Squalane | 2.0 |
| (9) | Glycerol | 3.0 |
| (10) | Butyl p-hydroxybenzoate | 0.1 |
| (11) | Methyl p-hydroxybenzoate | 0.1 |
| (12) | Perfume | 0.05 |
| (13) | Distilled water | Balance |

The emulsion having the above composition was evaluated with respect to SPF using an SPF analyzer. As a result, SPF was 16.8 and PFA was 6.8. It was found that skin after emulsion application was free from unnatural whitening, showing that the cosmetics had an excellent ultraviolet shielding effect.

EXAMPLE 37 (Water-in-Oil Type Cream)

| Ingredients | | Amount (weight %) |
|---|---|---|
| (1) | Dispersion Oil Containing Composite Fine Particles (Produced in Example 3) | 5.0 |
| (2) | Ether-modified silicone E | 1.5 |
| (3) | Ether-modified silicone B ("KF-6015," manufactured by Shin-Etsu Silicone) | 0.5 |
| (4) | Methyl polysiloxane (6 cSt) | 5.0 |
| (5) | Decamethyl cyclopentasiloxane | 5.0 |
| (6) | 2-Ethylhexyl p-methoxycinnamate | 3.0 |
| (7) | 4-Methoxy-4'-t-butylbenzoylmethane | 2.0 |
| (8) | Squalane | 2.0 |
| (9) | Magnesium sulfate | 0.5 |
| (10) | Glycerol | 5.0 |
| (11) | Butyl p-hydroxybenzoate | 0.1 |
| (12) | Methyl p-hydroxybenzoate | 0.1 |
| (13) | Perfume | 0.05 |
| (14) | Distilled water | Balance |

The cream having the above composition was evaluated with respect to SPF using an SPF analyzer. As a result, SPF was 18.5 and PFA was 9.6. It was found that skin after cream application was free from unnatural whitening, showing that the cosmetics had an excellent ultraviolet shielding effect.

EXAMPLE 38 (Water-in-Oil Type Emulsion)

| Ingredients | | Amount (weight %) |
|---|---|---|
| (1) | Dispersion Oil Containing Composite Fine Particles (Produced in Example 4) | 5.0 |
| (2) | Ether-modified silicone B ("KF-6015," manufactured by Shin-Etsu Silicone) | 0.5 |
| (3) | Ether-modified silicone A ("SH-3775C," manufactured by Toray-Dow Corning) | 1.0 |
| (4) | Methyl polysiloxane (6 cst) | 5.0 |
| (5) | Decamethyl cyclopentasiloxane | 5.0 |
| (6) | 4-Methoxy-4'-t-butylbenzoylmethane | 2.0 |
| (7) | 2-Ethylhexyl p-methoxycinnamate | 3.0 |
| (8) | Squalane | 2.0 |
| (9) | Glycerol | 3.0 |
| (10) | Butyl p-hydroxybenzoate | 0.1 |
| (11) | Methyl p-hydroxybenzoate | 0.1 |
| (12) | Perfume | 0.05 |
| (13) | Distilled water | Balance |

The emulsion having the above composition was evaluated with respect to SPF using an SPF analyzer. As a result, SPF was 18.7 and PFA was 9.7. It was found that skin after emulsion application was free from unnatural whitening, showing that the cosmetics had an excellent ultraviolet shielding effect.

COMPARATIVE EXAMPLE 1 (Water-in-Oil Type Cream)

| Ingredients | | Amount (weight %) |
|---|---|---|
| (1) | Titanium oxide fine particles ("TTO-55(C)," manufactured by Ishihara Sangyo Kaisha, Ltd.; average particle diameter: 30 to 50 μm) | 5.0 |
| (2) | Ether-modified silicone A ("SH-3775C," manufactured by Toray-Dow Corning) | 2.0 |
| (3) | α-Monomethyl-branched isostearyl glyceryl ether | 2.0 |
| (4) | Methyl polysiloxane (6 cSt) | 5.0 |
| (5) | Decamethyl cyclopentasiloxane | 20.0 |
| (6) | 2-Ethylhexyl p-methoxycinnamate | 3.0 |
| (7) | Magnesium sulfate | 0.5 |
| (8) | Glycerol | 5.0 |
| (9) | Butyl p-hydroxybenzoate | 0.1 |
| (10) | Methyl p-hydroxybenzoate | 0.1 |
| (11) | Perfume | 0.05 |
| (12) | Distilled water | Balance |

COMPARATIVE EXAMPLE 2 (Water-in-Oil Type Cream)

| Ingredients | | Amount (weight %) |
|---|---|---|
| (1) | Titanium oxide fine particles ("TTO-51(C)," manufactured by Ishihara Sangyo Kaisha, Ltd.; average particle diameter: 10 to 30 pm) | 5.0 |
| (2) | Ether-modified silicone A ("SH-3775C," manufactured by Toray-Dow Corning) | 2.0 |
| (3) | α-Monomethyl-branched isostearyl glyceryl ether | 2.0 |
| (4) | Methyl polysiloxane (6 cSt) | 5.0 |
| (5) | Decamethyl cyclopentasiloxane | 20.0 |
| (6) | 2-Ethylhexyl p-methoxycinnamate | 3.0 |
| (7) | Magnesium sulfate | 0.5 |
| (8) | Glycerol | 5.0 |
| (9) | Butyl p-hydroxybenzoate | 0.1 |
| (10) | Methyl p-hydroxybenzoate | 0.1 |
| (11) | Perfume | 0.05 |
| (12) | Distilled water | Balance |

COMPARATIVE EXAMPLE 3 (Water-in-Oil Type Emulsion)

| Ingredients | | Amount (weight %) |
|---|---|---|
| (1) | Titanium oxide fine particles ("TTO-55(C)," manufactured by Ishihara Sangyo Kaisha, Ltd.; average particle diameter: 30 to 50 μm) | 5.0 |
| (2) | Ether-modified silicone B ("KF-6015," manufactured by Shin-Etsu Silicone) | 0.5 |
| (3) | Ether-modified silicone A ("SH-3775C," manufactured by Toray-Dow Corning) | 1.0 |
| (4) | Methyl polysiloxane (6 cSt) | 5.0 |
| (5) | Decamethyl cyclopentasiloxane | 5.0 |
| (6) | 4-Methoxy-4'-t-butylbenzoylmethane | 2.0 |
| (7) | 2-Ethylhexyl p-methoxycinnamate | 3.0 |
| (8) | Squalane | 2.0 |
| (9) | Glycerol | 3.0 |
| (10) | Butyl p-hydroxybenzoate | 0.1 |
| (11) | Methyl p-hydroxybenzoate | 0.1 |
| (12) | Perfume | 0.05 |
| (13) | Distilled water | Balance |

COMPARATIVE EXAMPLE 4 (Water-in-Oil Type Emulsion)

| Ingredients | | Amount (weight %) |
|---|---|---|
| (1) | Titanium oxide fine particles ("TTO-51(C)," manufactured by Ishihara Sangyo Kaisha, Ltd.; average particle diameter: 10 to 30 μm) | 5.0 |
| (2) | Ether-modified silicone B ("KF-6015," manufactured by Shin-Etsu Silicone) | 0.5 |
| (3) | Ether-modified silicone A ("SH-3775C," manufactured by Toray-Dow Corning) | 1.0 |
| (4) | Methyl polysiloxane (6 cSt) | 5.0 |
| (5) | Decamethyl cyclopentasiloxane | 5.0 |
| (6) | 4-Methoxy-4'-t-butylbenzoylmethane | 2.0 |
| (7) | 2-Ethylhexyl p-methoxycinnamate | 3.0 |
| (8) | Squalane | 2.0 |
| (9) | Glycerol | 3.0 |
| (10) | Butyl p-hydroxybenzoate | 0.1 |
| (11) | Methyl p-hydroxybenzoate | 0.1 |
| (12) | Perfume | 0.05 |
| (13) | Distilled water | Balance |

The ultraviolet shielding effects and changes in appearance before and after skin application were evaluated for Example 31, Comparative Example 1, and Comparative Example 2. The results are shown in Table 1. Also, the ultraviolet shielding effects and changes in appearance (transparency) before and after skin application were evaluated for Example 34, Comparative Example 3, and Comparative Example 4. The results are shown in Table 2.

The ultraviolet shielding effect was evaluated by ultraviolet shielding indices and PCB values. Here, the ultraviolet shielding indices were calculated by the following equation using Hartley white guinea pigs.

$$\text{Ultraviolet Shielding Index} = \frac{\text{Minimum amount of ultraviolet light required for suntan on skin to which cosmetics were applied}}{\text{Minimum amount of ultraviolet light required for suntan on skin to which cosmetics were not applied}}$$

In addition, PFB values were obtained by a UVB method disclosed in J. Soc. Cosmet. Chem. Jpn. 28 (3), pp.254–261 (1994).

The changes in appearance before and after skin application were evaluated by carrying out white-color calibration using a color-and color difference meter (chromatic color-and color difference meter "CR-310," manufactured by Minolta Camera Co., Ltd.), and calculating the changes ($\Delta E^*_{ab}$) of the color-and-color difference before application ($L^{*0}$, $a^{*0}$, $b^{*0}$) and the color-and-color difference after application ($L^{*1}$, $a^{*1}$, $b^{*1}$). Here, $\Delta E^*_{ab}$ is a value defined according to JIS Z 8729-1980, which was calculated by the following equations:

$$\Delta L^* = (L^{*1} - L^{*0})$$

$$\Delta a^* = (a^{*1} - a^{*0})$$

$$\Delta b^* = (b^{*1} - b^{*0})$$

$$\Delta E^*_{ab} = \sqrt{(\Delta L^*)^2 + (\Delta a^*)^2 + (\Delta b^*)^2}$$

Here, $L^{*0}$, $a^{*0}$, $b^{*0}$, $L^*_1$, $a^{*1}$, and $b^{*1}$ were defined as follows:

$L^{*0}$: $L^*$ value (psychometric lightness) before skin application;

$a^{*0}$: $a^*$ value (psychometric chroma coordinates) before skin application;

$b^{*0}$: $b^*$ value (psychometric chroma coordinates) before skin application;

$L^{*1}$: $L^*$ value after skin application;

$a^{*1}$: $a^*$ value after skin application; and $b^{*1}$: $b^*$ value after skin application.

Also, SPF and PFA values were obtained by using an analyzer "SPF-290" (manufactured by The Optometrics Groups) and following the basic measurement technique according to the description given in the attached manual. Incidentally, PFA was indicated as an "Average UVA protection factor" in the attached manual.

TABLE 1

| | Example 31 | Comparative Example 1 | Comparative Example 2 |
|---|---|---|---|
| SPF | 19.6 | 19.2 | 7.5 |
| PFA | 9.2 | 8.9 | 3.2 |
| Ultraviolet Shielding Index | 7.5 | 6.5 | 3.0 |
| Change in Appearance (Δ E* ab) | 0.9 | 7.8 | 2.2 |

TABLE 2

| | Example 34 | Comparative Example 3 | Comparative Example 4 |
|---|---|---|---|
| SPF | 14.9 | 15.7 | 7.3 |
| PFA | 10.8 | 11.0 | 4.0 |
| Ultraviolet Shielding Index | 6.5 | 6.7 | 2.8 |
| Change in Appearance Δ E* ab) | 0.6 | 7.4 | 1.9 |

As is clear from the above results, it was found that the products obtained in Examples of the present invention had remarkably high ultraviolet shielding effects and high transparency.

INDUSTRIAL APPLICABILITY

When dispersed in a liquid or solid medium, the composite fine particles of the present invention show high light transmittance in the visible light region and also high shielding ability in the ultraviolet light region by the scattering ability and the absorption ability of the daughter particles. In addition, although the daughter particles having high catalytic activities are present in the inner portion of the matrix particles or the surface thereof, by coating the surface of the composite fine particles comprising the daughter particles and the matrix particles with inorganic materials having substantially no catalytic activities, the catalytic activities owned by the daughter particles do not cause to deteriorate the dispersant or the medium which is present in the periphery of the composite fine particles. In other words, the composite fine particles of the present invention are composites of ultrafine particles having ultraviolet shielding ability and the surface of the composite fine particles are coated by the inorganic materials having substantially no catalytic activities, so that the resulting composite fine particles have substantially no catalytic activities, while retaining such optical properties inherently owned by the ultrafine particles as high transparency in the visible light region and high shielding ability in the ultraviolet light region, the above properties being stably exhibited in an easy-to-handle, fine particle size. Further, in the case where the composite fine particles of the present invention are subjected to a water-repellent treatment, they can stably and uniformly disperse when incorporated in water-in-oil type cosmetics or oil-in-water type cosmetics, so that the deterioration of cosmetics base materials are not likely to be caused. When the composite fine particles of the present invention are incorporated in cosmetics, the resulting cosmetics have good smoothness on skin, excellent spreading on skin without unevenness, and excellent transparency, and are free from unnatural whitening, thereby having excellent ultraviolet shielding ability, and have excellent safety and stability. Further, since the composite fine particles of the present invention have excellent transparency, substantially no coloring of the cosmetics are lost, and the degree of freedom of the amount of the composite fine particles which can be formulated to cosmetics is also high.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. Ultraviolet shielding composite fine particles having transparency in a visible light region, comprising:
   (a) matrix particles comprising an aggregate of primary particles having an average particle diameter of from 0.001 to 0.3 $\mu$m, said aggregate being formed while the primary particles retain their shapes; and
   (b) daughter particles having an average particle diameter of from 0.001 to 0.1 $\mu$m, said daughter particles being dispersed in and supported by said matrix particles, wherein said daughter particles have a smaller band gap energy than the particles constituting said matrix particles and are capable of absorbing ultraviolet light, and wherein the surface of said ultraviolet shielding composite fine particles is coated with an inorganic material, thereby showing substantially no catalytic activities.

2. The ultraviolet shielding composite fine particles according to claim 1, wherein said particles constituting the matrix particles have a band gap energy of from 3 to 9 eV.

3. The ultraviolet shielding composite fine particles according to claim 1, wherein the difference between the band gap energies of the daughter particles and the particles constituting the matrix particles is not less than 0.2 eV.

4. The ultraviolet shielding composite fine particles according to claim 1, wherein said daughter particles are dispersed in and supported by said matrix particles in an amount of from 0.1 to 85% by volume.

5. The ultraviolet shielding composite fine particles according to claim 1, wherein the average particle diameter of the ultraviolet shielding composite fine particles is not more than 0.5 $\mu$m.

6. The ultraviolet shielding composite fine particles according to claim 1, wherein the average refractive index of the ultraviolet shielding composite fine particles is from 1.3 to 2.5.

7. The ultraviolet shielding composite fine particles according to claim 1, wherein said particles constituting the matrix particles are selected from the group consisting of metal oxides, fluorine compounds, and mixtures thereof.

8. The ultraviolet shielding composite fine particles according to claim 7, wherein said metal oxide is selected from the group consisting of $SiO_2$, $Al_2O_3$, and a mixture thereof.

9. The ultraviolet shielding composite fine particles according to claim 1, wherein said daughter particles are selected from the group consisting of $TiO_2$, ZnO, $CeO_2$, SiC, $SnO_2$, $WO_3$, $BaTiO_3$, $CaTiO_3$, $SrTiO_3$, and mixtures thereof.

10. The ultraviolet shielding composite fine particles according to claim 1, wherein the inorganic material is a metal oxide.

11. The ultraviolet shielding composite fine particles according to claim 10, wherein the metal oxide used for the inorganic material is selected from the group consisting of $SiO_2$, $Al_2O_3$, and a mixture thereof.

12. The ultraviolet shielding composite fine particles according to claim 1, wherein the surface of said composite fine particles is further treated by a water-repellant.

13. The ultraviolet shielding composite fine particles according to claim 1, wherein said ultraviolet shielding composite fine particles have a light transmittance of not less than 80% at a wavelength of 800 nm, a light transmittance of not less than 20% at a wavelength of 400 nm, and a light transmittance of not more than 5% at least at one wavelength within the range from 380 nm to 300 nm, the light transmittance being determined by suspending said composite fine particles in a medium having substantially the same refractive index level as the composite fine particles, and measuring with an ultraviolet-visible light spectrophotometer using an optical cell having an optical path length of 1 mm.

14. The ultraviolet shielding composite fine particles according to claim 1, obtained by the steps of:
   (a) preparing a liquid mixture comprising:
      (i) starting materials for matrix particles which are present in one or more forms selected from the group consisting of sols containing particles constituting matrix particles and powders of the matrix particles, the matrix particles having a primary particle with an average particle diameter of from 0.001 to 0.3 $\mu$m; and
      (ii) starting materials for daughter particles which are present in one or more forms selected from the group consisting of sols containing daughter particles and powders of the daughter particles, the daughter particles having a primary particle with an average particle diameter of from 0.001 to 0.1 $\mu$m, and treating the liquid mixture in a mill and/or an apparatus for high-pressure dispersion, to thereby produce composite fine particles wherein the daughter particles and the matrix particles are aggregated;

(b) coating the composite fine particles obtained in step (a) with an inorganic material;

(c) subjecting the composite fine particles coated with the inorganic material obtained in step (b) to a water-repellent treatment; and (d) drying and/or pulverizing the composite fine particles subjected to the water-repellent treatment obtained in step (c).

15. A dispersion oil agent of the ultraviolet shielding composite fine particles as defined in claim 1, obtained by the steps of:

(a) preparing a liquid mixture comprising:
(i) starting materials for matrix particles which are present in one or more forms selected from the group consisting of sols containing particles constituting matrix particles and powders of the matrix particles, the matrix particles having a primary particle with an average particle diameter of from 0.001 to 0.3 μm; and
(ii) starting materials for daughter particles which are present in one or more forms selected from the group consisting of sols containing daughter particles and powders of the daughter particles, the daughter particles having a primary particle with an average particle diameter of from 0.001 to 0.1 μm, and treating the liquid mixture in a mill and/or an apparatus for high-pressure dispersion, to thereby produce composite fine particles wherein the daughter particles and the matrix particles are aggregated;

(b) coating the composite fine particles obtained in step (a) with an inorganic material;

(c) subjecting the composite fine particles coated with the inorganic material obtained in step (b) to a water-repellent treatment; and (d') dispersing in an oil agent the composite fine particles subjected to the water-repellent treatment obtained in step (c).

16. A method for producing the ultraviolet shielding composite fine particles comprising daughter particles being dispersed in and supported by said matrix particles, the ultraviolet shielding composite fine particles having substantially no catalytic activities and having transparency in a visible light region, obtained by the steps of:

(a) preparing a liquid mixture comprising (i) starting materials for matrix particles which are present in one or more forms selected from the group consisting of sols containing particles constituting matrix particles and powders of the matrix particles, the matrix particles having a primary particle with an average particle diameter of from 0.001 to 0.3 μm; and (ii) starting materials for daughter particles which are present in one or more forms selected from the group consisting of sols containing daughter particles and powders of the daughter particles, the daughter particles having a primary particle with an average particle diameter of from 0.001 to 0.1 μm, and treating the liquid mixture in a mill and/or an apparatus for high-pressure dispersion, to thereby produce composite fine particles wherein the daughter particles and the matrix particles are aggregated; and (b) coating the composite fine particles obtained in step (a) with-an inorganic material.

17. The method according to claim 16, further comprising, subsequent to said step (b):

(c) subjecting the composite fine particles coated with the inorganic material obtained in step (b) to a water-repellent treatment.

18. The method according to claim 17, further comprising, subsequent to said step (c):

(d) drying and/or pulverizing the composite fine particles subjected to the water-repellent treatment obtained in step (c).

19. A method for producing a dispersion oil agent of the ultraviolet shielding composite fine particles comprising daughter particles being dispersed in and supported by said matrix particles, the ultraviolet shielding composite fine particles having substantially no catalytic activities and having transparency in a visible light region, obtained by the steps of:

(a) preparing a liquid mixture comprising (i) starting materials for matrix particles which are present in one or more forms selected from the group consisting of sols containing particles constituting matrix particles and powders of the matrix particles, the matrix particles having a primary particle with an average particle diameter of from 0.001 to 0.3 μm; and (ii) starting materials for daughter particles which are present in one or more forms selected from the group consisting of sols containing daughter particles and powders of the daughter particles, the daughter particles having a primary particle with an average particle diameter of from 0.001 to 0.1 μm, and treating the liquid mixture in a mill and/or an apparatus for high-pressure dispersion, to thereby produce composite fine particles wherein the daughter particles and the matrix particles are aggregated;

(b) coating the composite fine particles obtained in step (a) with an inorganic material;

(c) subjecting the composite fine particles coated with the inorganic material obtained in step (b) to a water-repellent treatment; and (d') dispersing in an oil agent the composite fine particles subjected to the water-repellent treatment obtained in step (c).

20. Cosmetics comprising ultraviolet shielding composite fine particles as defined in claim 1.

21. Cosmetics comprising the dispersion oil agent of the ultraviolet shielding composite fine particles as defined in claim 15.

22. The cosmetics according to claim 20, wherein an amount of said ultraviolet shielding composite fine particles is from 0.01 to 50% by weight.

23. The cosmetics according to claim 20, further containing an ultraviolet protecting agent.

24. The cosmetics according to claim 20, wherein SPF measured by using an analyser "SPF-290," manufactured by The Optometrics Group is not less than 8, and wherein ΔE*ab before and after skin application is not more than 3 as defined according to JIS Z8729-1980.

25. A method of shielding skin from ultraviolet light which comprises applying to said skin, a cosmetic composition comprising ultraviolet shielding composite particles according to claim 1.

* * * * *